United States Patent
Clineff et al.

(10) Patent No.: US 9,662,821 B2
(45) Date of Patent: May 30, 2017

(54) BIOACTIVE COMPOSITES OF POLYMER AND GLASS AND METHOD FOR MAKING SAME

(71) Applicant: Orthovita, Inc., Malvern, PA (US)

(72) Inventors: Theodore D. Clineff, Phoenixville, PA (US); Marissa M. Conrad, Philadelphia, PA (US); Matthew B. Havener, West Conshohocken, PA (US); James P. Murphy, Newtown Square, PA (US); Zachary S. Szczerbinski, Turnersville, NJ (US)

(73) Assignee: Orthovita, Inc., Malvern, PA (US)

( * ) Notice: Subject to any disclaimer, the term of this patent is extended or adjusted under 35 U.S.C. 154(b) by 92 days.

(21) Appl. No.: 14/699,333

(22) Filed: Apr. 29, 2015

(65) Prior Publication Data

US 2015/0273751 A1 Oct. 1, 2015

Related U.S. Application Data

(63) Continuation of application No. 12/577,835, filed on Oct. 13, 2009, now abandoned.

(60) Provisional application No. 61/141,453, filed on Dec. 30, 2008.

(51) Int. Cl.

| | |
|---|---|
| C08K 3/40 | (2006.01) |
| B29C 47/00 | (2006.01) |
| A61C 8/00 | (2006.01) |
| A61F 2/28 | (2006.01) |
| A61F 2/30 | (2006.01) |
| A61F 2/32 | (2006.01) |
| A61F 2/44 | (2006.01) |
| A61F 2/46 | (2006.01) |
| A61L 27/44 | (2006.01) |
| A61L 31/12 | (2006.01) |
| B29C 47/10 | (2006.01) |
| B29C 47/82 | (2006.01) |
| A61B 17/74 | (2006.01) |
| A61B 17/80 | (2006.01) |
| A61B 17/86 | (2006.01) |
| B29K 71/00 | (2006.01) |
| B29K 105/12 | (2006.01) |
| B29K 509/08 | (2006.01) |
| B29L 31/00 | (2006.01) |

(52) U.S. Cl.
CPC ........ *B29C 47/0004* (2013.01); *A61C 8/0012* (2013.01); *A61C 8/0016* (2013.01); *A61F 2/28* (2013.01); *A61F 2/30734* (2013.01); *A61F 2/32* (2013.01); *A61F 2/4455* (2013.01); *A61F 2/4611* (2013.01); *A61L 27/446* (2013.01); *A61L 31/128* (2013.01); *B29C 47/1027* (2013.01); *B29C 47/822* (2013.01); *C08K 3/40* (2013.01); *A61B 17/742* (2013.01); *A61B 17/80* (2013.01); *A61B 17/86* (2013.01); *A61F 2/2803* (2013.01); *A61F 2/2875* (2013.01); *A61F 2/446* (2013.01); *A61F 2/447* (2013.01); *A61F 2/4465* (2013.01); *A61F 2002/2882* (2013.01); *A61F 2002/30062* (2013.01); *A61F 2002/3082* (2013.01); *A61F 2002/3085* (2013.01); *A61F 2002/30131* (2013.01); *A61F 2002/30738* (2013.01); *A61F 2002/30787* (2013.01); *A61F 2002/30828* (2013.01); *A61F 2002/30892* (2013.01); *A61F 2002/448* (2013.01); *A61F 2002/4475* (2013.01); *A61F 2002/4622* (2013.01); *A61F 2002/4631* (2013.01); *A61F 2210/0004* (2013.01); *A61F 2230/0013* (2013.01); *A61F 2310/00329* (2013.01); *B29K 2071/00* (2013.01); *B29K 2105/126* (2013.01); *B29K 2509/08* (2013.01); *B29K 2995/0056* (2013.01); *B29L 2031/7532* (2013.01); *C08G 2650/40* (2013.01); *C08K 2201/005* (2013.01)

(58) Field of Classification Search
USPC ........ 534/494; 523/220; 264/328.1; 524/494
See application file for complete search history.

(56) References Cited

U.S. PATENT DOCUMENTS

| | | | |
|---|---|---|---|
| 4,638,037 A | 1/1987 | Ward et al. | |
| 5,008,364 A | 4/1991 | Ittemann et al. | |
| 5,043,369 A | 8/1991 | Bahn et al. | |
| 5,074,916 A | 12/1991 | Hench et al. | |
| 5,336,465 A | 8/1994 | Matsunaga et al. | |
| 5,468,544 A | 11/1995 | Marcolongo et al. | |

(Continued)

FOREIGN PATENT DOCUMENTS

| | | |
|---|---|---|
| EP | 0055472 B1 | 11/1985 |
| EP | 0125816 B1 | 9/1987 |

(Continued)

OTHER PUBLICATIONS

European Office Action for Application No. 07861377.5 dated Jul. 5, 2013.

Bakar, M.S. A. et al; Tensile properties, tension-tension fatigue and biological response of polyetheretherketone-hydroxyapatite composites for load-bearing orthopedic implants; Biomaterials 24 (2003) pp. 2245-2250, Elsevier Sci Ltd.

Barton, A.J. et al; Bacterial adhesion to orthopedic implants polymers, Journal of Biomedical Materials Research, vol. 30, pp. 403-410 (1996) John Wiley & Sons, Inc.

(Continued)

*Primary Examiner* — Tae H Yoon
(74) *Attorney, Agent, or Firm* — Lerner, David, Littenberg, Krumholz & Mentlik, LLP

(57) ABSTRACT

The present invention relates to a method of preparing a bioactive composite, the method comprising the steps of a) adding in a solid state a biocompatible polymer and a bioactive glass to an extruder to form an extrudable material; b) applying energy to the extrudable material to at least the melting temperature of the biocompatible polymer to melt mix the biocompatible polymer and bioactive glass; and c) extruding a bioactive composite.

19 Claims, 76 Drawing Sheets

(56) References Cited

U.S. PATENT DOCUMENTS

| | | | |
|---|---|---|---|
| 5,645,934 | A | 7/1997 | Marcolongo et al. |
| 5,681,872 | A | 10/1997 | Erbe |
| 5,721,049 | A | 2/1998 | Marcolongo et al. |
| 5,914,356 | A | 6/1999 | Erbe |
| 6,121,172 | A | 9/2000 | Marcolongo et al. |
| 6,270,347 | B1 | 8/2001 | Webster et al. |
| 6,399,693 | B1 | 6/2002 | Brennan et al. |
| 6,602,293 | B1 | 8/2003 | Biermann et al. |
| 6,800,245 | B1 | 10/2004 | Erbe et al. |
| 6,808,908 | B2 | 10/2004 | Yao et al. |
| 6,979,702 | B1 | 12/2005 | Ma et al. |
| 6,987,136 | B2 | 1/2006 | Erbe et al. |
| 7,189,409 | B2 | 3/2007 | Pirhonen et al. |
| D539,934 | S | 4/2007 | Blain |
| D541,940 | S | 5/2007 | Blain |
| 7,230,039 | B2 | 6/2007 | Trieu et al. |
| 7,238,203 | B2 | 7/2007 | Bagga et al. |
| 7,241,486 | B2 | 7/2007 | Pirhonen |
| D564,095 | S | 3/2008 | Blain |
| D566,276 | S | 4/2008 | Blain |
| 8,597,675 | B2 | 12/2013 | Murphy et al. |
| 2001/0043940 | A1 | 11/2001 | Boyce et al. |
| 2002/0115742 | A1 | 8/2002 | Trieu et al. |
| 2003/0031698 | A1 | 2/2003 | Roeder et al. |
| 2003/0087984 | A1 | 5/2003 | Erbe et al. |
| 2003/0100086 | A1 | 5/2003 | Yao et al. |
| 2003/0125739 | A1 | 7/2003 | Bagga et al. |
| 2003/0206928 | A1 | 11/2003 | Tormala et al. |
| 2003/0232122 | A1 | 12/2003 | Chappa et al. |
| 2004/0009228 | A1 | 1/2004 | Tormala et al. |
| 2005/0177238 | A1 | 8/2005 | Khandkar et al. |
| 2005/0283255 | A1 | 12/2005 | Geremakis et al. |
| 2006/0015184 | A1 | 1/2006 | Winterbottom et al. |
| 2006/0063882 | A1 | 3/2006 | Velev et al. |
| 2006/0172877 | A1 | 8/2006 | Fechner et al. |
| 2007/0278720 | A1 | 12/2007 | Wang et al. |
| 2007/0293948 | A1 | 12/2007 | Bagga et al. |
| 2008/0069856 | A1 | 3/2008 | Lyu et al. |
| 2008/0234532 | A1 | 9/2008 | De Langen et al. |
| 2008/0258337 | A1* | 10/2008 | Ajbani ............... C08F 283/08 264/241 |
| 2009/0164023 | A1 | 6/2009 | Devine |
| 2009/0288831 | A1 | 11/2009 | Williams et al. |
| 2010/0094418 | A1 | 4/2010 | Zenati et al. |
| 2010/0129416 | A1* | 5/2010 | Murphy ............... A61L 27/446 424/423 |

FOREIGN PATENT DOCUMENTS

| | | | |
|---|---|---|---|
| EP | 0148633 | B1 | 5/1989 |
| EP | 0365236 | A1 | 4/1990 |
| EP | 2243500 | A1 | 10/2010 |
| JP | 02-225343 | A | 9/1990 |
| JP | 09-505345 | A | 5/1997 |
| JP | 2000515171 | A | 11/2000 |
| JP | 2004521685 | A | 7/2004 |
| JP | 2005511110 | A | 4/2005 |
| JP | 2005520629 | A | 7/2005 |
| JP | 2005535367 | A | 11/2005 |
| WO | 9514127 | A1 | 5/1995 |
| WO | 99/36368 | A1 | 7/1999 |
| WO | 03105919 | A1 | 12/2003 |
| WO | 2008/039488 | A2 | 4/2008 |
| WO | 2010/007424 | A1 | 1/2010 |
| WO | 2010/043900 | A1 | 4/2010 |

OTHER PUBLICATIONS

Bureau, MN; et al; CaP coating on PEEK varies upon processing conditions, Industrial Materials Institute, National Research Council Canada, 55th Annual Meeting of the Orthopeadic Research Society, Poster No. 470, 2009.

Chou, Yu-Cheng et al; Efficacy of anterior cervical fusion: Comparison of titanium cages, polyetheretherketone (PEEK) cages and autogenous bone grafts; Journal of Clinical Neuroscience 15 (2008) 1240-1245.

Converse and Roeder; Hydroxyapatite Wisker Reinforced Polyetheretherketone: A Bone Mimetic Composite; 52nd Annual Meeting of the Orthopaedic Research Society; Mar. 19-22, 2006; Paper 0886; 2 pgs.

Converse, G. L. et al; Processing and tensile properties of hydroxyapatite-whisker-reinforced polyetheretherketone; Biomaterials 28 (2007), pp. 927-935 Elsevier Ltd.

Fan, J.P. et al; Influence of interphase layer on the overall elasto-plastic behaviors of HA/PEEK biocomposite, Biomaterials 25 (2004), pp. 5363-5373, Elsevier Ltd.

Green, Stuart and Schlegel, Jorg; A polyaryletherketone biomaterial for use in medical implant application, Polymers for the Medical Industry (2001) Victrex pic, UK and Victrex Europa GmbH, Germany.

Jiya, Timothy et al; Posterior lumbar interbody fusion using nonresorbable poly-ether-ether-ketone versus resorbable poly-L-Lactide-Co-D, L-Lactide Fusion Devices; Spine vol. 23 No. 3 pp. 233-237 (2009) Lippincott Williams & Wilkins.

Jones, D.P. et al; Mechanical properties of poly(ether-ether-ketone) for engineering applications; Mechanical properties of PEEK: Polymer, 1985, vol. 26, pp. 1385-1393, August (Conference issue), Butterworth & Co.

Kim et al; Bioactive Composites Consisting of PEEK and Calcium Silicate Powders; Journal of Biomaterials Applications, Aug. 29, 2008; vol. 00; pp. 1-14 Beta-TCP containing three-dimensional laser sintered polyetheretherketone composites on oseoblasts in vitro.

Kurtz, S.M. and Devine, J.N.; PEEK biomaterials in trauma, orthopedic, and spinal implants; Biomaterials 28 (2007), D pp. 4845-4869, Elsevier Ltd.

Lin, T.W. et al; Glass peek composite promotes proliferation and osteocalcin production of human osteoblastic cells,11 Student Research Award in the Undergraduate, Master, Candidate, or Health Science Degree Candidate Category, Society for Biomaterials 23rd Annual Meeting, New Orleans, LA, Apr. 30-May 4, 2007; John Wiley & Sons, Inc.

Inagaki N. et al; Surface modification of poly(aryl ether ether ketone) film by remote oxygen plasma; Journal of Applied Polymer Science, vol. 68, pp. 271-279 (1998) John Wiley & Sons, Inc.

Pino, M., et al; Nucleation and growth of apatite on NaOH-treated PEEK, HDPE, and UHMWPE for artificial cornea materials; Acta Biomaterials 4 (2008) pp. 1827-1836, Elsevier Ltd.

Rivard C.H., et al.; In vivo biocompatibility testing of peek polymer for a spinal implant system: A study in rabbits; Peek Biocompatibility for a Spinal Implant, J. Biomed Mater Res 62: 488-498, 2002 Wiley Periodicals, Inc.

Sagomonyants, K.B. et al; The in vitro response of human osteoblasts to polyetheretherketone (PEEK) substrates compared to commercially pure titanium; Biomaterials 29 (2008) pp. 1563-1572, Elsevier Ltd.

Tang S.M. et al; Tension-Tension fatigue behavior of hydroxyapatite reinforced polyetheretherketone composites International Journal of Fatigue 26 (2004) pp. 49-57, Elsevier Ltd.

von Wilmonsky et al; Effects of bioactive glass and Beta-TCP containing three-dimensional laser sintered polyetheretherketone composites or osteoblasts in vitro; Wiley InterScience; Jan. 28, 2008; pp. 1-7.

Wang, Min; Developing bioactive composite materials for tissue replacement; Biomaterials 24 (2003) pp. 2133-2151, Elsevier Ltd.

Wong, K.L. et al; Mechanical properties and in vitro response of strontium-containing hydroxyapatite/polyetheretherkone composites; Biomaterials 30 (2009) 3810-3817, Elsevier Ltd.

International Search Report of PCT/US09/68257 dated Feb. 23, 2010.

Extended European Search Report for Application No. EP09866889 dated Dec. 3, 2013.

(56) References Cited

OTHER PUBLICATIONS

Baker, M.S. et al; Tensile properties, tension-tension fatigue and biological response of polyetheretherketone-hydroxyapatite composites for load-bearing orthopedic implants; Biomaterials 24(2003) pp. 2245-2250, Elvsevier Sci Ltd.

Barton, A.J. et al; Bacterial adhesion to orthopedic implants polymers, Journal of Biomaterial Materials Research, vol. 30 pp. 403-410 (1996) John Wiley & Sons, Inc.

Converse, G.L. et al; Processing and tensile properties of hydroxyapatite-whisker-reinforced polyetheretherketone; Biomaterials 28(2007), pp. 927-935 Elvsevier Ltd.

Inagaki N. et al; Surface modification of poly( aryl ether ether ketone) film by remote oxygen plasma; Journal of Applied Polymer Science. vol. 68, pp. 271-279 (1998) John Wiley & Sons, Inc.

Jones, D.P. et al; Mechanical properties of poly( ether ether ketone) for engineering applications; Mechanical properties of PEEK: Polymer, 1985, vol. 26, pp. 1385-1393, August (Conference issue), Butterworth & Co.

Kurtz, S.M. and Devine, J.N.; PEEK biomaterials in trauma, orthopedic, and spinal implants; Biomaterials 28(2007), pp. 4845-4869, Elsevier Ltd.

Lin, T.W. et al; Glass peek composite promotes proliferation and osteocalcin production of osteoblastic cells, Student Research Award in the Undergraduate, Master, Candidate, or Health Science Degree Candidate Category, Society for Biomaterials 23rd Annual Meeting, New Orleans, LA, Apr. 30-May 4, 2007; John Wiley & Sons, Inc.

Pino, M. et al; Nucleation and growth of apatite on NaOH-treated PEEK, HDPE, and UHMWPE for artifical cornea materials; Acta Biomaterials 4 (2008) pp. 1827-1836, Elsevier Ltd.

Rivard C. H., et al.; In vivo biocompatibility testing of peek polymer for a spinal implant system: A study in rabbits; PEEK Biocompatibility for a Spinal Implant, J. Biomed Mater Res. 62: 488-498, 2002 Wiley Periodicals, Inc.

Wang, Min; Developing Bioactive composite materials for tissue replacement; Biomaterials 24 (2003) pp. 2133-2151 Elsevier Ltd.

Bureau, MN et al; CaP coating on PEEK varies upon processing conditions, Industrial Materials Institute, National Research Council Canada, 55th Annual Meeting of the Orthopeadic Research Society, Poster No. 470, 2009.

Converse and Roeder, "Hydroxyapatite Wisker Reinforced Polyetheretherketone: A Bone Mimetic Composite;" 52nd Annual Meeting of the Orthopaedic Research Society; Mar. 19-22, 2006; Paper 0886 (2 pages).

Von Wilmowsky et al., "Effects of bioactive glass and beta-TCP containing three dimensional laser sintered polyetheretherketone composites on osteoblasts in vitro." Wiley InterScience; Jan. 28, 2008; pp. 1-7.

Kim et al.; Bioactive Composites Consisting of PEEK and Calcium Silicate Powders; Journal of Biomaterials Applications, Aug. 29, 2008; vol. 00; pp. 1-14.

Sagomonyants, K.B. et al, The in vitro response of human osteoblasts to polyetheretherketone (PEEK) substrates . . . pure titanium, Biomatl 29(2008)1563-1572 Elsevier ltd.

Supplementary European Search Report for Application No. EP07861377 dated Oct. 2, 2012.

Extended European Search Report for Application No. EP07861377.5 dated Oct. 11, 2012.

Australian Office Action for Application No. 2007300509 dated May 29, 2012.

Japanese Office Action for Application No. 2009-529275 dated Aug. 10, 2012.

International Search Report for PCT/US07/20764 dated Mar. 25, 2008.

Japanese Office Action for Application No. 2009-529275 dated Jan. 10, 2013.

* cited by examiner

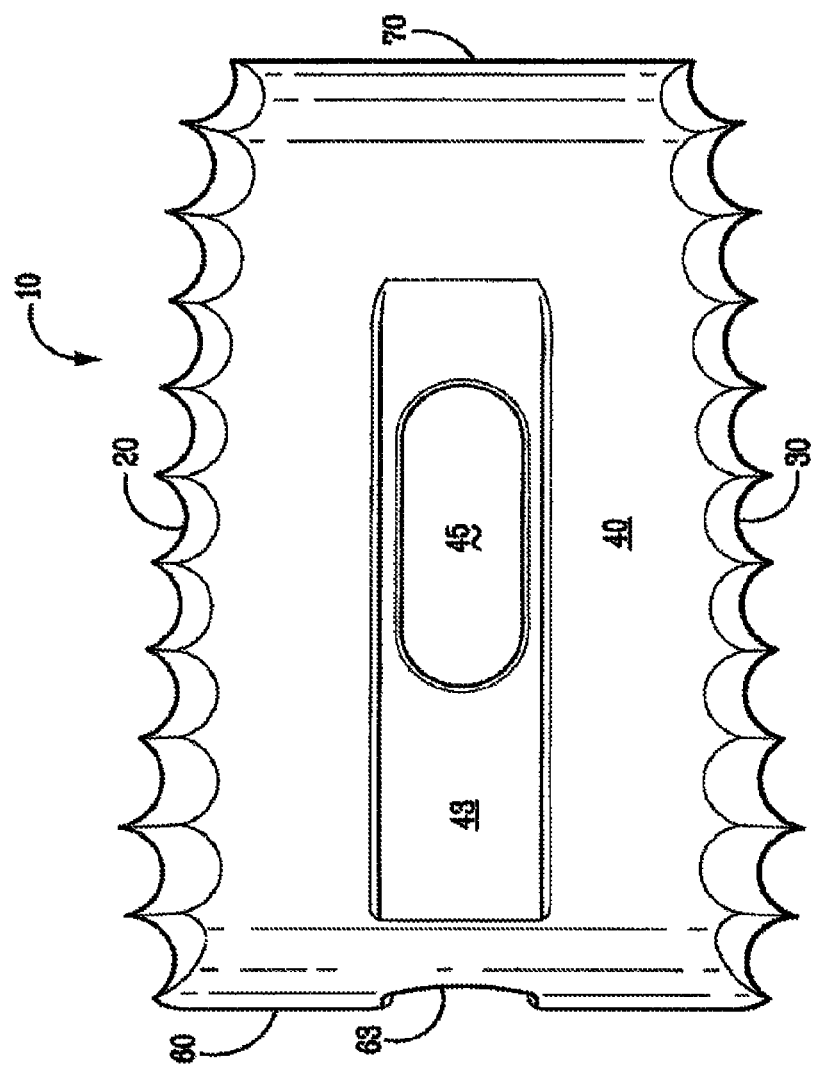

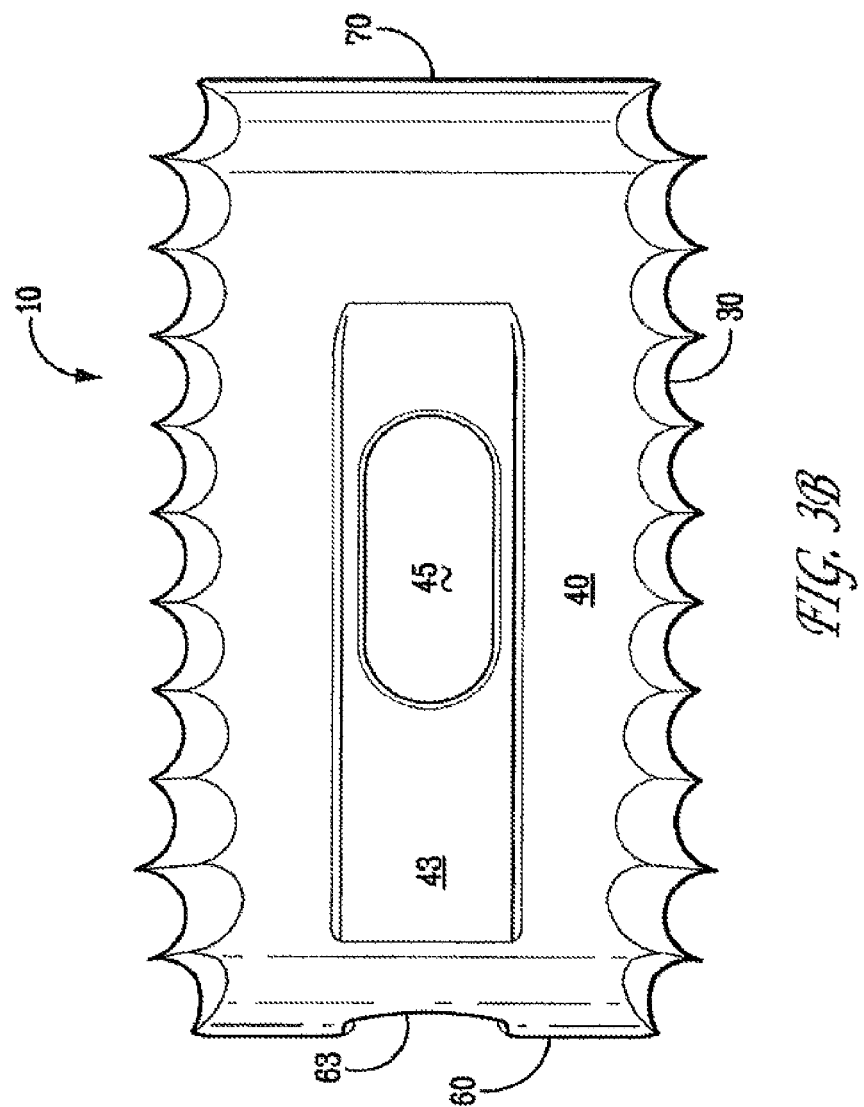

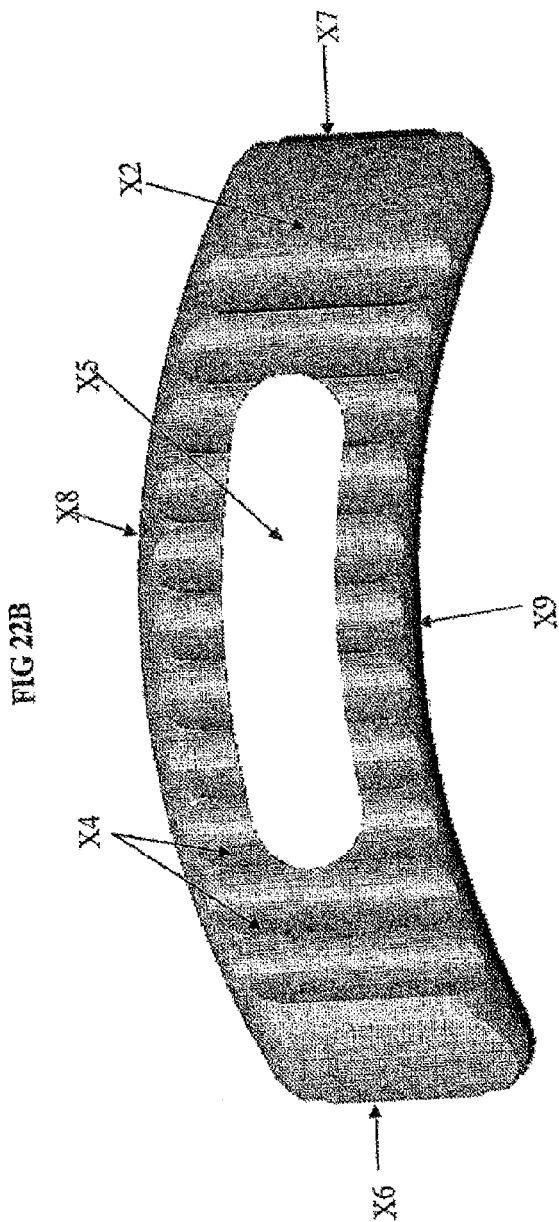

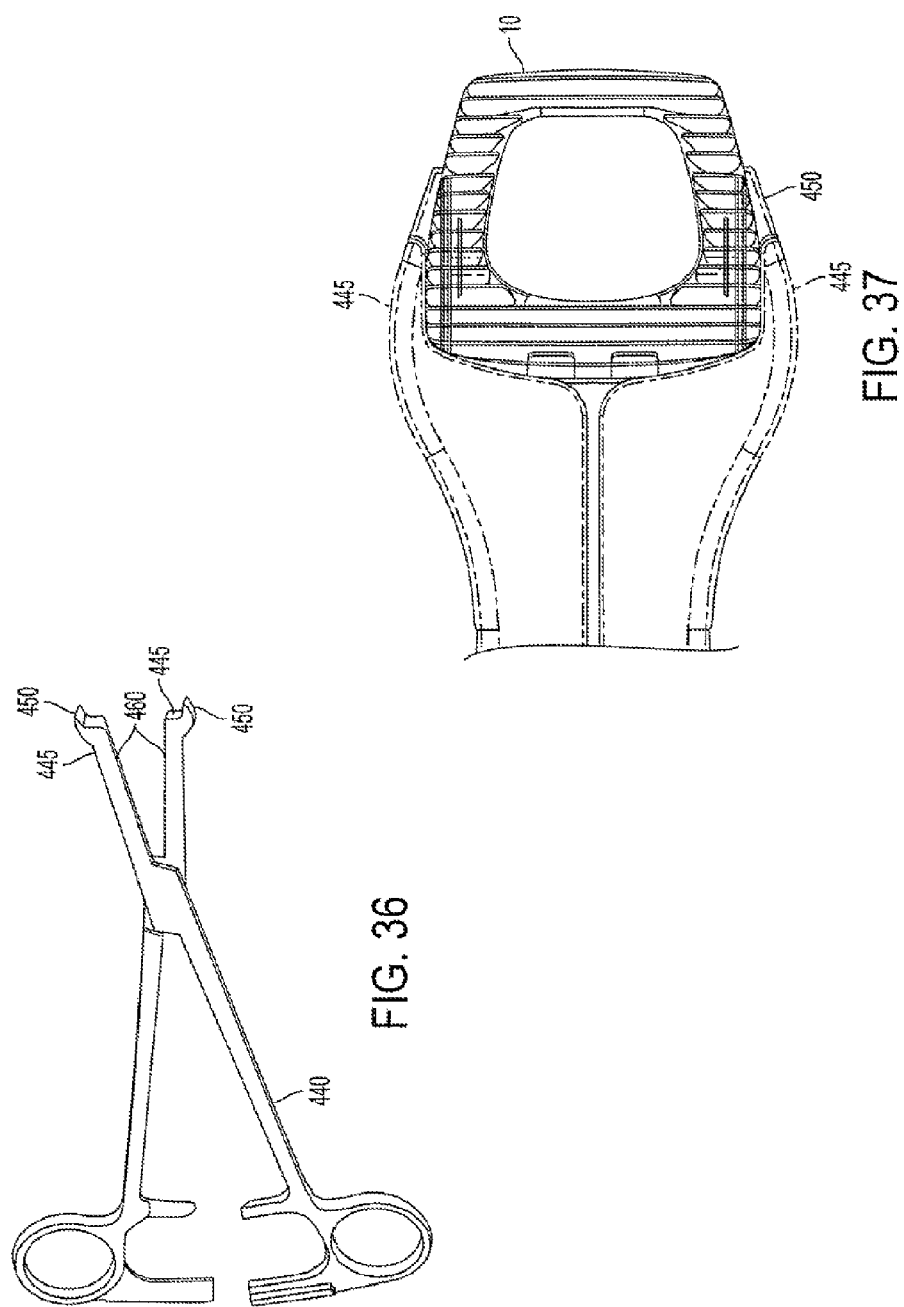

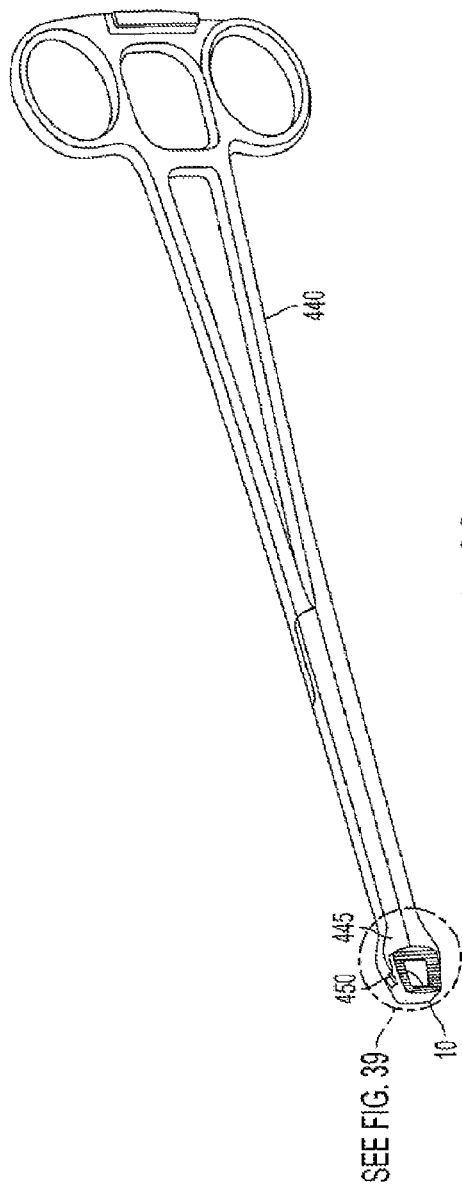
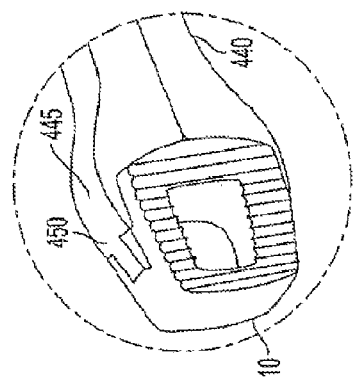
FIG. 38
FIG. 39

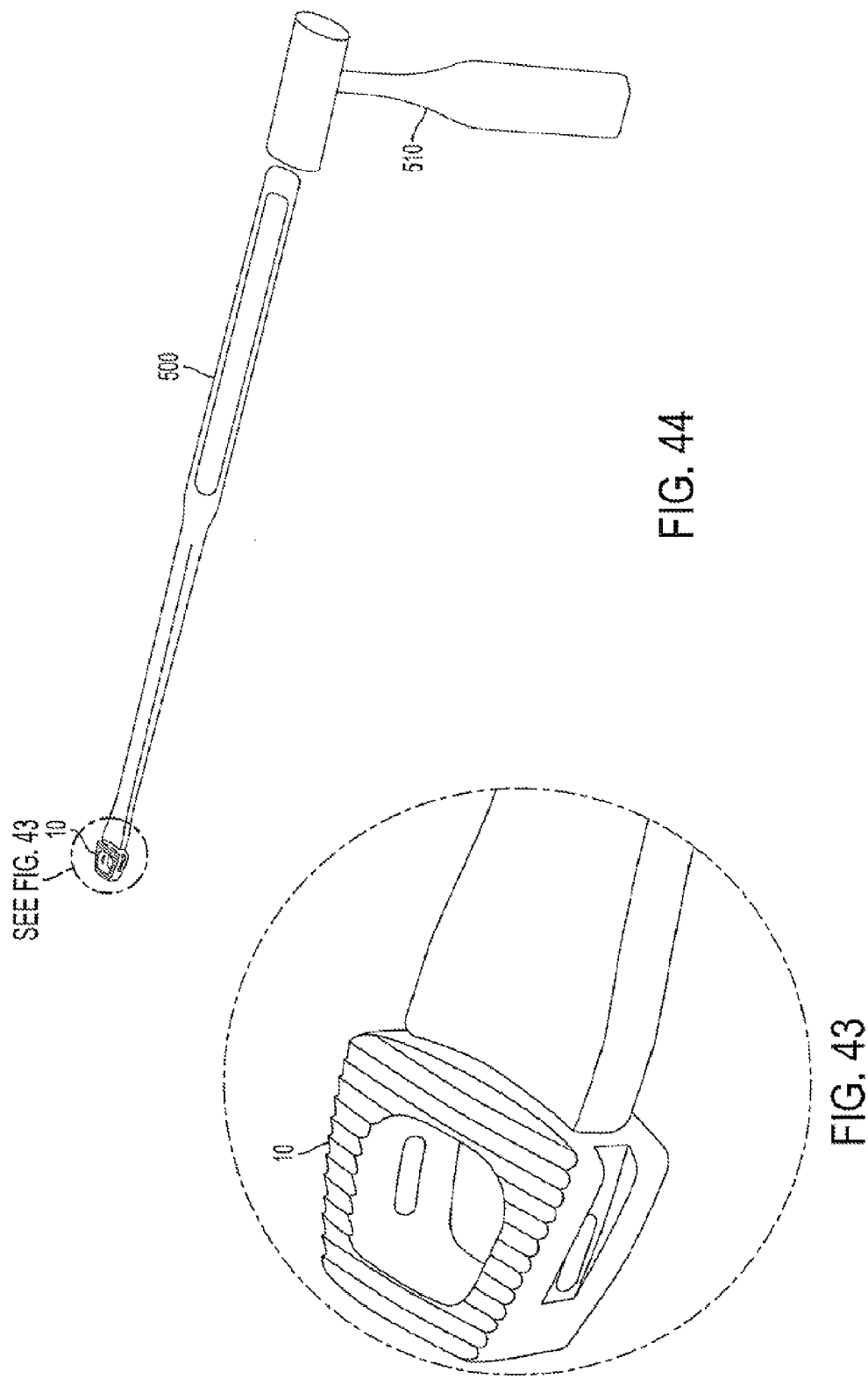

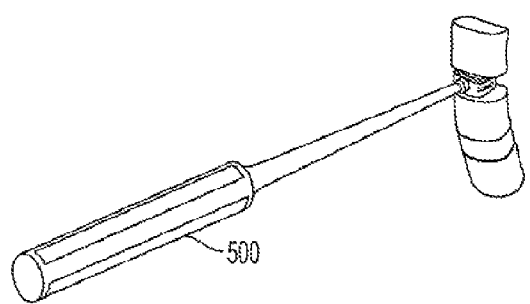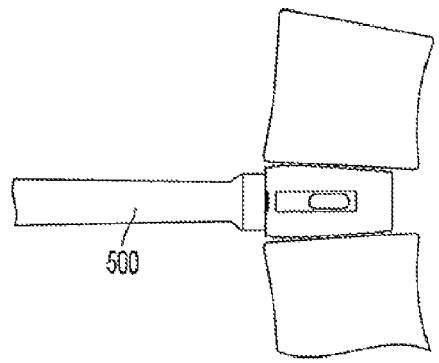
FIG. 45　　　　　　FIG. 46
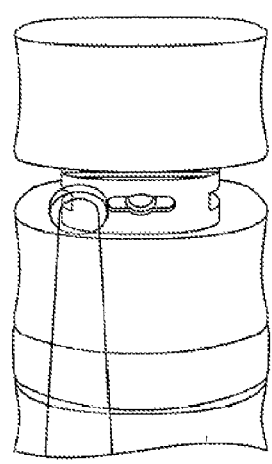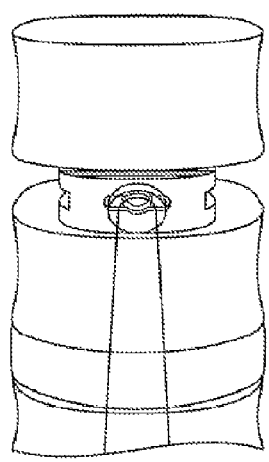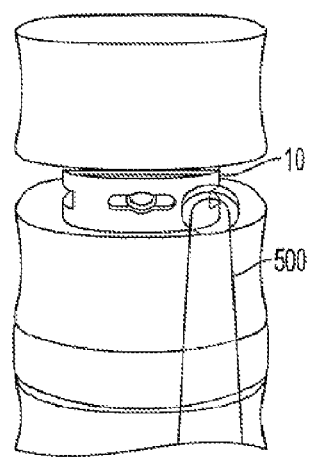
FIG. 47a　　　FIG. 47b　　　FIG. 47c

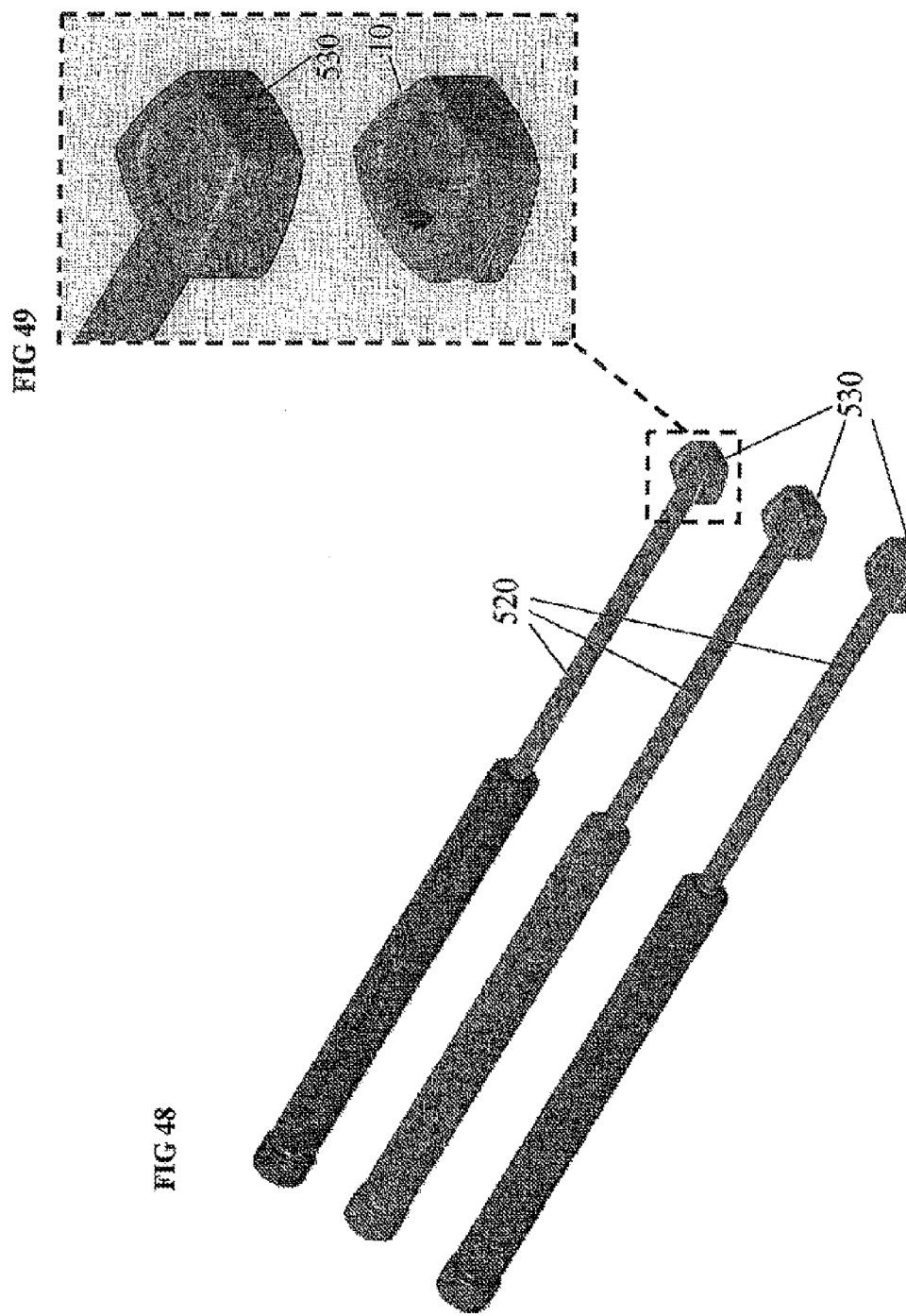

90% PEEK / 10%
Combeite 50x

80% PEEK / 20%
Combeite 50x

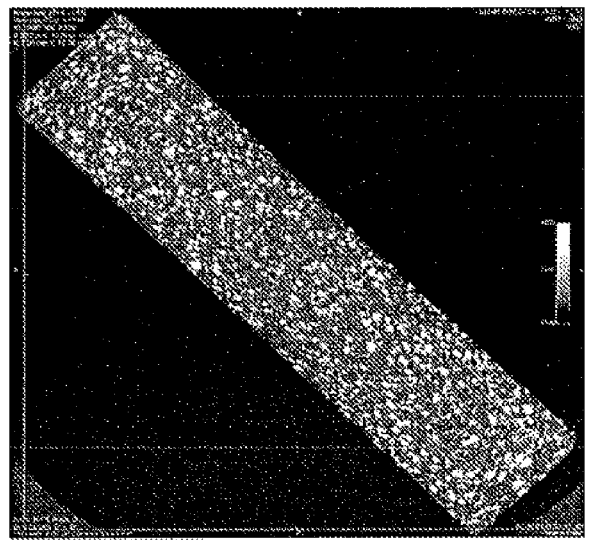
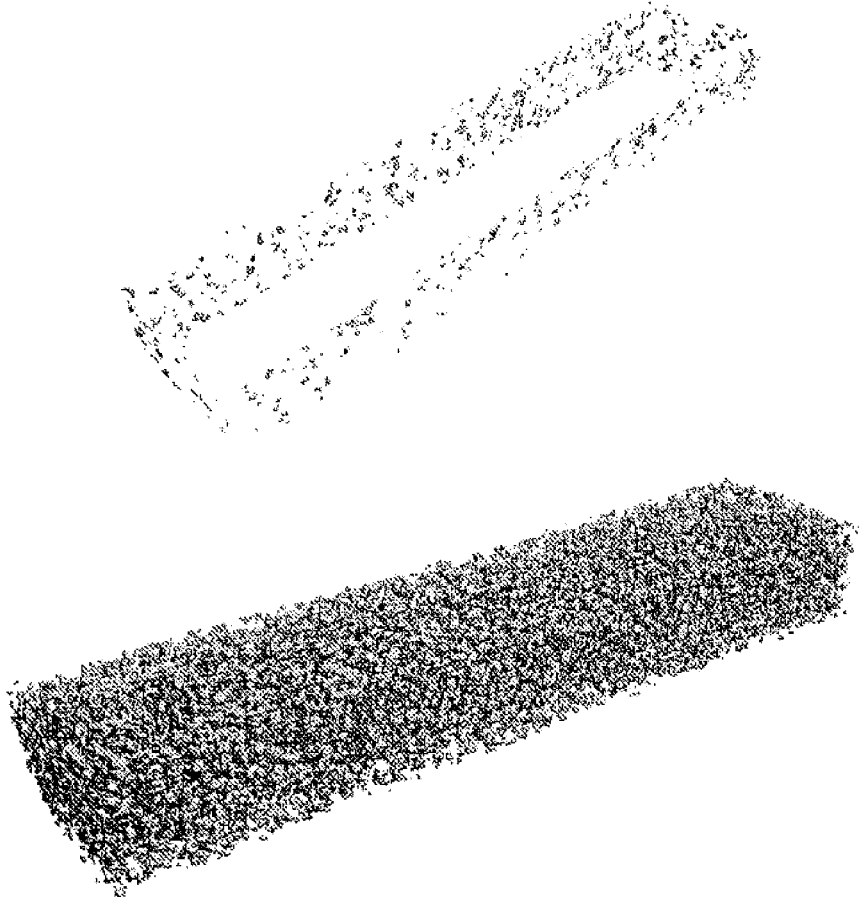
FIGURE 86

BIOACTIVE COMPOSITES OF POLYMER AND GLASS AND METHOD FOR MAKING SAME

CROSS-REFERENCE TO RELATED APPLICATIONS

The present application is a continuation of U.S. patent application Ser. No. 12/577,835, filed Oct. 13, 2009, which claims the benefit of the filing date of U.S. Provisional Patent Application No. 61/141,453, filed Dec. 30, 2008, the disclosures of which are incorporated herein by reference.

BACKGROUND OF THE INVENTION

Biomaterials have been used as implants in the field of spine, orthopaedics and dentistry including trauma, fracture repair, reconstructive surgery and alveolar ridge reconstruction, for over a century. Although metal implants have been the predominant implants of choice for these types of load-bearing applications, additional ceramics and nonresorbable polymeric materials have been employed within the last twenty-five years due to their biocompatibility and physical properties.

Polyetheretherketone (PEEK) is a biomaterial often used in medical implants. For example, PEEK can be molded into preselected shapes that possess desirable load-bearing properties. PEEK is a thermoplastic with excellent mechanical properties, including a Young's modulus of about 3.6 GPa and a tensile strength of about 100 MPa. PEEK is semi-crystalline, melts at about 340° C., and is resistant to thermal degradation. Such thermoplastic materials, however, are not bioactive, osteoproductive, or osteoconductive.

Conventional processes do not effectively provide a material or a method of making the material which combines a biocompatible polymer such as PEEK with a bioactive glass having a particle size larger than one micron. Furthermore, these processes do not incorporate a material or disclose a method of making a bioactive implant material which combines PEEK and bioactive glass of various particle sizes and which has the appropriate structural and mechanical properties to withstand the stresses necessary for use in spinal and orthopaedic implants.

A combination of polymers including PEEK and Combeite glass-ceramic, a bioactive glass, has generally been described in U.S. Pat. No. 5,681,872; U.S. Pat. No. 5,914,356; and U.S. Pat. No. 6,987,136, each of which is assigned to the assignee of the present invention and is incorporated in this document by reference in its entirety. It has been discovered, however, that conventional methods of combining polyaryletherketones, such as PEEK, and bioactive glasses, such as Combeite bioactive glass-ceramic, for example, combination using a screw extruder, results in a reaction between the PEEK and the Combeite glass-ceramic that forms a material having properties which inhibit extruder functioning. In some instances, the reaction makes combining bioactive materials, such as glass, ceramics, and glass-ceramics, with PEEK, or similar polymers of the polyaryletherketone family, a challenge using conventional processing. Attempts to combine PEEK and a bioactive glass without the use of a screw extruder have been made. For example, International Patent Publication WO 2008/039488, which is assigned to the assignee of the present invention, discloses a method of mixing PEEK and a bioactive glass followed by a compression molding step to form an article. Although this process successfully produces a bioactive article, the homogeneity of the bioactive article, in part, relies upon the PEEK and the bioactive glass being processed in powder form so that the starting particle size of the PEEK and the particle size of the bioactive glass are closely matched. Furthermore, compression molding methods such as this disclosed are not ideal for large scale bulk material preparation.

It is desirable, therefore, to have a process that successfully employs an extruder when producing bioactive composites such as, for example, PEEK and Combeite, because the equipment is readily available and can handle high throughputs (e.g., on the order of fifty pounds per hour). Furthermore, it is desirable to have a process that yields homogenous pellets which can be re-processed or injected molded to a desired shape (unlike traditional compression molding processes that are subject to variability in homogeneity, variability in bioactive glass distribution, higher likelihood of structural imperfections, have low yields, and are limited to small net shapes). Accordingly, there is a need in the art for a method of preparing a bioactive composite in which a bioactive glass, such as 45S5 or Combeite, is mixed with a polymer to produce a homogenous bioactive composite. There is also a need in the art for a method of preparing a homogeneous bioactive composite which facilitates use of various PEEK particle sizes in combination with various bioactive glass particle sizes (in which the respective particle sizes may be mis-matched). Further, there is also a need in the art for a method for preparing a bioactive composite in large batches that can be further processed to produce shaped implants that have the appropriate mechanical properties to withstand the forces required of spinal, orthopaedic and dental implants. The present invention fulfills these needs.

BRIEF DESCRIPTION OF SEVERAL VIEWS OF THE DRAWINGS

The invention is best understood from the following detailed description when read in connection with the accompanying figures. It is emphasized that, according to common practice, the various features of the figures are not to scale. On the contrary, the dimensions of the various features are arbitrarily expanded or reduced for clarity. Included are the following figures:

FIGS. 3a and 3b provide side views illustrating the cervical implant 10 with and without a lordotic angle, respectively.

FIGS. 5a and 5b provide an isometric and top view, respectively, of another embodiment of a cervical implant 10a.

FIG. 9 provides an isometric view of an embodiment of a connector accessory 110 that may be used in connection with cervical implant 10 or 10a.

FIG. 10 provides an isometric view of another embodiment of a spacer accessory 120 that may be used in connection with cervical implant 10 or 10a.

FIG. 11 provides an isometric view of the connector accessory 110 and the spacer accessory 120 that may be used to mate two cervical implants 10 or 10a.

FIG. 22b provides a top and bottom planar view of implant x1.

FIG. 31a provides an isometric view of another embodiment of the implant insertion tool 350 featuring a threaded tip that can be advanced via rotation of the advancer 380 or rotatable end knob 380a.

FIG. 36 provides a planar view of one embodiment of forceps 440.

FIG. 37 provides a detailed, planar view of the forceps 440 engaging cervical implant 10.

FIG. 38 provides an isometric view of the forceps 440 engaging the cervical implant 10.

FIG. 39 provides a detailed, isometric view of the forceps 440 engaging the cervical implant 10.

FIG. 43 provides a detailed isometric view of an embodiment of the insertion tool 500 of the present invention engaging the cervical implant 10.

FIG. 44 provides an isometric view of the insertion tool 500 and one embodiment of the impactor hammer 510 of the present invention.

FIG. 45 provides an isometric view of the insertion tool 500 and the cervical implant 10 being inserted between two vertebral bodies.

FIG. 46 provides a side view of the insertion tool 500 and the cervical implant 10 being inserted between two vertebral bodies.

FIGS. 47a through 47c provide a front view of the insertion tool 500 being used to adjust the position of the implant 10 between the two vertebral bodies.

FIG. 48 provides isometric views of one embodiment of trial implant tools of the present invention.

FIG. 49 provides a detailed, isometric view of the trial implant of FIG. 48.

FIGS. 65b and 65c are in the shape of rings.

FIG. 86 depicts microCT images and 3-D reconstructions of an exemplary embodiment of the present invention comprising 80% PEEK and 20% Combeite glass-ceramic (90 to 150 μm).

DETAILED DESCRIPTION OF THE INVENTION

Figure 1:
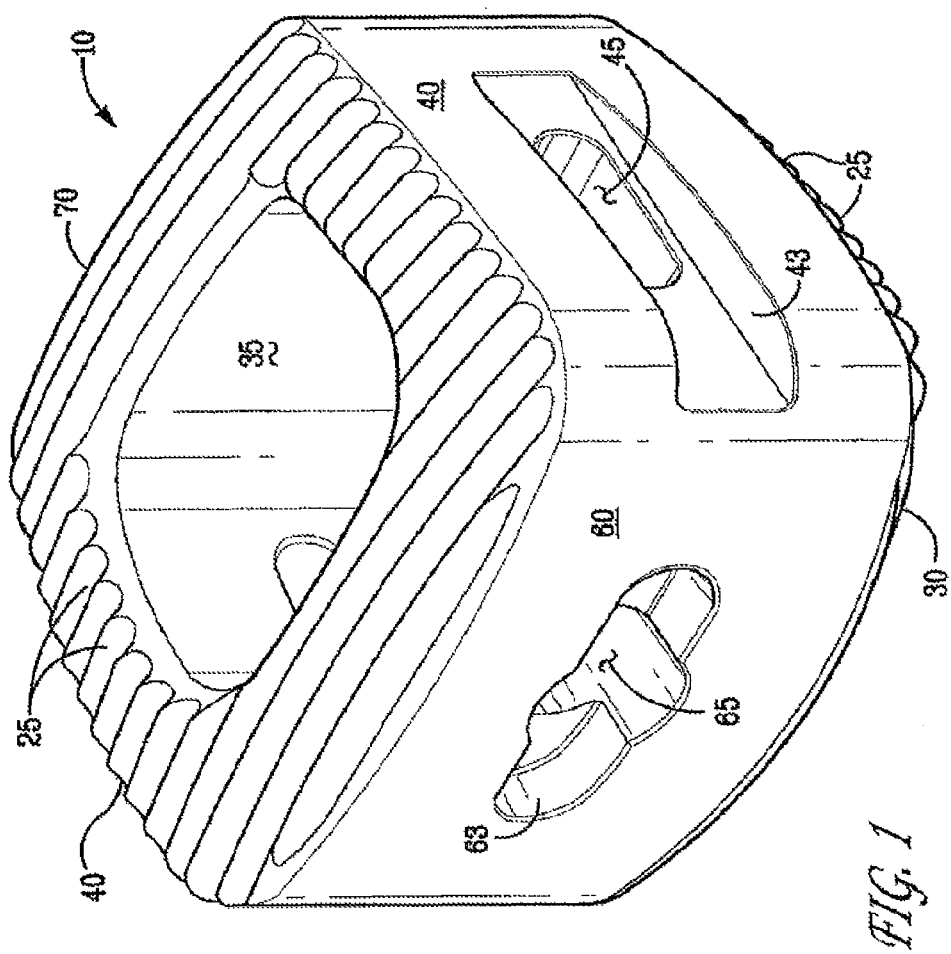
FIG. 1 provides an isometric view of one embodiment of a cervical implant 10.

The present invention relates generally to bioactive composites of biocompatible polymer and glass and, more particularly, to implants. The present invention also relates to methods of manufacturing bioactive composites. The present invention further relates to methods of repairing or fusing bone; methods of replacing diseased or dysfunctional joints; methods of implanting bioactive composites of polymer and glass; and methods of facilitating mechanical interlock of composite implants with bone.

The present invention provides bioactive composites, and methods for making the bioactive composites, comprising bioactive and biocompatible implant materials for formulation of shaped bodies capable of bonding and mechanically interlocking to bone. The present invention also provides bioactive composites and methods to produce shaped implants that have the appropriate mechanical properties to withstand the forces required of spinal, orthopaedic and dental implants. The present invention further provides methods for preparing bioactive composites comprising a biocompatible polymer such as, for example, polyetheretherketone (PEEK), and a bioactive glass such as, for example, Combeite glass-ceramic. The present invention also provides for shaped bodies prepared from these materials to be used in a wide array of clinical applications.

In one embodiment, the present invention provides bioactive composites that include a biocompatible polymer in combination with a bioactive glass. As used herein, the term "biocompatible polymer" refers to a polymer that, when introduced into a living system, will be compatible with living tissue or the living system (e.g., by not being substantially toxic, injurious, or not causing immunological rejection). The biocompatible polymer may be selected such that it will function to reinforce the composite in order to, for example, increase the load bearing capability of the composite.

The biocompatible polymer used in the present invention is preferably a synthetic polymer. Examples of synthetic biocompatible polymers that are suitable for use in the present invention alone or in combination include, polymethylmethacrylate, polyaryletherketones (PAEKs), including polyetheretherketone (PEEK) and polyaryletherketoneetherketoneketone (PEKEKK), polyurethane, poly(L-lactide), poly(D,L-lactide), poly(L-co-D,L-lactide), polyglycolide, poly(lactide-co-glycolide), poly(hydroxylbutyrate), poly(hydroxyvalerate), tyrosine-derived polycarbonate, polyanhydride, polyorthoester, polyphosphazene, poly(dioxanone), poly($\epsilon$-caprolactone), and polyglyconate. Other similar polymers known in the art may be used and various combinations of polymers may be included in the composition to adjust the properties of the composition as desired. In preferred embodiments of the present invention, polymers in the PAEK family, including PEEK are the preferred biocompatible polymers.

The molecular weight of the biocompatible polymer may vary depending on the desired application. Preferred molecular weights of the polymers include from about 50,000 to about 750,000, from about 50,000 to about 500,000 and from about 70,000 to about 400,000 Daltons. In some embodiments where PEEK is used as the biocompatible polymer, the PEEK may be high molecular weight PEEK (i.e., 110,000-120,000 $M_n$), medium molecular weight PEEK (i.e., 100,000-110,000 $M_n$) or low molecular weight PEEK (i.e., 70,000-100,000 $M_n$). For instance, high molecular weight PEEK may be preferred for processes in which the glass load is low; whereas low molecular weight PEEK may be more preferred for processes in which the glass load is high. Low molecular weight PEEK may also be preferred for applications where the final molded implant possesses intricate design features or requires repeated re-melting steps. Alternatively, the biocompatible polymer itself may be a medium molecular weight PEEK or a composite of high and low molecular weight PEEK. The preferred biocompatible polymer may have a melt flow rate (ASTM D1238) from 1 g/10 min to 60 g/10 min. In certain embodiments, the polymer has a high molecular weight and the melt flow rate is from 2 to 5 g/10 min. In other embodiments, the polymer has a low molecular weight and the melt flow rate is 18-50 g/10 min. Non-limiting representative examples of PEEK polymers include Invibio®'s PEEK-OPTIMA® LT1 (high molecular weight), PEEK-OPTIMA® LT2 (medium molecular weight), PEEK-OPTIMA® LT3 (low molecular weight), MOTIS™, PEEK-CLASSIX® (Invibio, Ltd., Lancashire, United Kingdom; Invibio, Inc., West Conshohocken, Pa.), PEEK polymers from Evonik Degussa Corporation (Parsippany, N.J.), PEEK Altera™ from Medshape Solutions, Inc (Atlanta, Ga.), and Zeniva™ from Solvay Advanced Polymers, LLC (Alpharetta, Ga.).

The biocompatible polymer component of the present invention can be used in a wide range of particle sizes. For instance, the biocompatible polymer may have a particle size of from about 4 µm to about 4,000 µm. In a preferred embodiment of the present invention, the particle size ranges from about 1000 µm to about 4,000 µm. In such embodiments, the biocompatible polymer is typically obtained in granular or pellet form from a commercial supplier before it is mixed with the bioactive glass in accordance with the methods of the present invention.

Bioactive glasses and glass-ceramics are characterized by their ability to form a direct bond with bone. A material based on the PEEK polymer, or similar types of polymers of the PEEK family that include the bone-bonding properties of a bioactive glass, would be desirable. By incorporating bioactive glass into the polymer matrix, a composite material is formed which when implanted elicits a bioactive reaction and leads to bone formation and direct bone apposition onto the surface of the implant, usually without intervening fibrous tissue. It has been particularly determined that bioactive glass in the size range of from about 50 µm to about 300 µm, and, more particularly, from about 90 µm to about 150 µm facilitates mechanical interlock of the composite material with bone, such that bone grows into the surface of the bioactive composite at the site of the bioactive particle.

The bioactive glass used in the present invention may be any alkali-containing ceramic (glass, glass-ceramic, or crystalline) material that reacts as it comes in contact with physiological fluids including, but not limited to, blood and serum, which leads to bone formation. In preferred embodiments, the bioactive glasses, when placed in physiologic fluids, form an apatite layer on their surface. As used herein, "bioactive" relates to the chemical formation of a calcium phosphate layer (amorphous, partially crystalline, or crystalline) via ion exchange between surrounding fluid and the composite material. Bioactive also describes materials that, when subjected to intracorporeal implantation, elicit a reaction. Such a reaction leads to bone formation, attachment into or adjacent to the implant, and/or bone formation or apposition directly to the implant, usually without intervening fibrous tissue.

Preferably, the bioactive glass component of the present invention comprises regions of Combeite crystallite morphology. Such bioactive glass is referred to in this document as "Combeite glass-ceramic". Examples of preferred bioactive glasses suitable for use in the present invention are described in U.S. Pat. No. 5,914,356 and U.S. Pat. No. 5,681,872, each of which is incorporated by reference in this document in its entirety. Other suitable bioactive materials include 45S5 glass and compositions comprising calcium-phosphorous-sodium silicate and calcium-phosphorous silicate. Further bioactive glass compositions that may be suitable for use in the present invention are described in U.S. Pat. No. 6,709,744, incorporated in this document by reference. Other suitable bioactive glasses include borosilicate, silica, and Wollastonite. Suitable bioactive glasses include, but are not limited to, silica-, borate-, and phosphate-containing materials. It is understood that some non-alkali-containing bioactive glass materials are within the spirit of the invention. Bioactive glasses, as defined in this document, do not include calcium phosphate materials, for example, hydroxyapatite and tri-calcium phosphate. However, in addition to bioactive glass, the composition of the invention may additionally include other agents such as calcium phosphate materials.

In preferred embodiments of the present invention, the bioactive glass is Combeite glass-ceramic (also referred to as "Combeite"). Combeite is a mineral having the chemical composition $Na_4Ca_3Si_6O_{16}(OH)_2$. It has been found that the use of bioactive glass in restorative compositions, which bioactive glasses include Combeite crystallites in a glass-ceramic structure (hence, Combeite glass-ceramic), in accordance with the present invention gives rise to superior spinal, orthopaedic and dental restorations.

It is preferred that the Combeite glass-ceramic particles which form some or all of the bioactive glass component of the present invention comprise at least about 2% by volume of Combeite crystallites. Combeite glass-ceramic particles containing higher percentages of crystallites are more preferred and volume percentage from about 5% to about 50% of crystallites are particularly desired. It will be appreciated that the Combeite glass-ceramic particles of the present invention are heterogeneous in that they comprise a glassy, amorphous structure having crystallites or regions of Combeite crystallinity dispersed throughout the material.

It is preferred that the heterogeneous particles of Combeite glass-ceramic have an average particle size from about 1 μm to about 500 μm. In some embodiments of the present invention, the Combeite glass-ceramic has an average particle size of less than about 300 μm. In other embodiments of the present invention, the Combeite glass-ceramic has an average particle size of less than about 150 μm. In still other embodiments of the present invention, the Combeite glass-ceramic has an average particle size of less than about 53 μm.

Several particular Combeite glass-ceramic average particle size ranges have been found to be preferred when practiced with the present invention. The first range is less than or equal to about 53 μm. The next average particle size range is less than or equal to about 90 μm. The third average particle size range is from about 90 μm to about 150 μm. The fourth average particle size range is less than or equal to about 150 μm. It is envisioned that, in certain embodiments of the present invention, the bioactive particles are nanoparticulate. It is also contemplated that a mix of bioactive particles of differing average particle size may be used.

Methods of determining particle sizes are known in the art. Some methods include passing the particles through several sieves to determine general particle size ranges. Other methods include laser light scattering, and still others are known to persons skilled in the art. Determination of particle size is conveniently accomplished by sieving and such may be used here. Particle size may also be determined via SEM image analysis. It will be appreciated that recitation of averages or size ranges is not meant to exclude every particle with a slightly higher or lower dimension. Rather, sizes of particles are defined practically and in the context of this invention.

In accordance with some preferred embodiments, blends of Combeite glass-ceramics may be useful as the bioactive glass component of the present invention. Thus, a number of different Combeite glass-ceramics can be prepared having different properties, such as Combeite crystallite size, percentage of Combeite crystallites, particle sizes of the Combeite glass-ceramic and the like. It is also preferred in some cases to admix Combeite glass-ceramic in accordance with the present invention with other agents which are consistent with the objectives to be obtained. Thus, a wide variety of such other agents may be so employed so long as composition of the invention comprises bioactive glass equaling at least about 5% by weight of the composition. The other agent composition may also include radiopacifying agents such as those known in the art.

In certain embodiments, the bioactive glass component may be in the form of fibers, whiskers or strands. It is preferred that the diameters of these fibers and strands be from about 1 μm to about 500 μm.

In some embodiments, the bioactive glass comprises at least one alkali metal such as, for example, lithium, sodium, potassium, rubidium, cesium, francium, or combinations of these metals. In other embodiments, however, the bioactive glass has little to no alkali metal. For example, in certain embodiments, the bioactive glass has 30% or less of alkali metal. In other embodiments, the bioactive glass has 25% or less of alkali metal. In yet other embodiments, the bioactive glass has 20% or less of alkali metal. In yet other embodiments, the bioactive glass has 15% or less of alkali metal. In other embodiments, the bioactive glass has 10% or less of alkali metal. In still other embodiments, the bioactive glass has 5% or less of alkali metal. In yet other embodiments, the bioactive glass has substantially no alkali metal. Without intending to be bound by any particular theory, it is believed that the presence of certain metals may catalyze further polymerization of the biocompatible polymer such as, for example, PEEK, thereby (1) increasing its molecular weight and/or (2) increasing its degree of cross-linking/cross-link density. Either event increases the viscosity of the polymer and may seize up the equipment used to process the composite material. As such, a bioactive glass with a low percentage of alkali metal may be utilized to prevent equipment failure and/or to allow a high percentage of bioactive glass to be utilized.

In exemplary embodiments of the present invention, the bioactive glass has osteoproductive properties. As used in this document, "osteoproductive" refers to an ability to allow osteoblasts to proliferate, allowing bone to regenerate. "Osteoproductive" may also be defined as conducive to a process in which a bioactive surface is colonized by osteogenic stem cells and which results in more rapid filling of defects than that produced by merely osteoconductive materials. Combeite glass-ceramic is an example of an osteoproductive, bioactive material.

According to one embodiment of the present invention, the compounded composite material may comprise up to about 50% of the bioactive glass. In certain embodiments, the bioactive glass is present in an amount of about 5 to 50% by weight of the compounded composite material. In other embodiments, the bioactive glass is present in an amount of about 15 to 30% by weight of the compounded composite material. In yet other embodiments, the bioactive glass is present in an amount of about 20 to 30% by weight of the compounded composite material. In embodiments in which a low molecular weight biocompatible polymer is used, bioactive glass may be present in higher weight percentages, such as 60% by weight of the compounded composite material.

In some embodiments of the present invention, a coupling agent is added to the mixture of the biocompatible polymer and the bioactive glass. The coupling agent acts as a bonding agent between the biocompatible polymer and the bioactive glass which translates into increased tensile/flexural strength of the bioactive composite. Non-limiting examples of coupling agents suitable for use in the present invention include, for example, silane, titanium-based and zirconium-based coupling agents, specifically, organotitanate, multifunctional amine compounds such as 4-aminophenyl sulfone, azo compounds such as 4-cyanovaleric acid, and combinations thereof. The preferred coupling agent is one that includes multifunctional groups that are capable of chemically bonding with a functional group of the biocompatible polymer and binding the bioactive glass. The bioactive glass may be coated with the coupling agent prior to being combined/mixed with the biocompatible polymer. Alternatively, both the bioactive glass and biocompatible polymer may be individually coated with the coupling agent before being combined.

Figure 54:
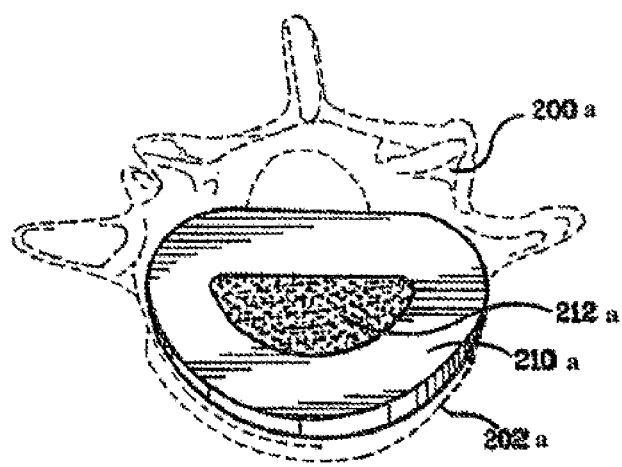
FIG. 54 is an example of another embodiment of a shaped body in the form of a vertebral body spinal implant according to the present invention shown with a graft material in the center of the implant.

Also in accordance with the present invention, at least one other agent may be added to the mixture of the biocompatible polymer and bioactive glass. Such agents can comprise, at least partially, reinforcing fibers. Non-limiting examples of other agents include carbon, glass, radiopaque material, barium glass, resorbable material, strontium, strontium nitrate, strontium-calcium-zinc-silicate glasses, silver, calcium apatite, calcium silicate or mixtures of these materials. In certain aspects of the invention, the other agent is barium sulfate, barium-boroaluminosilicate (BBAS) glass, silica or e-glass fibers. In some embodiments, the other agents include radiopaque markers situated in predetermined locations within the shaped implant to aid in visualizing the implant once in the body. For example, FIGS. 5a and 5b show titanium alloy (Ti-6Al-4V ELI) markers incorporated into the composite shaped body. In certain embodiments, the other agent may comprise calcium phosphate having macro-, meso-, and microporosity. More preferably, the porosity of the calcium phosphate is interconnected. The preparation of preferred forms of calcium phosphate for use in the present invention is described in U.S. Pat. No. 6,383,519 and U.S. Pat. No. 6,521,246, incorporated into this application by reference in their entireties. An exemplary calcium phosphate product is Vitoss® Bone Graft Substitute (available from Orthovita, Inc. of Malvern, Pa.). The at least one other agent may be incorporated within the bioactive composite, or in the case of a shaped implant be used to fill cavities of the implant. For instance, when used with a shaped spinal implant, the other agent may be present within the center cavity of the implant to facilitate fusion of the adjacent vertebral bodies (FIG. 54).

In addition to other agents, bone augmentation materials or bone cements may be used in conjunction with the bioactive composite in applications where additional reinforcement is required. For instance, in certain bone fractures it may first be required that certain portions of the fracture be stabilized with a bone augmentation material prior to placing the bioactive composite implant of the present invention. Alternatively, in certain spine fusion procedures, it may first be desired to prophylactically treat the adjacent vertebrae prior to placing the bioactive spinal implant of the present invention in the disc space between the two vertebrae, if the bone stock appears weakened due to trauma or disease such as osteoporosis. An exemplary bone augmentation product is Cortoss® Bone Augmentation Material (available from Orthovita, Inc. of Malvern, Pa.).

In a preferred embodiment of the present invention, a bioactive composite is formed upon combining a biocompatible polymer with a bioactive glass as described in the present invention. The biocompatible polymer preferably has a particle size range from 400 μm to 4,000 μm and comprises from about 60-90% by weight of the composite composition and the bioactive glass has a particle size range of from about 1 μm to about 500 μm and comprises from about 10-40% by weight of the composite composition. The use of low molecular weight PEEK has been determined to facilitate processing of the composite.

It has been found that the use of low molecular weight PEEK and particularly low molecular weight PEEK having a large particle size (e.g., particles from 400 μm to 4,000 μm) as used in the preferred embodiment of the present invention unexpectedly allows processing using extrusion, enables homogeneity of the composite to be achieved even when the size of the PEEK particles is not evenly matched to the size of the bioactive glass particles, and improves structural fidelity. Furthermore, the use of low molecular weight PEEK particles in conjunction with bioactive glass as described herein, results in a novel bioactive, bone-bonding composition having suitable physical properties for use in a variety of spinal, orthopaedics and dental surgical procedures.

The present invention also provides a method of preparing a bioactive composite, the method comprising the steps of: a) adding to a compounder a biocompatible polymer and a bioactive glass to form an extrudable composite material, wherein i. the bioactive glass has a particle size of from about 1 μm to about 500 μm; ii. the bioactive glass is present in the extrudable composite material in an amount of from about 5 to about 50% by weight; and b) applying energy (e.g., heat, vibrational, radiofrequency, microwave, etc., or combinations thereof) to the extrudable composite material to mix the biocompatible polymer and the bioactive glass; and c) extruding a bioactive composite. The present invention also provides a method of preparing a bioactive composite, the method comprising the steps of: a) adding to a compounder a biocompatible polymer; b) applying energy (e.g., heat, vibrational, radiofrequency, microwave, etc., or combinations thereof) to the biocompatible polymer for a period of time and temperature to form a melted polymer; c) adding to the melted polymer a bioactive glass to form a composite material, wherein i. the bioactive glass has a particle size range of from about 1 μm to about 500 μm; ii. the bioactive glass is present in the extrudable composite material in an amount of from about 5 to about 50% by weight; and d) allowing the composite material to travel down the length of the heated barrel for additional time to melt mix the biocompatible polymer and the bioactive glass; and e) extruding a homogenous bioactive composite. The bioactive composite can be extruded in the form of films, sheets, rods, and the like, though preferably the bioactive composite is extruded and pelletized, such that the pellets can then be re-processed to form the desired shape. In one embodiment, the bioactive composite is extruded into pellets (e.g., homogeneous bioactive composite pellets) in the size range from about 400 μm to about 4000 μm. In another embodiment, the bioactive composite may be extruded into pellets in the size range of about 1000 μm to about 4000 μm.

It should be noted that the step of adding the bioactive glass to the polymer can be performed at various stages of the compounding process. For instance, the bioactive glass can be blended with the polymer prior to adding the mixture to the compounder. The bioactive glass can also be added using a second downstream hopper once the polymer has traveled an adequate distance along the length of the barrel such that it is sufficiently softened or such that it is in a completely melted state. Most preferably, the bioactive glass is added to the melted polymer at a point downstream such that the polymer-glass mixture only travels the distance of the barrel that is necessary to produce a homogenous mixture prior to extruding. It will be appreciated that there are numerous types of compounders known in the art with varying barrel diameters, barrel lengths, and screw types. Preferably, the method of the present invention utilizes a twin screw extruder and the bioactive glass is added to the polymer once the polymer is in a completely melted state, typically after it has traveled at least 50% of the length of the barrel. However it should be appreciated that the method of the present invention can be utilized with any combination of barrel diameter, barrel length, or screw type by modifying the distance downstream that the bioactive glass is added to the polymer.

In other embodiments, the biocompatible polymer and the bioactive glass (as well as other components, if present) may be dry mixed for a period of time and under conditions sufficient to achieve substantial homogeneity of the mixture. As used herein, the term "dry mixed" refers to mixing the components in a dry state, i.e., in the absence of added liquid water or organic solvent. The dry mixing of the bioactive glass with the biocompatible polymer granules or pellets may be accomplished using any methods known in the art per se, including milling, spinning, tumbling, sonication, vibrating, or shaking. In one embodiment, the mixture is tumbled on rollers for about one to about two hours. As used herein, the terms "homogeneity" and "homogeneous" describe a composition that is substantially uniform in structure and/or composition throughout. The term "substantially homogeneous" is to be understood within the context of the invention and is not to be taken as an absolute.

In one embodiment, the extrudable composite material is formed by adding the polymer and bioactive glass to a compounder such as, for example, a single screw or a twin screw extruder, where it is melt mixed and extruded to form a bioactive composite. It is a feature of the present invention that the biocompatible polymer is melt mixed with the bioactive glass. As used herein, the term "melt mixed" or "compounded" refers to mixing the components using heat and shear. For example, the biocompatible polymer may be compounded by placing in a screw extruder, melting via heat and then adding the bioactive glass to the extruder after the biocompatible polymer is melted. The biocompatible polymer may also be dry mixed with the bioactive glass as detailed above to form an extrudable composite material. In a preferred embodiment, the biocompatible polymer and bioactive glass are mixed without the use of liquids/fluids such as water or organic solvents including ethanol. In other embodiments, the use of a solvent is prohibited in the sense that the solvent can cause irreparable damage to the extruder. In this manner, the present invention differs from that of International Patent Publication WO 2008/039488, assigned to the assignee of the present invention, because International Patent Publication WO 2008/039488 focuses on the use of a solvent to mix biocompatible polymer and bioactive glass of similar particle size. By eliminating the use of a solvent, the bioactive glass retains its inherent bioactivity and is not pre-leached. Various methods of compounding the material can be utilized to increase the percentage of bioactive glass and/or allow for subsequent re-heating of the composite material. For example, using a single screw extruder reduces the shear forces. Reducing the contact time between the bioactive glass and polymer in the compounder will also allow for a greater percentage of bioactive glass to be incorporated, for example, by adding the bioactive glass at a point downstream in the barrel once the polymer is already melted. It is preferable to use a twin screw compounder to produce the bioactive composite of the present invention, due to increased homogeneity of the resultant composite. Most preferably, the bioactive glass is added to the twin screw extruder using a second hopper at a point downstream in the barrel where the polymer is already in a melted state. The second hopper is positioned along the length of the barrel such that the bioactive glass travels the shortest distance possible in contact with the melted polymer to produce a homogenously mixed composite, generally less than 50% of the length of the barrel. One non-limiting example of a compounder that may be used to compound the biocompatible polymer and bioactive glass components of the present invention is the Leistritz 40 mm twin screw extruder (Model ZSE 40HP).

In the extruder the composition is first melt mixed using, for example, twin high shear screws and formed into a continuous strand of bioactive composite which is further pelletized into molding granules (pellets). The melt mix typically promotes uniformity in the dispersion of the PEEK and the bioactive glass and facilitates the use of a various sizes of particles (e.g., PEEK particles may differ in size from the size of the bioactive glass particles) while still producing a homogeneous composite. The temperature needed to melt mix the biocompatible polymer and the bioactive glass will typically depend on the melting temperature of the biocompatible polymer being used. For example, when the biocompatible polymer is PEEK, generally the melt mixing temperature will be at least 340° C., typically from about 340 to about 400° C. Under this condition, the PEEK is sufficiently fluidized in the composition and uniformly coats the bioactive glass component.

The amount of torque required to extrude the melt mix from the compounder will depend on a number of factors such as, for example, the inherent viscosity of the biocompatible polymer, the RPMs (revolutions per minute), the inherent capability of the extruder, and the kind and amount of the bioactive glass. For example, Table 1 demonstrates the effect of such factors on torque for a Theysohn TSK 21 mm Twin Screw Extruder (Theysohn Extruders, Korneuburg, Austria) at a barrel temperature of 380° C. It can be appreciated that the torque and RPMs required for low molecular weight PEEK are relatively unaffected by the percentage of glass filler. The torque and RPMs required to extrude composites of high molecular weight increase with increasing amounts of bioactive glass. This effect is more pronounced with smaller sized bioactive glass particles.

TABLE 1

| Grade of PEEK | % PEEK/<br>% Combeite | Torque<br>(Nm) | RPMs |
| --- | --- | --- | --- |
| Low Molecular | 100/0 | 36 | 256 |
| Weight* w/<53 μm | 85/15 | 37.44 | 260 |
| glass | 70/30 | 38.90 | 268 |
| High Molecular | 100/0 | 50.4 | 250 |
| Weight* w/<53 μm | 85/15 | 52.6 | 300 |
| glass | 80/20 | 54.72 | 350 |
|  | 70/30 | 51.8 | 400 |
| High Molecular | 100/0 | 50.4 | 250 |
| Weight Medical | 85/15 | 55.44 | 300 |
| Grade** | 80/20 | 57.6 | 350 |
| w/<53 μm glass | 70/30 | 54.72 | 400 |
| High Molecular | 100/0 | 50.4 | 250 |
| Weight* w/90-150 μm | 85/15 | 53.3 | 284 |
| glass | 80/20 | 50.4 | 317 |
|  | 70/30 | 49.0 | 340 |
| High Molecular | 100/0 | 50.4 | 250 |
| Weight* w/silane- | 85/15 | 48.24 | 285 |
| treated <53 μm | 80/20 | 46.8 | 317 |
| glass | 70/30 | 51.84 | 339 |

*= obtained from Victrex, West Conshohocken, PA
**= obtained from Invibio Biomaterial Solutions, West Conshohocken, PA The pellets/granules of bioactive composite are ready for injection molding either immediately after the extrusion process or after a period of storage. The resultant extrudate is a bioactive composite that can be the final molded article, such as in the case of an injection molded article or an extruded tube, sheet or coating, or can be chopped into molding pellets/granules for subsequent melt processing into the article desired. One non-limiting example of a molder that may be employed to mold the composite pellets of the present invention is the Cincinnati Roboshot S2000i B 55 ton molder.

The bioactive composite can be molded using conventional molding techniques, including compression and injection molding. In addition, conventional machining techniques can be used to form an integral shaped bioactive implant body, such as those exemplary embodiments depicted in the figures. The bioactive composite may be injection molded into a shaped implant body. Preferably, the bioactive composite may be molded in a near net shape such that after further machining, a shaped body for implantation is prepared. For example, the bioactive composite may be molded to form a generic shape, for example a cylinder, block, or ovoid, which is then machined to a pre-selected implant shape.

In a typical injection molding process of thermoplastics, the bioactive composite pellets are heated to a temperature at which the composite becomes molten and the molten composite is injected into a mold followed by cooling to room temperature or below. Alternatively, the bioactive composite pellets can be compression molded to form the implant body. In this embodiment, a mold is filled with the composite pellets and a pressure of, for example, about 1 to about 400 MPa is applied to form a bioactive implant or a generic shape suitable for further machining. Heat sufficient to melt at least one component of the composite can also be used. In addition to using heat to melt at least one component of the composite, vibrational, radiofrequency, or microwave energy, or combinations of these energies, can be used to melt at least one component of the composite.

In another embodiment of the present invention, the bioactive polymer and the bioactive glass can be added directly to an injection molder without first performing a compounding step. In such embodiment, the method of the invention comprises the steps of: adding in a solid state the biocompatible polymer and the bioactive glass to an injection molder to form a shaped bioactive composite, wherein the bioactive glass has a particle size of from about 1 μm to about 500 μm; and the bioactive glass is present in the composite in an amount of from about 5 to about 50% by weight; applying energy to the injection molder to form a melt mix of the biocompatible polymer and the bioactive glass; and injecting the melt mix into a mold to form the shaped bioactive composite. The biocompatible polymer and the bioactive glass can be added to the injection molder pre-mixed or they can be added separately. By either method of addition, the biocompatible polymer and the bioactive glass are melt mixed in the injection molder.

Once the bioactive composite has been molded into its final form, the molded bioactive composite is preferably subjected to a finishing step to further expose the bioactive glass. Examples of finishing techniques include, for example, milling, cutting, drilling, and/or sanding of the shaped body. Additionally, exposure of the bioactive glass could be accomplished through grit blasting, plasma treatments, etching and the like. Preferred embodiments of the present invention have from about 3% to about 30% surface area exposure of bioactive glass. This amount of surface exposure allows for the bioactive reaction initiating at the glass particle to uniformly spread across the composite surface. This amount of exposed bioactive glass further lends a surface roughness to the implant which is favorable for bone bonding, and the remodeling of glass particles at the surface leads to a mechanical interlock between the implant and the newly formed bone.

Bioactive composite implant structures contemplated by the present invention include homogeneous composites prepared by mixing a biocompatible polymer such as, for example, PEEK, with bioactive glass, using the methods described. In certain embodiments, the mean particle to particle distance (e.g., mean separation of bioactive glass particles as measured from the edges of the particles) throughout the volume and along the surface is about 80 microns to about 180 microns. For example, the mean particle to particle distance in an embodiment, in which the bioactive composite is 80% by weight high molecular weight polymer and 20% by weight bioactive glass (having a particle size of 90 μm to 150 μm), may be between about 140 μm to about 180 μm. In another embodiment, in which the bioactive composite is 70% by weight low molecular weight polymer and 30% by weight bioactive glass (having a particle size of 90 μm to 150 μm) the mean particle to particle distance may be between about 100 μm to about 140 μm. Also within the scope of the present invention are bioactive composites comprising a gradient of bioactive material. For example, the gradient can vary along one or more dimensions. In another example, there may be greater concentrations of bioactive material in one or more portions of the bioactive composite as compared with other portions. Also envisioned are composites comprising layers of one or more types or concentrations of bioactive material, so long as at least one layer is in accordance with the invention. Structures prepared from such composites may have a bioactive portion of the composite at one or more specific locations, such that the bioactive material occurs where design specifications call for bone bonding. In other embodiments, structures prepared using the composites of the present invention may have bioactive materials adhered to the surface. In further embodiments of the present invention, the structures may be coated with materials described and such coatings may be useful on metallic, polymeric, or ceramic implants.

Bioactive composites and shaped bodies of the present invention made from the composites preferably demonstrate load-bearing and mechanical properties suitable for use in spinal, orthopaedic and dental procedures. Bioactive composites and shaped bodies of the present invention made from the composites also preferably demonstrate bioactivity.

A formed bioactive composite material according to the present invention can be placed in or near bone to provide load-bearing stability and micromechanical bonding to the bony material. After some time in the body, the implanted material will begin to adhere to the bone tissue interface, increasing the strength and toughness of the implant system.

It will be appreciated by those skilled in the art that the bioactive composites of the present invention may be used in a wide variety of restorative and surgical procedures including those involving bone tissues subject to large forces. One example is the repair or fusion of vertebrae of the spine. Lower back pain may oftentimes be attributed to the rupture or degeneration of lumbar intervertebral discs due to degenerative disc disease, ischemic spondylolisthesis, post laminectomy syndrome, deformative disorders, trauma, tumors and the like. This pain may result from the compression of spinal nerve roots by damaged discs between the vertebra, the collapse of the disc, and the resulting adverse effects of bearing the majority of the patient's body weight through a damaged unstable vertebral joint. To remedy this, spinal implants may be inserted between the vertebral bodies to stabilize and support the joint and facilitate fusion via bone bonding. FIGS. 1-5b, 12-22d, 53-57, 65-68 and 70 depict illustrative embodiments of spinal implants comprising bioactive and biocompatible materials. The devices of FIGS. 1-5 and 5a-5b for example, may be used in cervical fusion procedures in which an anterior surgical approach is frequently used to place the device between adjacent vertebrae; whereas the devices of FIGS. 12-22d for example, may be used in lumbar fusion procedures in which either an anterior or posterior surgical approach may be used.

Cervical Implants

The bioactive implant material may be formed into a variety of shapes for use in bone implantation, such as spinal implantation or spinal fixation devices. In one embodiment, the implant material is preferably formed into a cervical implant device.

FIGS. 1 through 4 illustrate various aspects of one embodiment of the cervical implant 10 of the present invention. Implant 10 may vary in size to accommodate differences in the patient's anatomy. The implant 10 is comprised of an anterior side 60, a posterior side 70 opposing the anterior side 60, and a pair of opposing sidewalls 40. The anterior side 60, the posterior side 70, and the sidewalls 40 are generally outwardly curved in transverse cross-section. The curved sides are convex as viewed from the outside of the implant 10. The anterior side 60, the posterior side 70, and the sidewalls 40 join at points that generally define, in transverse cross section, a trapezoid. The transverse cross-section, as used herein, is the plane perpendicular to the z-axis. As used herein, a trapezoid is a quadrilateral having two parallel sides, or any shape having the form of a trapezoid. The present invention employs geometric shapes to illustrate a preferred embodiment, but the present invention is not limited to such shape. Rather, the present invention broadly encompasses any variation in the claimed shapes within the spirit of the disclosure, including, for example, configurations in which gradually merge with adjacent sides and non-uniform shapes that vary according to the transverse or longitudinal cross section.

The implant also comprises a top surface 20 and a bottom surface 30 that is generally opposite the top surface 20. The top 20 and bottom surfaces 30 can also be convex, or outwardly curved, in the longitudinal cross-section. The curvature and shape of each side grants the implant superior anatomical compatibility. The surfaces also maximize contact with cortical bone to minimize subsidence of the implant into the endplates.

The top 20 and bottom 30 surfaces further include a plurality of projections 25, preferably wave-like or scalloped in shape (i.e., pointed apex with rounded valleys), for gripping adjacent vertebrae. The scalloped shape tooth design eliminates the stress concentration typically associated with other tooth designs and more evenly distributes the compressive physiologic loads from the bone to the implant. The projections 25 can be substantially uniform, upwardly protruding ribs. One skilled in the art would recognize these projections 25 as being substantially uniform, upwardly protruding, elongated ribs separated by concave channels. In alternative embodiments, the projections 25 are randomly disposed or, in other words, situated in various directions. These projections 25 may also be upwardly protruding spikes. The wave-like shape of the projections 25 increases the surface area of the implant for maximal vertebral contact. Further, the wave-like projections 25 provide significant resistance to expulsion and retropulsion. In certain preferred embodiments, the projections 25 have an angular pitch of between 1.75 degrees to 1.9 degrees, a minimum depth of 0.022 inches, and an internal radius of about 0.022 inches. Other dimensional sizes of the projections 25 would not depart from the present invention including upwardly protruding spikes.

FIGS. 3a and 3b illustrate two alternative embodiments of the present invention. FIG. 3a illustrates implant 10 wherein the wall of the anterior 60 side has greater height than the wall of the posterior 70 side. The implant 10 of FIG. 3a has a lordotic angle. FIG. 3b illustrates implant 10 having no lordotic angle wherein the height of the wall for the anterior 60 side is equal to the wall height of the posterior 70 side. Due to the variety of machinations that may be used to make the implants of the present invention, minute variations may exist in the height of the anterior 60 and posterior 70 sides that would not render them exactly the same height. Preferable lordotic angles fall in the range of about −20 degrees to about +20 degrees.

Figure 4:
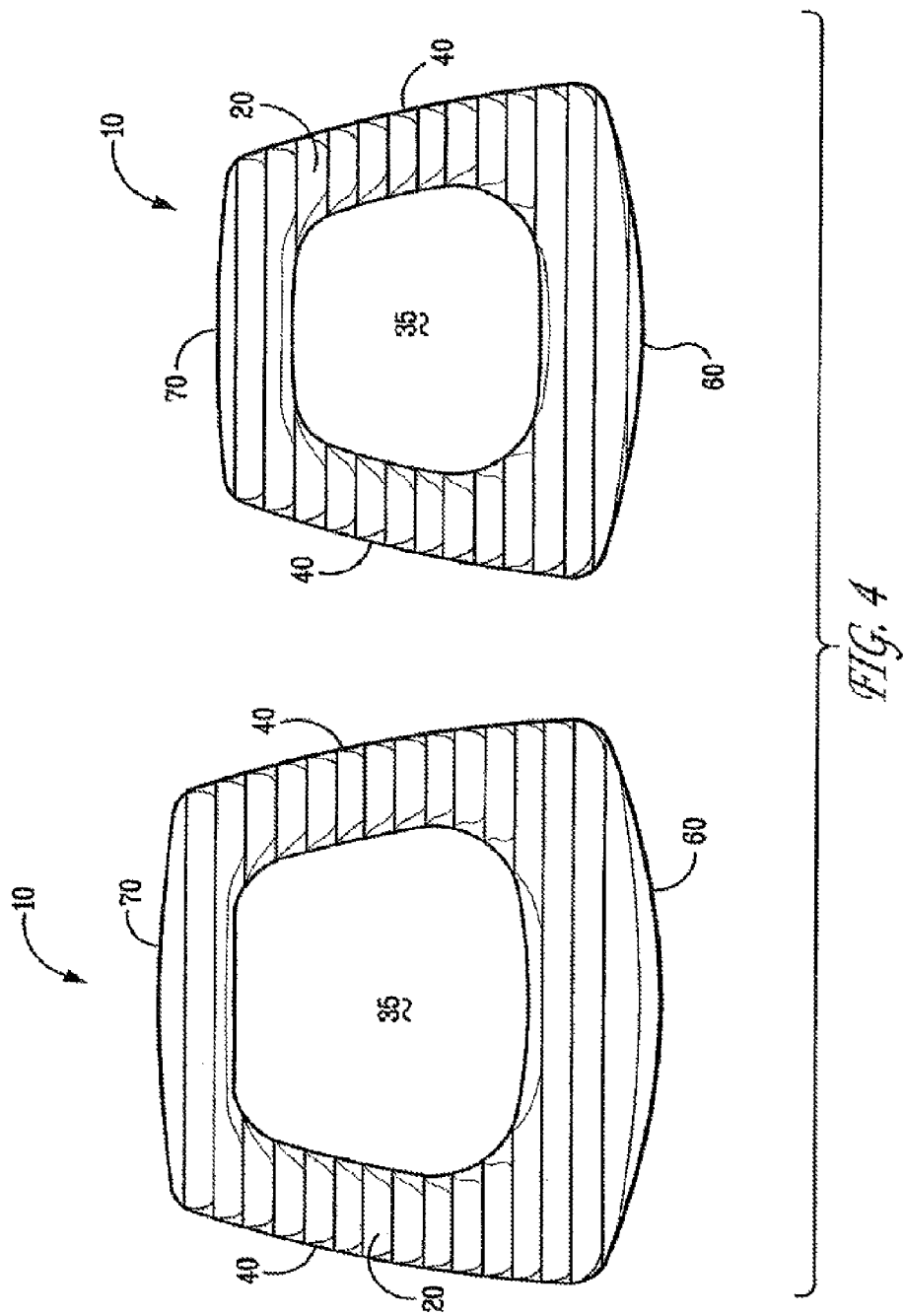
FIG. 4 provides a planar view illustrating the substantially trapezoidal shape of the top and bottom surfaces of the cervical implant 10.

In FIG. 4, the implant 10 has a trapezoidal shape defined by the sidewalls 40, anterior 60, and posterior 70 sides. This shape maximizes contact with cortical bone. In preferred embodiments, the top 20 and bottom 30 surfaces are substantially identical in size and shape. The shape also allows one skilled in the art to place graft material within a major recess 35 bordered by the sidewalls 40, anterior 60, and posterior 70 sides. This major recess 35 is formed in the body of the implant and is in communication with at least one of the top or bottom surfaces. A preferred embodiment has the major recess 35 having a through-aperture that is in communication with both top 20 and bottom 30 surfaces.

Figure 2:
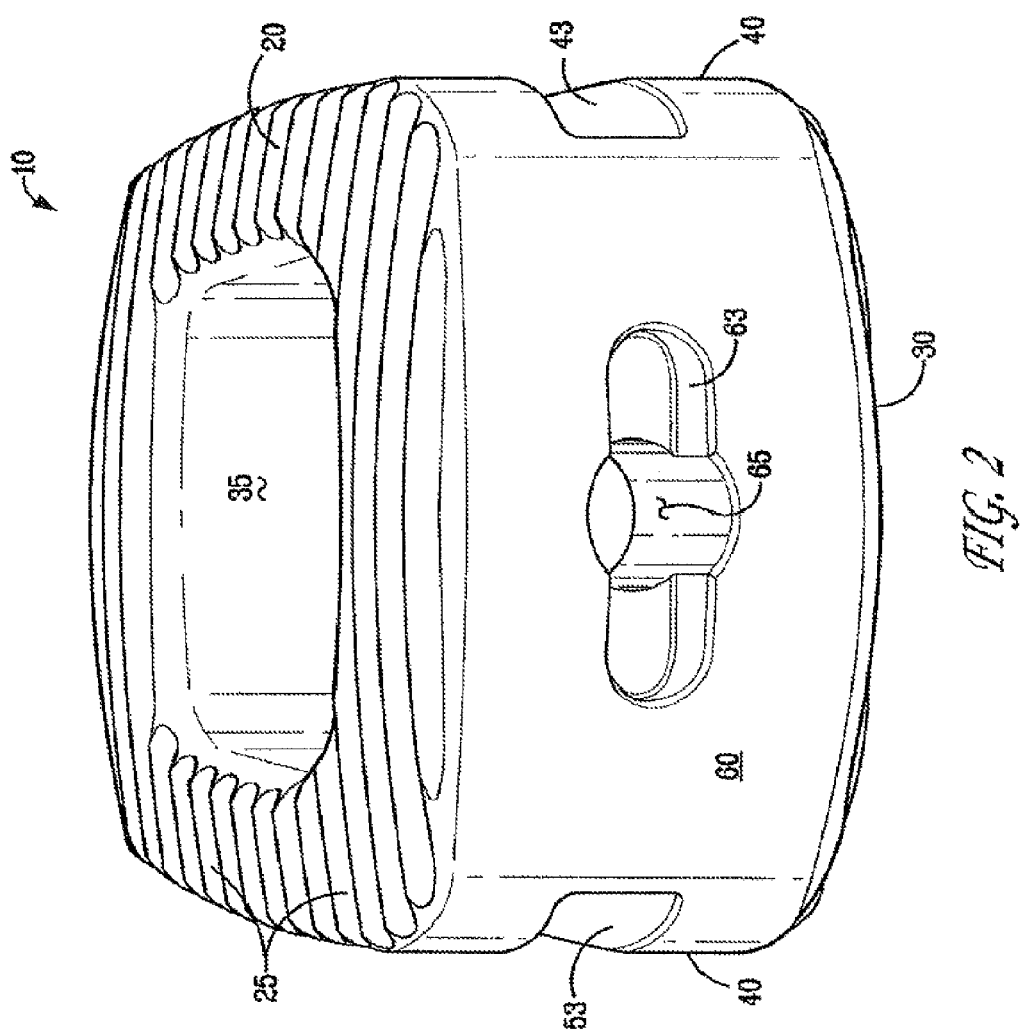
FIG. 2 provides a front view illustrating the anterior side of the cervical implant 10.
Figure 3:
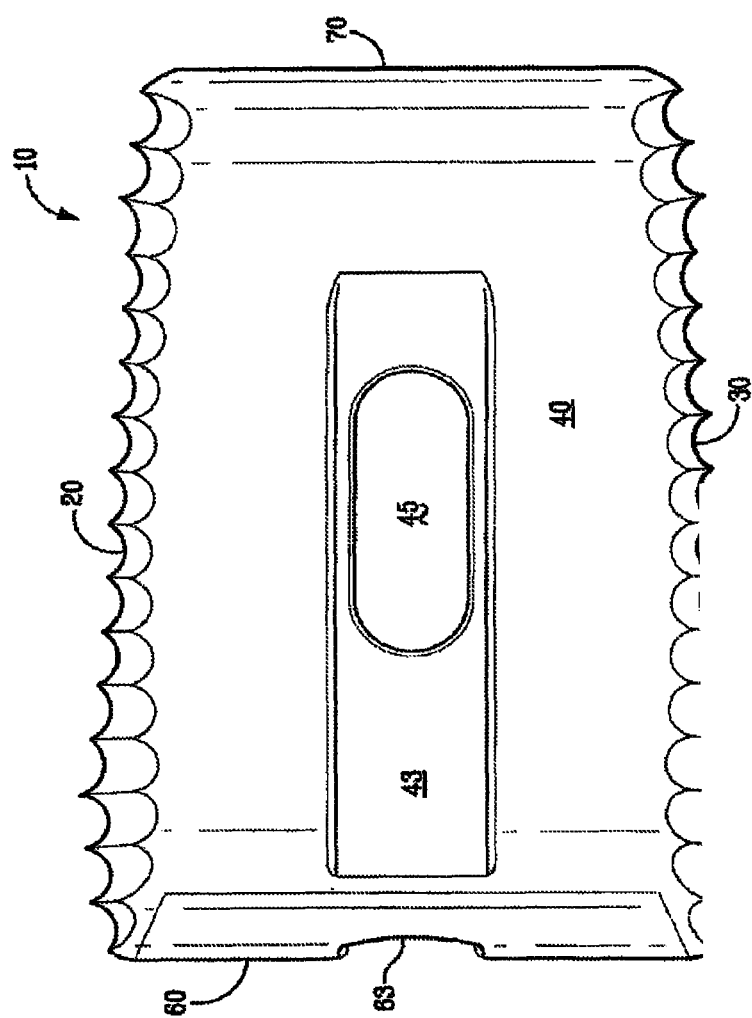
FIG. 3 provides a side view illustrating the medial side of the cervical implant 10.

The implant also has a handling feature that may comprise at least one pair of elongated side recesses 43 and 53 for receiving forceps and a front recess 63 for receiving an impaction tool. "Recess," as used herein, describes a recessed indentation that generally defines a depression in a surface, for example, such as that defined as 43, 53, and 63 in FIGS. 1-3. The front recess 63 may be used in conjunction with the anterior side 60 and front opening 65 as to communicate with an implant holder or insertion tool. The front recess 63 may be elongated with a major axis that is substantially transverse. The front recess 63 may have an aperture, the front opening 65, formed therein. This handling feature allows for handling and insertion of the spinal implant using instruments such as forceps. In some embodiments, the handling feature consists of only the front recess 63. In FIGS. 1 through 3, the sidewalls 40 further comprise side recesses 43 and 53 that may mate with an instrument to aid in insertion or removal of the implant. The sidewalls 40 also comprise at least one opening 45 (FIGS. 1 and 3) to allow fluid to enter the major recess 35 after insertion. Graft material may be supplied with blood and other biologic fluids through the openings 45. In other embodiments, the handling feature consists of only the side recesses 43 and 53. The surfaces of these recesses may be textured with an anti-skid material to prevent slippage of the insertion tool.

In FIGS. 1 and 2, the front recess is used to prevent rotation of the implant. The front recess 63 and a front opening 65 can mate with an implant insertion tool. The front recess 63 may be comprised of some other geometry suitable to prevent the implant from rotating on the end of the implant insertion tool during insertion or removal of the implant. In certain embodiments, the front opening 65 may be threaded to mate with a corresponding implant insertion tool. In other embodiments, the front recess 63 and/or the front opening 65 is eliminated.

Figure 5:
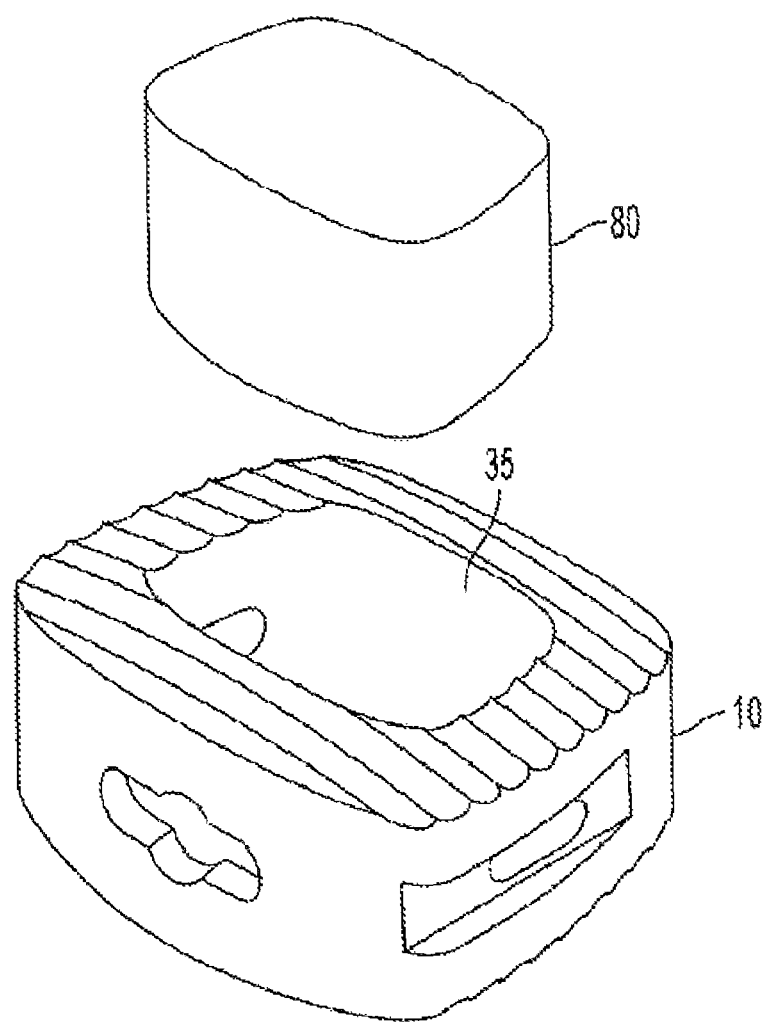
FIG. 5 provides an exploded view of the cervical implant 10 with a synthetic graft material.
Figure 5A:
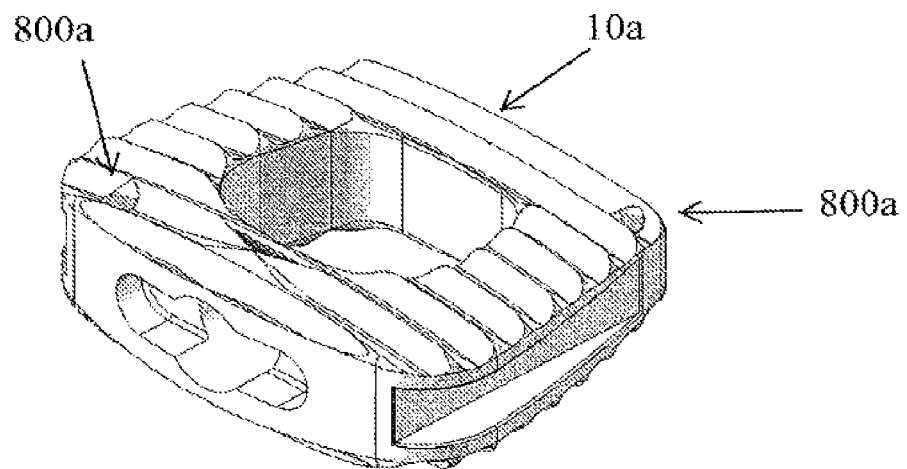
Figure 5B:
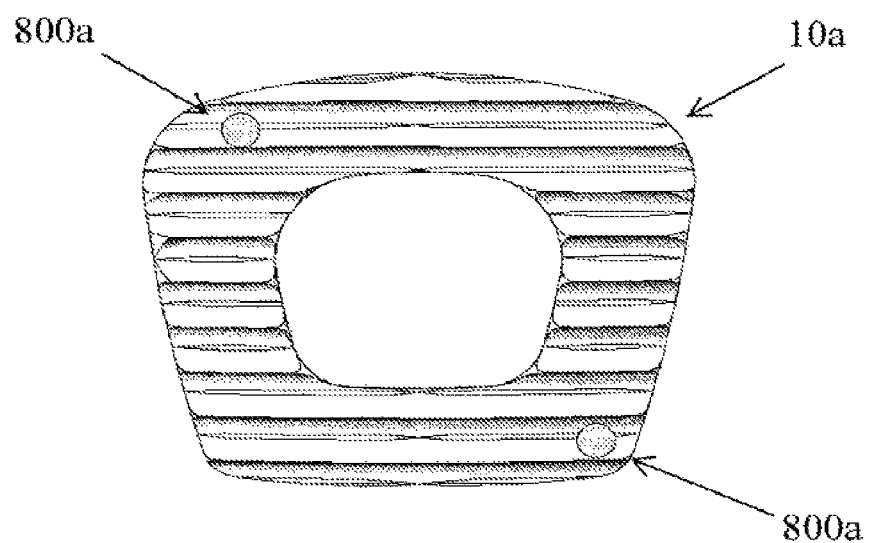

FIG. 5 provides an exploded view of the bioactive composite implant 10 showing an additional agent added to the composite implant—a graft material 80 agent being placed in the major recess 35. Graft material may be comprised of allograft material, autograft material, or synthetic materials that have similar properties to allograft or autograft materials. The synthetic graft material is preferably comprised of a biocompatible, osteoconductive, osteoinductive, or osteogenic material to facilitate the formation of a solid fusion column within the patient's spine. One such example of such a synthetic graft material is Vitoss® Bone Graft Substitute (available from Orthovita, Inc. of Malvern, Pa.). To foster bone fusion, the Vitoss® calcium phosphate material may be saturated with the patient's own bone marrow aspirate, or therapeutic material such as growth factor, proteins, bone marrow aspirate, enzymes and other materials such as those disclosed in U.S. Pat. No. 7,045,125. Thus, the bioactive composite implant may have incorporated therein or be in communication with other agents to aid in fusion of adjacent vertebrae. It should be noted that in preferred embodiments, the posterior side 70 does not have an opening therethrough. This facet of the design is a safety feature implemented to prevent leakage of graft materials placed in the major recess 35 into the spinal canal.

FIGS. 5a and 5b show an alternate embodiment of a spinal implant. Similar to the implant of FIG. 1, the implant 10a of FIGS. 5a and 5b has a generally trapezoidal shape and a major recess having a through-aperture that is in communication with both top and bottom surfaces. The implant also has a handling feature that may comprise at least one pair of elongated side recesses for receiving forceps and a front recess for receiving an insertion/impaction tool. The front recess may be used in conjunction with the side recesses and/or front opening to communicate with an implant holder or insertion tool; however, unlike the implant of FIG. 1, the implant of FIGS. 5a and 5b does not have side openings. The implant also includes a radiopaque agent—titanium markers 800a to provide the surgeon with radiopaque landmarks upon insertion and while the implant is in the body.

Figure 6:
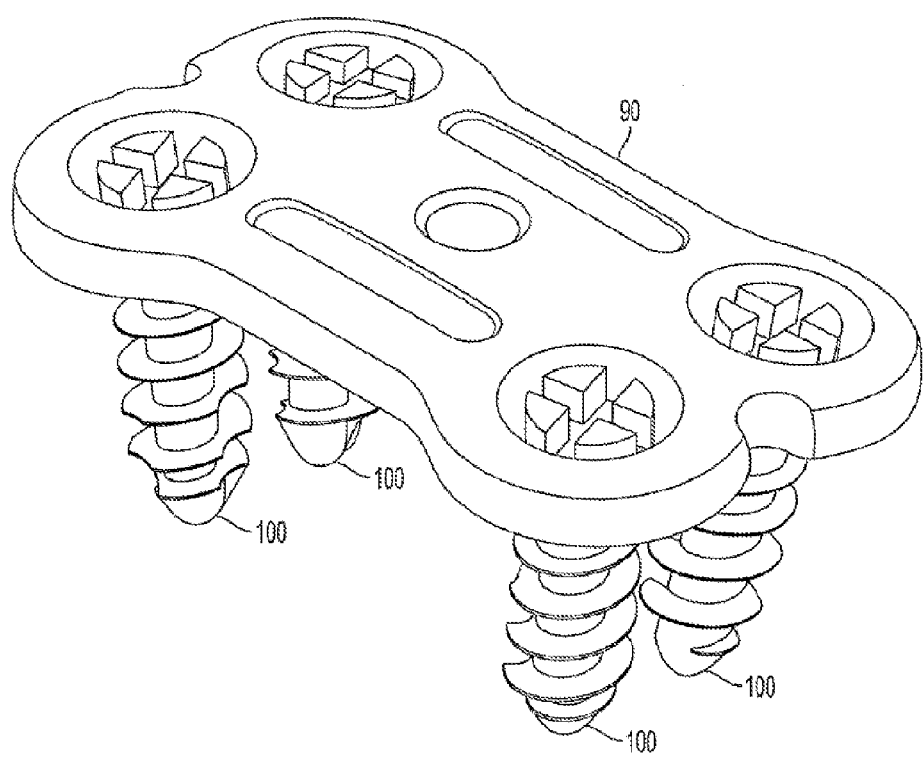
FIG. 6 provides an isometric view of a cervical plate and fastener assembly 100.
Figure 7:
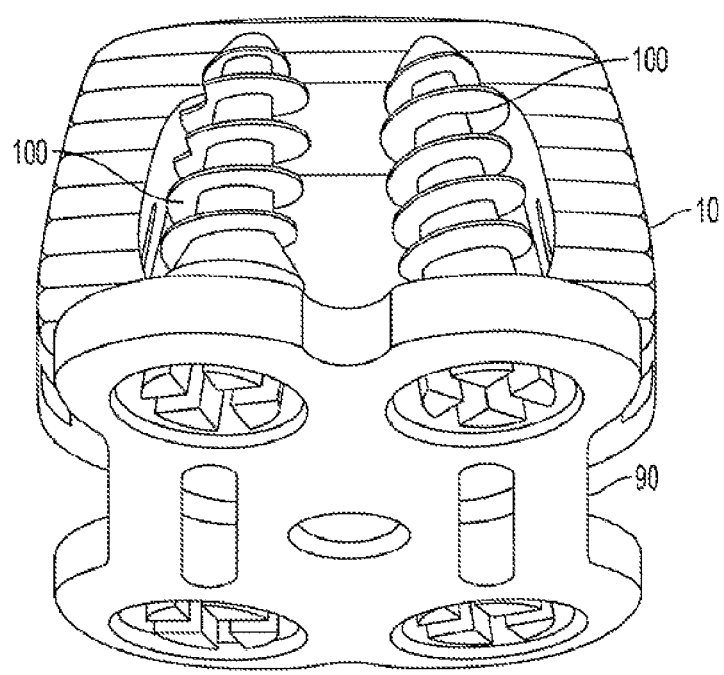
FIG. 7 provides an isometric view of a cervical implant with a cervical plate and fastener assembly 100.
Figure 8:
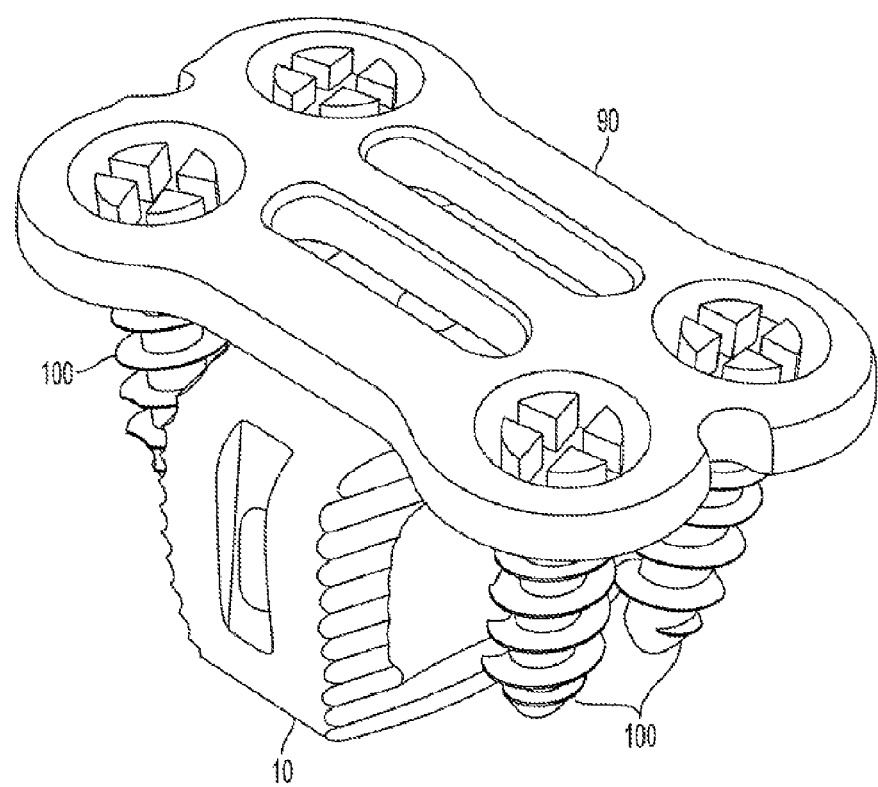
FIG. 8 provides another view of the cervical implant with the cervical plate and fastener assembly 100.

FIGS. 6 through 8 show a plate 90 and fastener 100 assembly that may be used in conjunction with implant 10. The plate and fastener assembly may facilitate fusion of adjacent vertebrae by stabilizing the implant in place between the vertebrae. Fasteners 100 may be comprised of screws, pins, nails, and the like. They are inserted into openings within plate 90 to engage the adjoining vertebral bodies. Upon insertion, one pair of fasteners is inserted in the upper vertebral body and one pair is inserted in the lower vertebral body.

Figure 9:
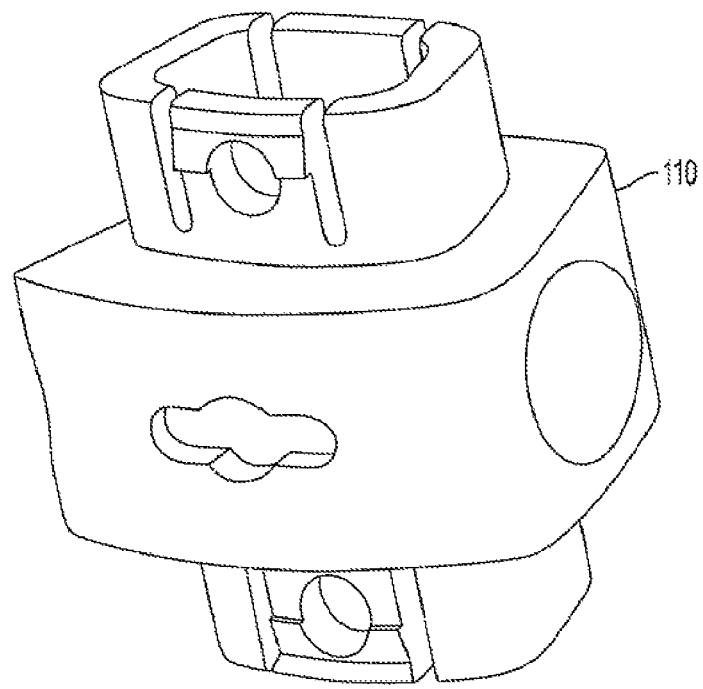
Figure 10:
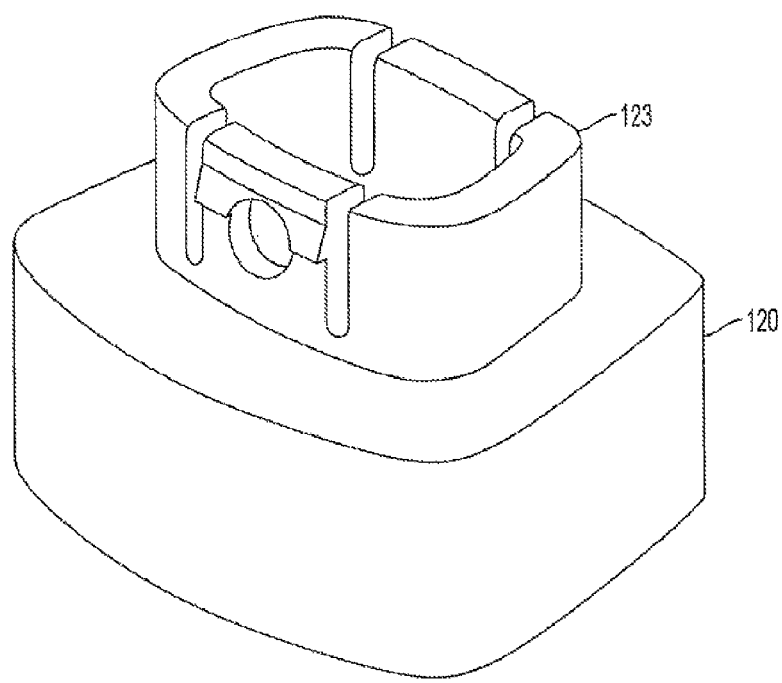
Figure 11:
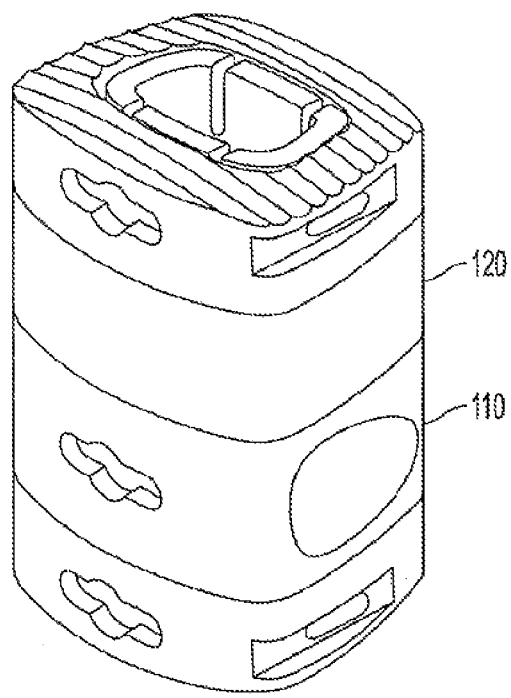

FIGS. 9 through 11 show accessories 110 and 120 that are used to connect one or more implants 10 as shown in FIG. 11. Accessories 110 and 120 may be used in corpectomy procedures in which the surgeon removes one or more vertebrae and needs to restore the spine to its former height. In FIG. 9, accessory 110 has two male ends that may engage, for example, the major recess 35 of implant 10 or the female end of accessory 120. In FIG. 10, accessory 120 has a male end 123 and a female end that allows implants to be joined together as shown in FIG. 11. Accessories 110 and 120 may be joined together with implants 10 via snap or compression fit via one or more flexible tabs, fasteners, adhesives, or other means.

Trial instrument kits may be used with the present invention spinal implant to aid in determining proper sizing of the final implant for each individual patient. Non-limiting examples of such kits include Spinal Elements® Crystal® Cervical Cage System and Crystal® Instruments.

Anterior Lumbar Interbody Fusion (ALIF) Implants

The bioactive material of the present invention may also be formed into an implant suitable for ALIF procedures. ALIF implant devices are generally suitable for implantation in the lumbar regions of the spine.

Figure 12:
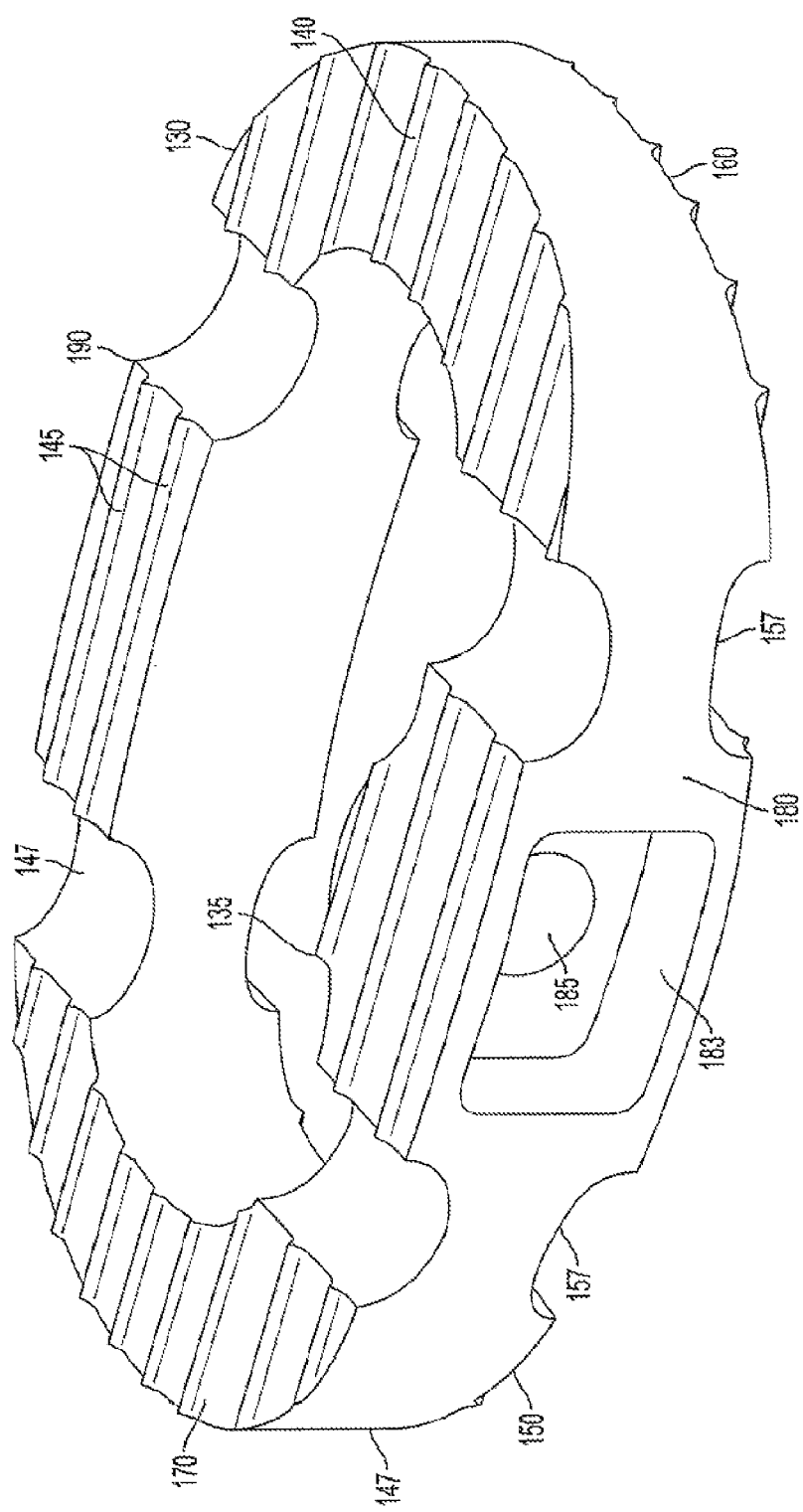
FIG. 12 provides an isometric view of one embodiment of the anterior lumbar interbody fusion (ALIF) implant 130.
Figure 13:
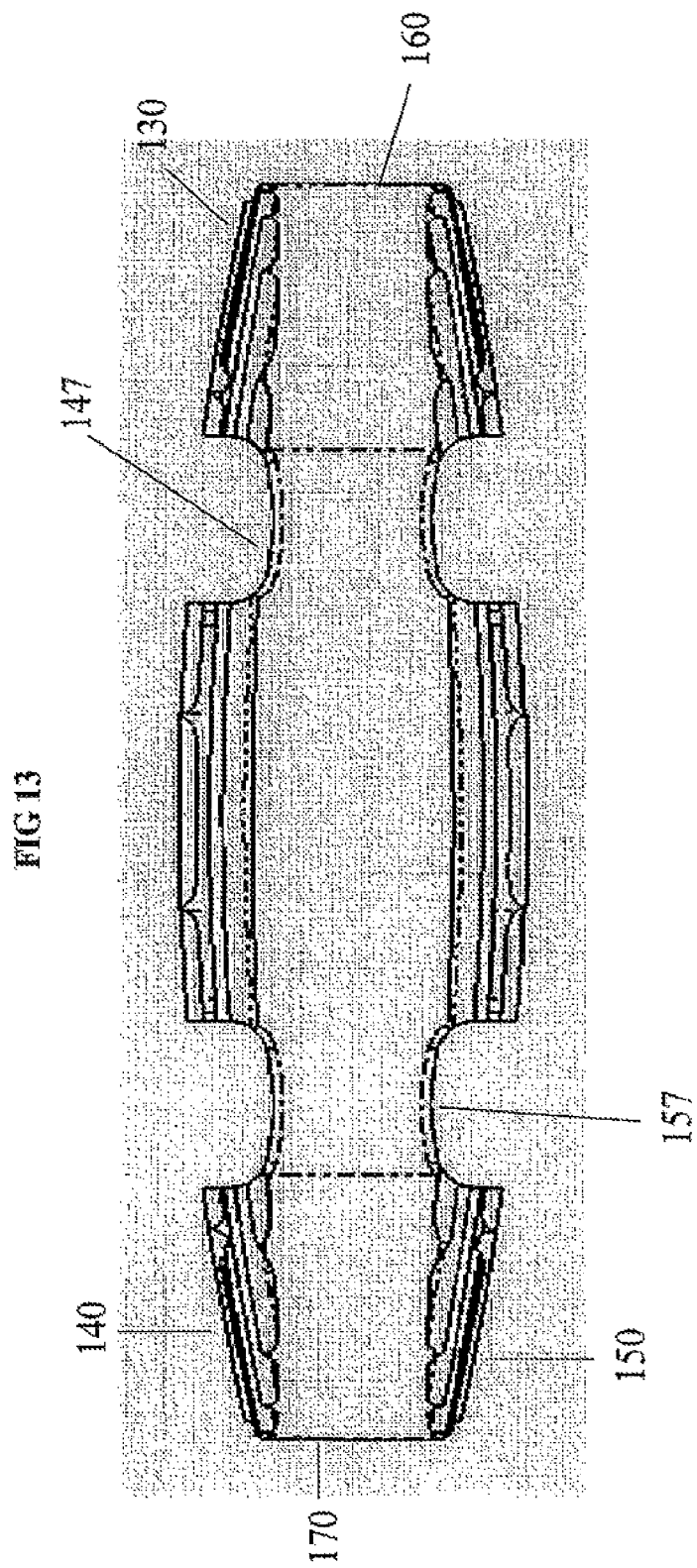
FIG. 13 provides a front view illustrating the anterior side of the ALIF implant 130.
Figure 14:
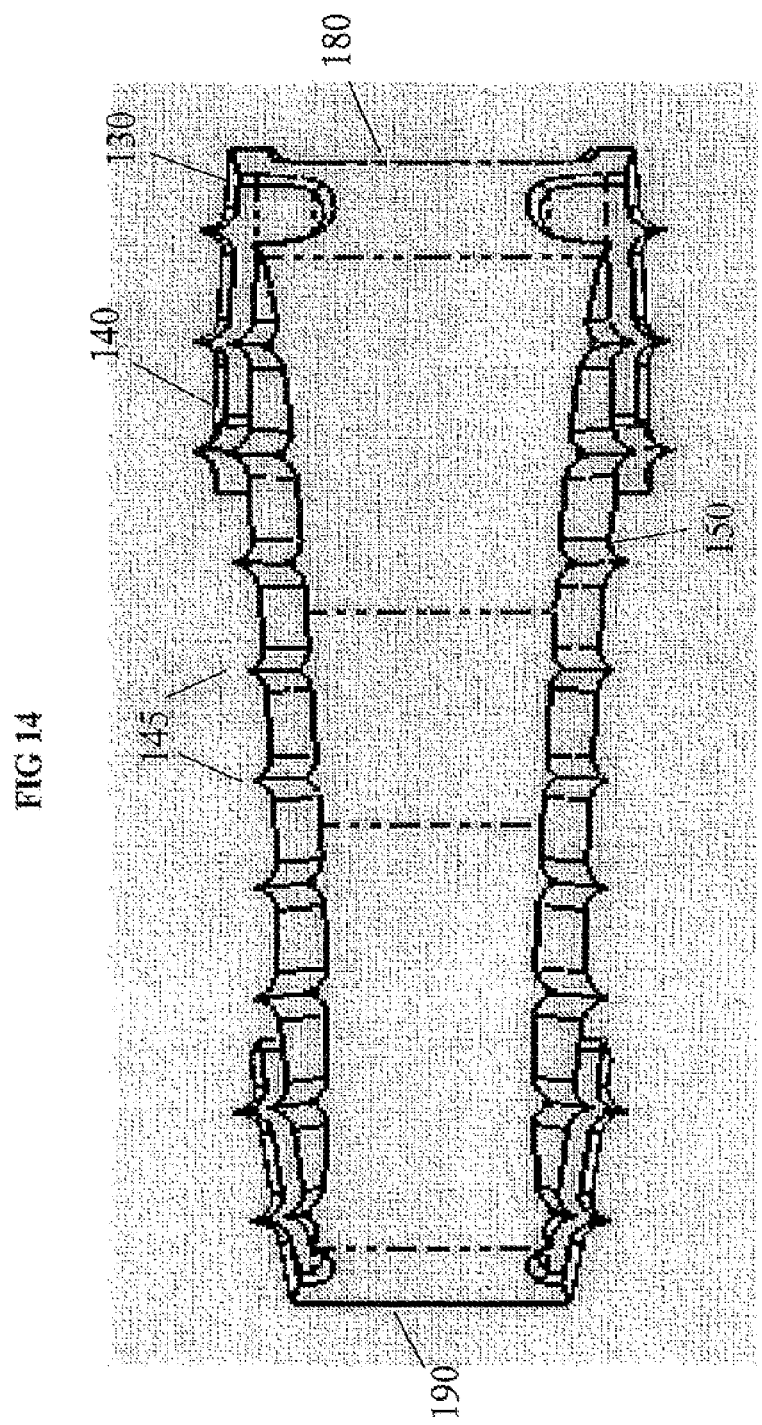
FIG. 14 provides a side view illustrating the medial side or lateral side of the ALIF implant 130.

FIGS. 12 through 14 depict one embodiment of the ALIF implant 130 of the present invention. Like the cervical implant of the present invention, implant 130 may be in a variety of different sizes to accommodate differences in the patient's anatomy or the location of the spine that implant 130 will be inserted. The body may substantially form an oval shape in the longitudinal cross-section. The implant is a body comprising a bioactive substance and further comprising: an anterior side 180, a posterior side 190 opposing the anterior side 180, and a pair of opposing sidewalls 160, said sidewalls 160 being generally outwardly curved or generally "c-shaped." The anterior 180 and posterior 190 sides may be parallel and in others they are outwardly curved. The implant also has a top surface 140 and a bottom surface 150, both surfaces coupled with the sidewalls 160. Top surface 140 and the bottom surface 150 form plural projections 145 for enhancing interaction with a synthetic or natural vertebral body. At least one major recess 135 is formed in the body in communication with at least one of the top surface 140 and the bottom surface 150.

Also in FIGS. 12 and 14, top 140 and bottom 150 surfaces further include a plurality of projections 145, preferably wave-like or scalloped in shape, for gripping adjacent vertebrae. These projections share the same characteristics of the plurality of projections 25 noted in the description of the cervical implant.

FIG. 14 illustrates one embodiment of the present invention. FIG. 14 illustrates implant 130 having a lordotic angle: The lordotic angle can range from −20 degrees to +20 degrees.

Similar to the cervical implant 10, the ALIF implant has a major recess 135 that forms a through-aperture. This shape maximizes contact with the cortical bone in the thoracic and lumbar regions. In preferred embodiments, the top 140 and bottom 150 surfaces are substantially identical in size and shape. The major recess 135 also maximizes the chances of fusion because an additional agent-graft or resorbable material may be packed within implant 10. It should be noted that in preferred embodiments, posterior side 190 does not have an opening therethrough. This is to prevent leakage of graft materials from the major recess 135 into the spinal canal.

The implant also has a handling feature comprising recesses 147 and 157 along the top 140 and bottom 150 surfaces extending from either the anterior 180 and posterior 190 sides that act as guide rails and at least one recess 185 in the anterior or sidewalls 160 for receiving an impaction tool. FIGS. 12 and 13 show the recesses 147 and 157 that act as guide rails. The guide rails mate with an instrument, such as a parallel distraction instrument, to aid in insertion or removal of the implant. The plurality of guide rails holds the implant securely and may allow the surgeon to insert the implant more evenly.

FIG. 12, shows the implant 130 having a front recess 183 used as an anti-rotation recess and a front opening 185. The front recess 183 and opening 185 share the same characteristics as the front recess 63 and front opening 65 of the cervical implant described earlier.

Figure 15:
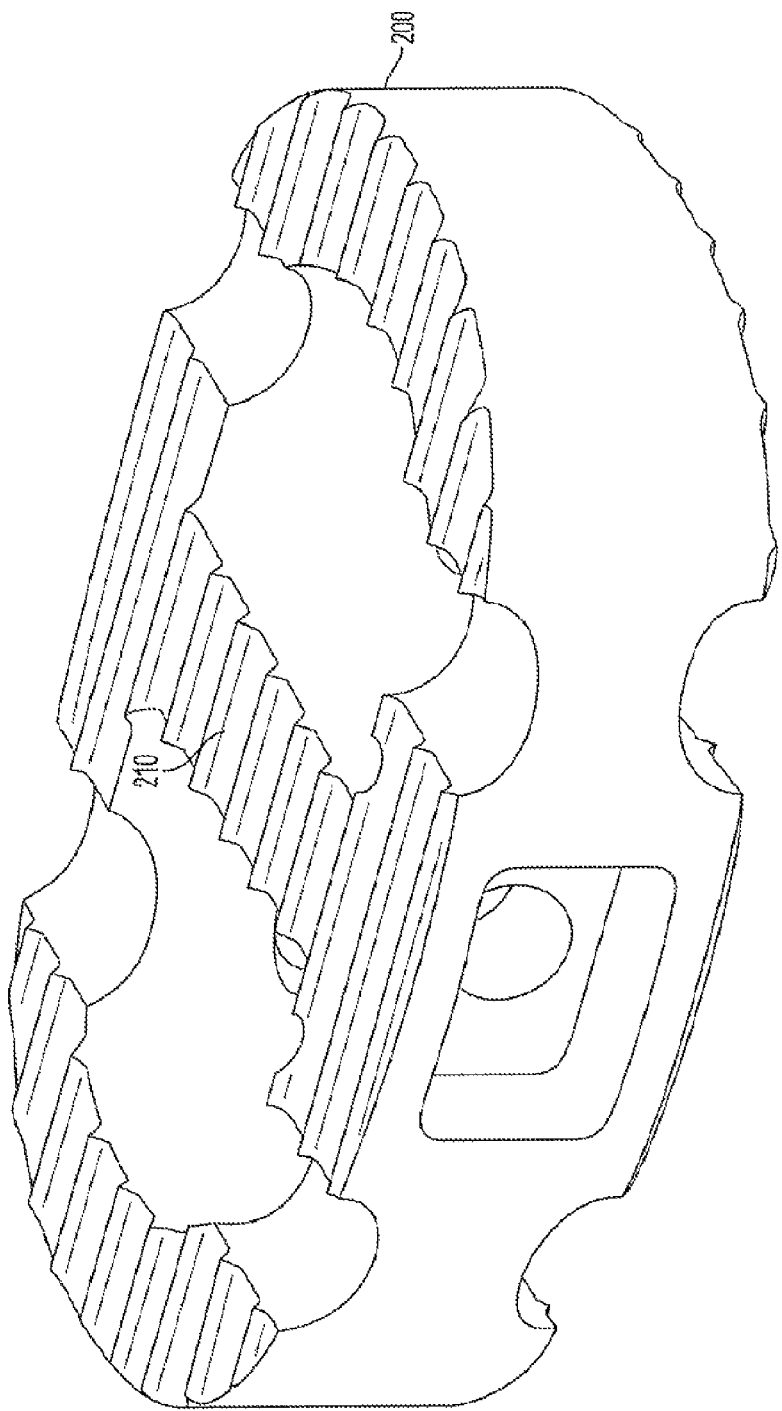
FIG. 15 provides an isometric view of an alternate embodiment of the ALIF implant 200.
Figure 16:
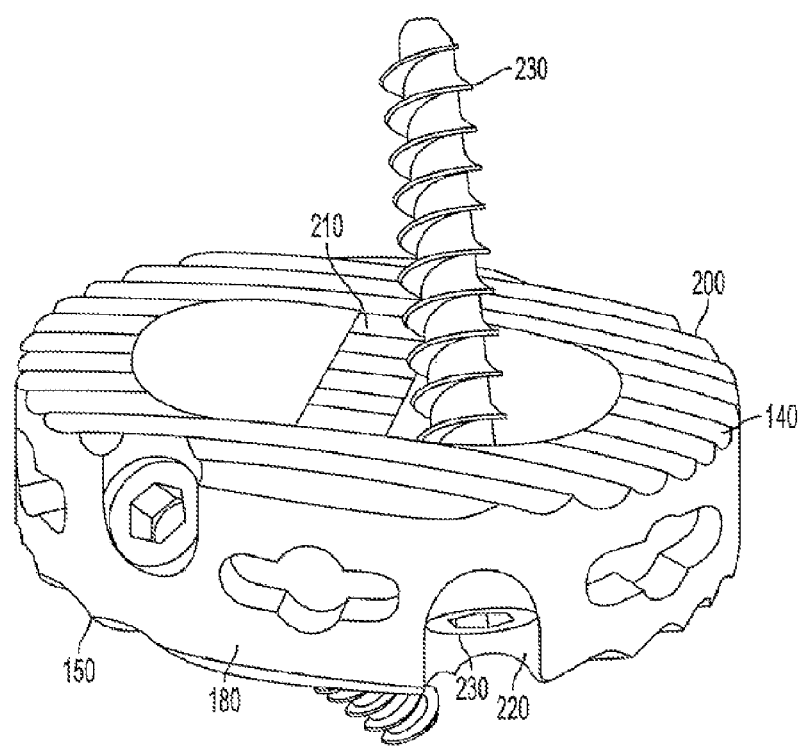
FIG. 16 provides an isometric view of the ALIF implant 200 that includes a fastening feature.
Figure 17:
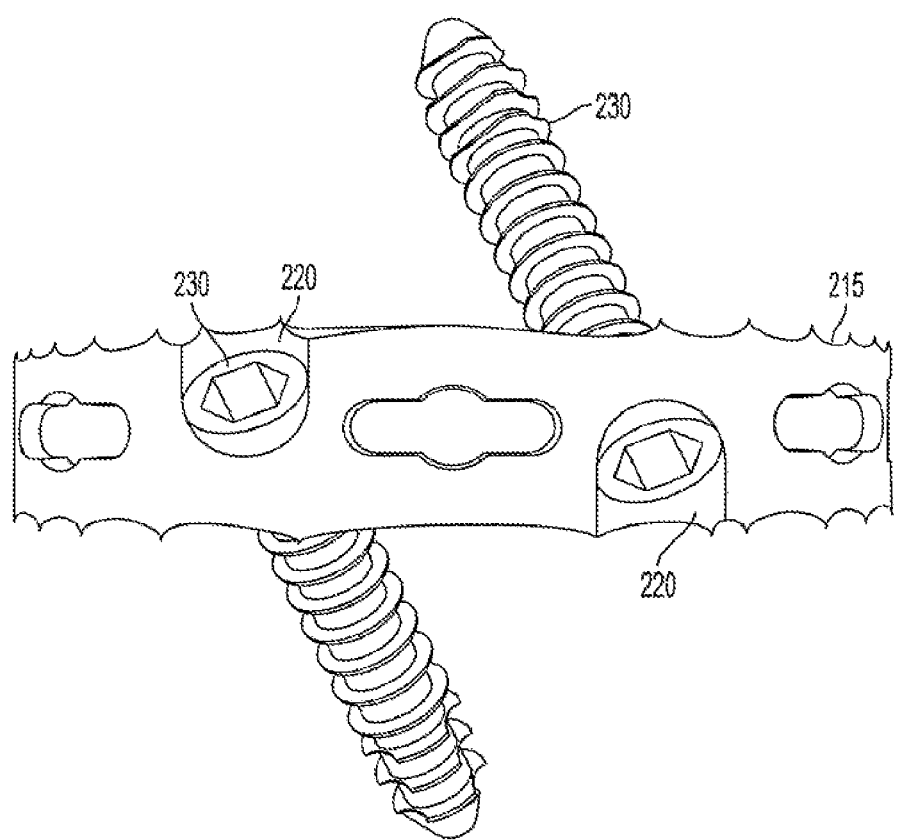
FIG. 17 provides a front view of the ALIF implant and a fastening feature.
Figure 18:
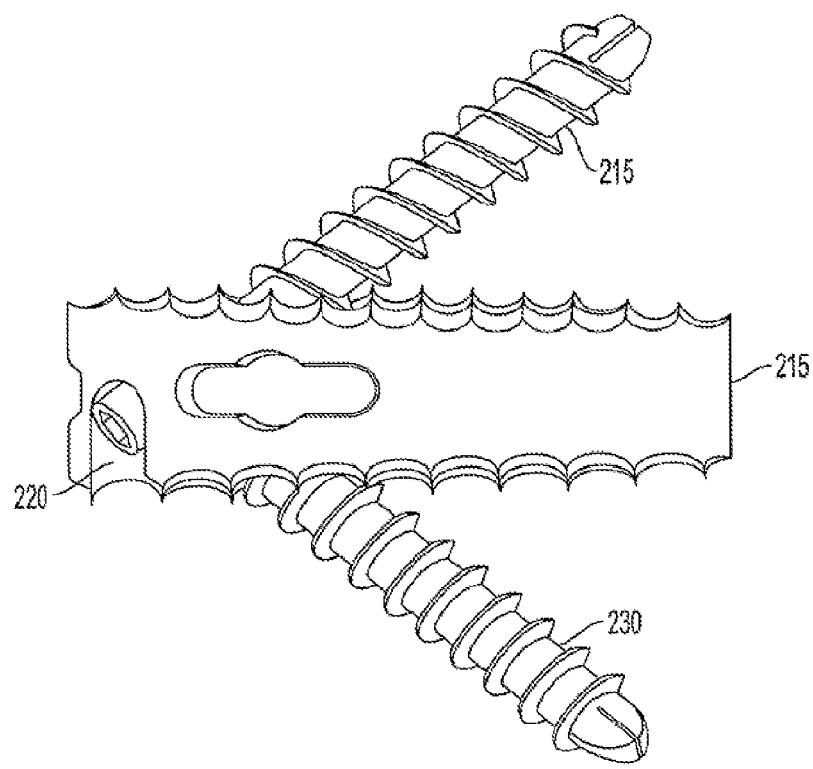
FIG. 18 provides a side view of the ALIF implant and a fastening feature.
Figure 19:
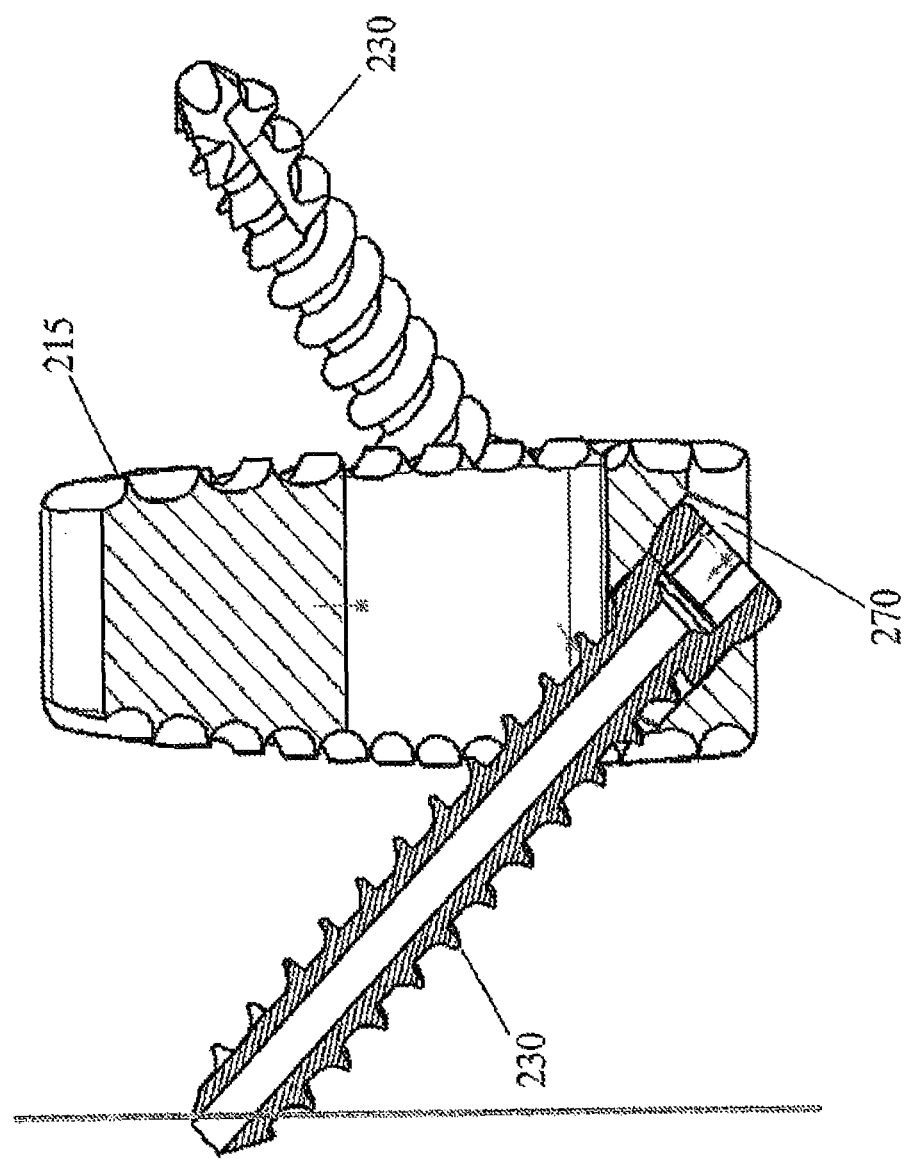
FIG. 19 provides a cross-sectional view of the ALIF implant and a fastening feature.

FIG. 15 provides an isometric view of an alternative embodiment 200 of the ALIF implant of the present invention. Implant 200 includes a strut 210 that divides the major recess 135 into two through-apertures to provide support during anterior impaction of the implant during insertion. A strut 210 that has the top 140 and bottom 150 surfaces with projections 145 separates the through-apertures.

FIGS. 16 through 19 provides yet another embodiment of the present invention in which an ALIF implant 215 or implant 200 further includes a fastening feature. The fastening feature comprises at least one through-aperture 220 in communication with the anterior 180 side and either the top 140 or bottom 150 surface for insertion of fasteners 230 that communicate with a synthetic or natural vertebral body either below or above the implant. This feature includes a plurality of openings 220 on the anterior side of implant 200 for receiving fasteners 230. Fasteners 230 may include, but are not limited to, screws, pins, nails, or any other fixation devices. In certain preferred embodiments, openings 220 are angled to allow fasteners 230 to move at varying angles up and in or down and in. An angle in some embodiments that may be preferred is below about 90 degrees. In others, and angle of about 45 degrees may be preferred. Fasteners 230 help to anchor implant 215 since the upward tilted fastener is inserted into the upper vertebral body and the downward tilted fastener is inserted into the lower vertebral body.

Posterior Lumbar Interbody Fusion (PLIF) Implants

The bioactive material of the present invention may also be formed into an implant suitable as for PLIF procedures. PLIF implant devices are generally suitable for implantation in the lumbar regions of the spine.

Figure 20:
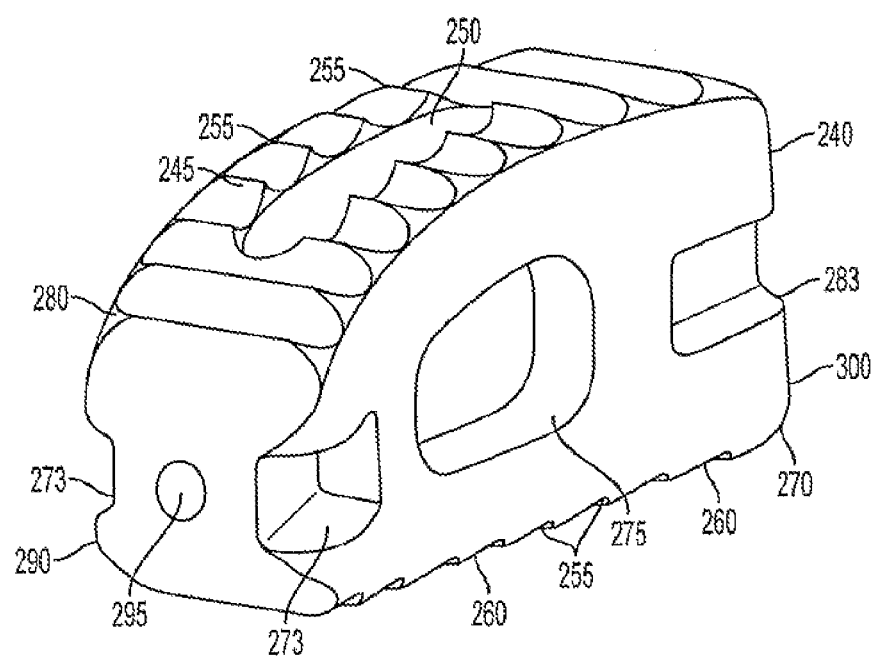
FIG. 20 provides an isometric view of one embodiment of the posterior lumbar interbody fusion (PLIF) implant 240.
Figure 21:
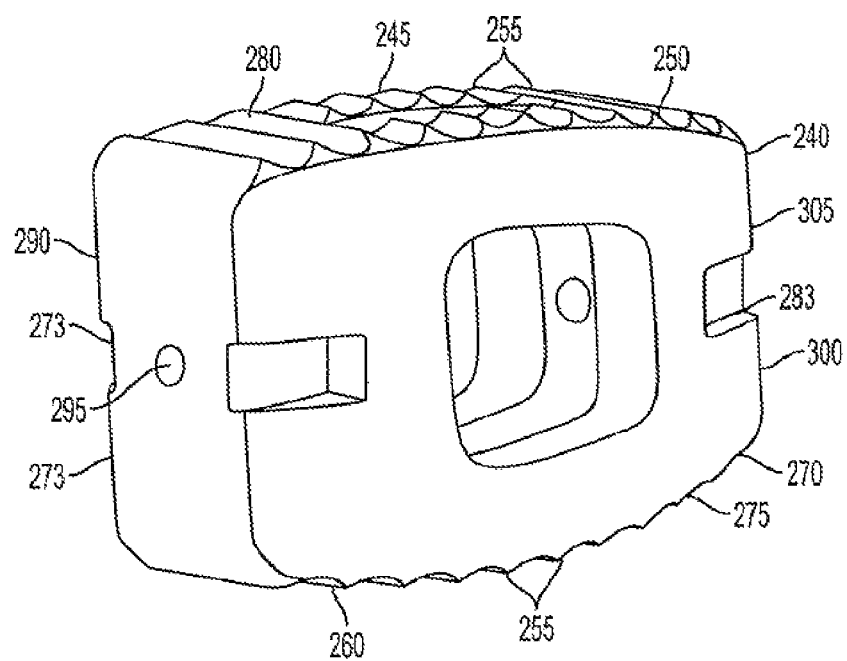
FIG. 21 provides an isometric, side view of another embodiment of the PLIF implant 240.
Figure 22:
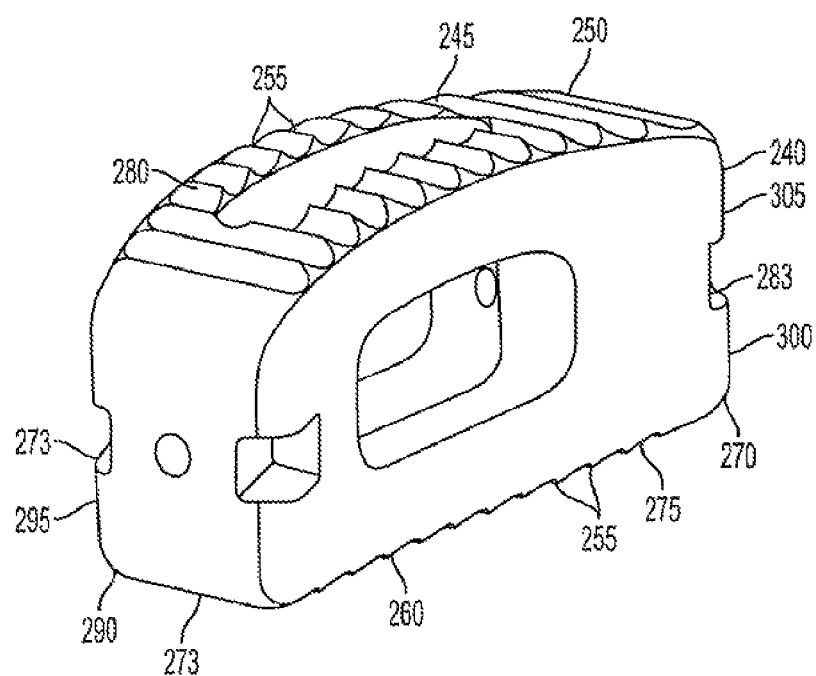
FIG. 22 provides an isometric view of yet another embodiment of the PLIF implant 240.
Figure 22A:
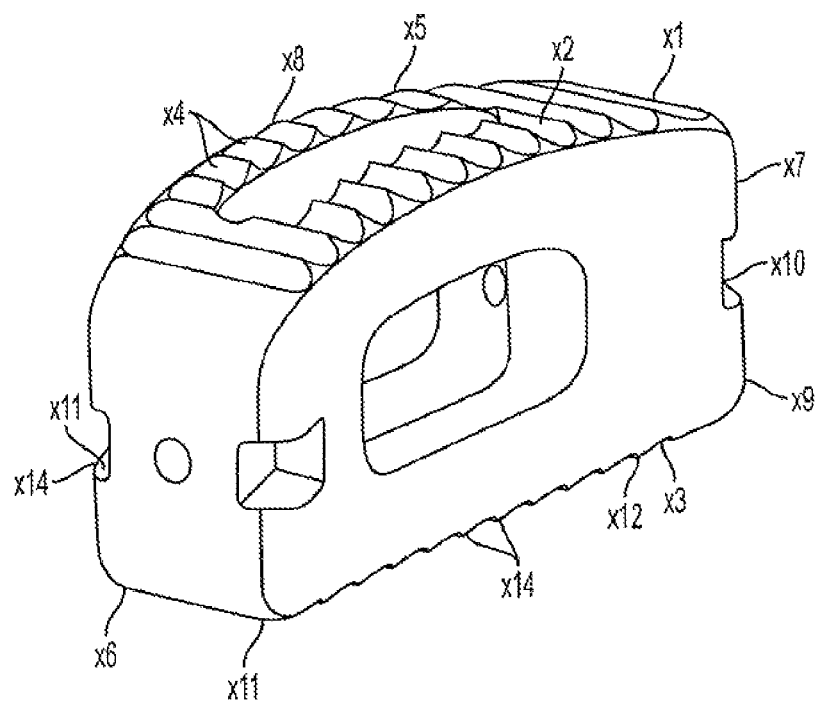
FIG. 22a provides an isometric view of one embodiment of a transforaminal lumbar interbody fusion (TLIF) implant x1.

The PLIF implant 240 of the present invention may be in a variety of different sizes to accommodate differences in the patient's anatomy or the location in the spine. As FIGS. 20 through 22 illustrate, implant 240 comprises an anterior side 290 and a posterior side 300 being parallel to and opposing the anterior side 290; a lateral 280 side and a medial 270 side with one side being outwardly curved and the other being inwardly curved; and a top surface 250 and a bottom surface 260, each of the top 250 and bottom surfaces 260 including plural projections 255 for enhancing interaction with a synthetic or natural vertebral body. The projections 255 are similar in geometry to the protrusions in the cervical and ALIF implants of the present invention.

The implant also comprises a major recess 245 formed in the body creating a longitudinal through-aperture in communication with the top 250 and bottom 260 surfaces, at least one minor recess 275 formed in the body creating a latitudinal through-aperture in communication with the lateral 280 and medial 270 sides, both through apertures in communication with each other. The convergence of these through-apertures forms a cavity inside the implant in which graft material may be placed. This cavity formed by the through-apertures promotes bone growth and fusion between the adjoining vertebral bodies. Opening 245 may be packed with graft material to promote bone growth and fusion. Graft materials suitable for this purpose includes any of the materials disclosed herein. Blood and other biological fluids can be provided to the graft material through the minor recess 275.

The implant also comprises a handling feature comprising a pair of anterior recesses 273 formed at points where the anterior 290 side communicates with the lateral 280 and medial 270 sides. The anterior recesses 273 are used for receiving a manipulator. There are also a pair of posterior recess 283 formed at points where the posterior 300 side communicates with the lateral 280 and medial 270 sides. The handling feature also includes a front opening 295 formed in the anterior 290 side. The handling feature facilitates the handling and insertion of the spinal implant into an intervertebral space.

FIGS. 20 and 22 illustrate implant 240 having a lordotic angle. The lordotic angle can range from −20 degrees to +20 degrees. In other embodiments, anterior side 300 and posterior side 290 are of the same height and have no lordotic angle.

In FIGS. 20 through 22, the anterior recesses 273 and the posterior 283 recesses may mate with an instrument, such as forceps, to add in the insertion or removal of the implant. The front 295 and rear openings 305 also allow implant 280 to be gripped and mated with an insertion tool. In certain embodiments, the medial 270 and lateral 280 sides may further comprise at least one minor recess 275 (or 285) to allow fluid to enter the interior of the implant after insertion.

Implant 240 may further include an opening 295 in posterior side 300, that is preferably internally threaded to accommodate an insertion tool, but that does not completely extend through the thickness of the posterior wall. This facet of the design is a safety feature implemented to prevent leakage of graft materials and the like, that may be placed in the hollow interior of the implant, into the spinal canal.

Implant 240 may be used alone or in conjunction with a complimentary implant. The two implants can be placed along side one another as in a mirror image with the medial 270 sides facing one another. This configuration allows bone graft material to be placed between two implants 240 and provides for maximum contact between natural bone and the implants.

Transforaminal Lumbar Interbody Fusion (TLIF) Implants

The bioactive material of the present invention may also be formed into an implant (FIGS. 22a-22d) suitable for TLIF procedures. TLIF implant devices are generally suitable for implantation in the lumbar regions of the spine.

In another embodiment of the present invention (FIG. 22a), the TLIF implant x1 of the present invention may be in a variety of different sizes to accommodate differences in patient's anatomy or the location of the spine that the implant x1 will be inserted. The TLIF implant x1 may be a variety of different sizes to accommodate differences in the patient's anatomy or the location in the spine. As FIGS. 22a through 22d illustrate, implant x1 comprises an anterior side x6 and a posterior side x7 being parallel to and opposing the anterior side x6 and a lateral x8 side and a medial x9 side with at least one side being outwardly curved. The implant also comprises a top surface x2 and a bottom surface x3, each of the top x2 and bottom surfaces x3 including plural projections x4 for enhancing interaction with a synthetic or natural vertebral body. Wave-like projections x4 are similar to the cervical, ALIF, and PLIF implants of the present invention.

Top surface and bottom surface x2 and x3 further define at least one major recess x5 to promote bone growth and fusion between the adjoining vertebral bodies. The major recess x5 creates a longitudinal through-aperture in communication with the top x2 and bottom x3 surfaces. The major recess x5 may be packed with graft material to further promote bone growth and fusion. Graft materials suitable for this purpose includes any of the materials disclosed herein.

As FIGS. 22a through 22d illustrate, the anterior x6 and posterior x7 sides are generally flat and parallel. In certain preferred embodiments, the lateral x8 side is outwardly curved and the medial x9 side is inwardly curved.

The implant also comprises a handling feature comprising a pair of anterior recesses x11 formed at points where the anterior x6 side communicates with the lateral x8 and medial x9 sides and a pair of posterior recess x10 formed at points where the posterior x7 side communicates with the lateral x8 and medial x9 sides. The pairs of recesses (x10 and x11) may be used for communication with a manipulator or instrument, such as, forceps. The handling feature also includes a front opening x14 formed in the anterior x6 side and a rear opening formed in the posterior x7 side both communicating with a through-aperture. This through-aperture is also in communication with the cavity formed in the spinal implant by the longitudinal and latitudinal through-apertures. The handling feature facilitates the handling and insertion of the spinal implant into an intervertebral space.

Figure 22C:
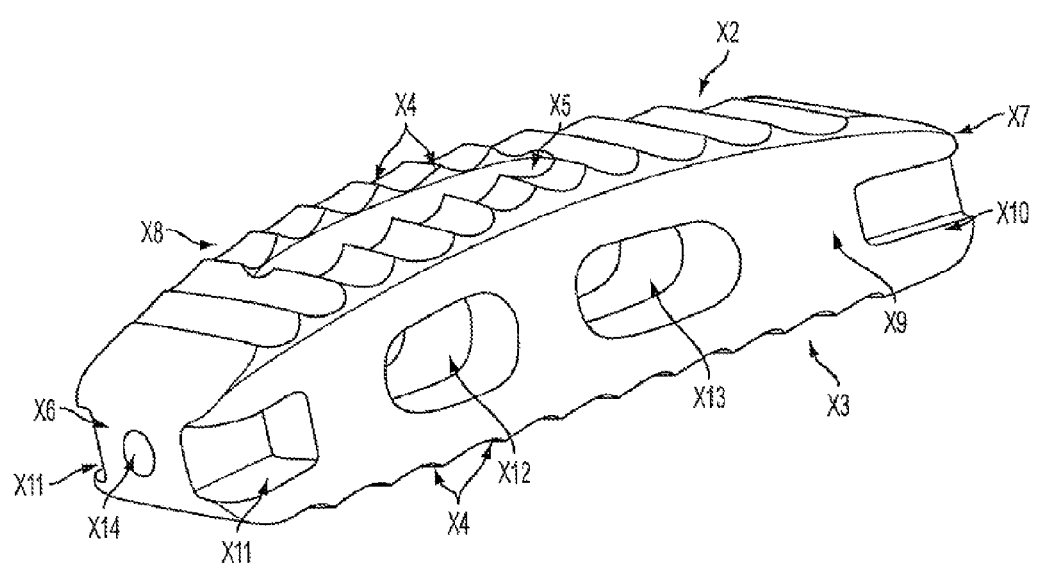
FIG. 22c provides an isometric view of one embodiment of a TLIF implant illustrating two lateral openings.
Figure 22D:
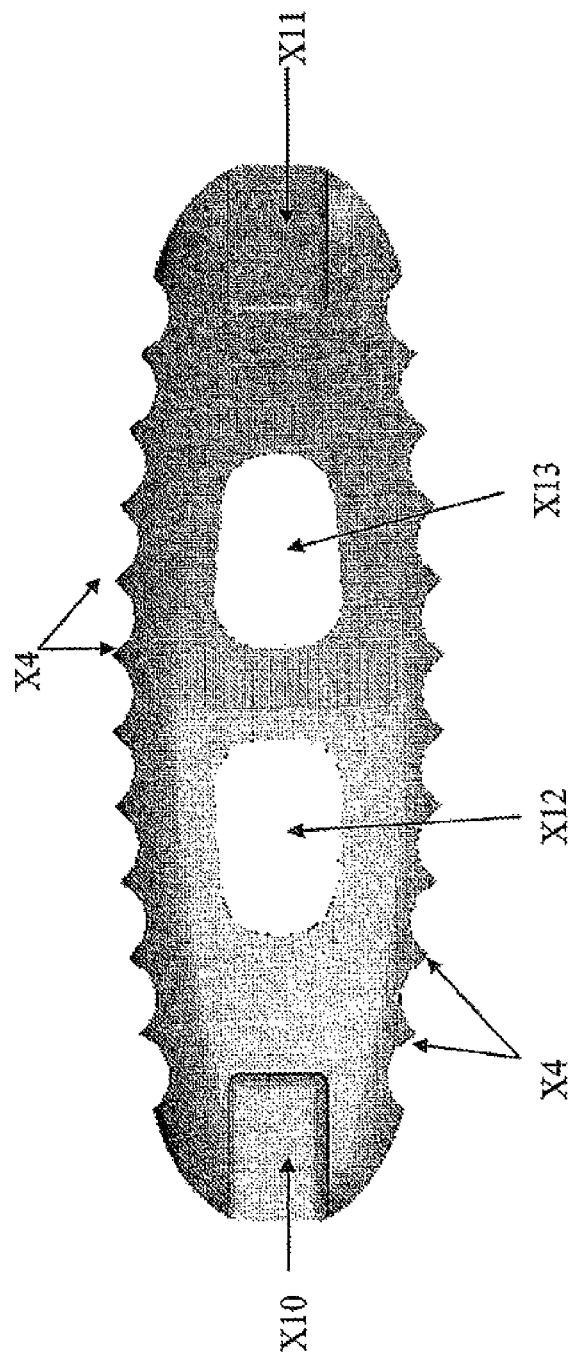
FIG. 22d provides a planar view illustrating the openings x12 and x13 and recesses on the anterior and posterior sides of the TLIF implant.

In certain embodiments (FIG. 22c), lateral x8 and medial x9 sides may further comprise at least one opening x12 and x13 to allow fluid to enter the interior of the implant after insertion to provide graft material placed in the center of the implant with blood or other biological fluids. FIGS. 22c and 22d show an embodiment of the implant with two side openings x12 and x13 per wall. However, it should be understood that the implant may not have side openings, or may have multiple pinhole openings along the length.

Implant x1 may further include an opening x14 in both of the anterior x6 and posterior x7 sides that may be internally threaded to accommodate an insertion tool. The front recess x14 may have an internal taper to mate with a tapered insertion instrument.

As shown in FIG. 22c, the top and bottom surfaces and may be outwardly curved. Further, the implant may be wedge shaped such that there is a lordotic angle. The lordotic angle may be same as those described earlier in other embodiments of the invention. In some embodiments the height of the wall of the anterior side x6 is greater than the height of the wall of the posterior side x7. Alternatively, the height of these walls may be equal.

The TLIF implant of the present invention is designed to engage the cortical rim of the vertebrae, the strongest portion of the vertebrae, and, as such, increases biomechanical stability. Additionally, the placement of this type of implant is generally less invasive and less destructive than other procedures, and may be cost effective since only one implant is used.

Surgical Instrumentation

The present invention also provides surgical instrumentation to aid in the insertion, placement, or removal of the implants of the present invention.

Figure 23:
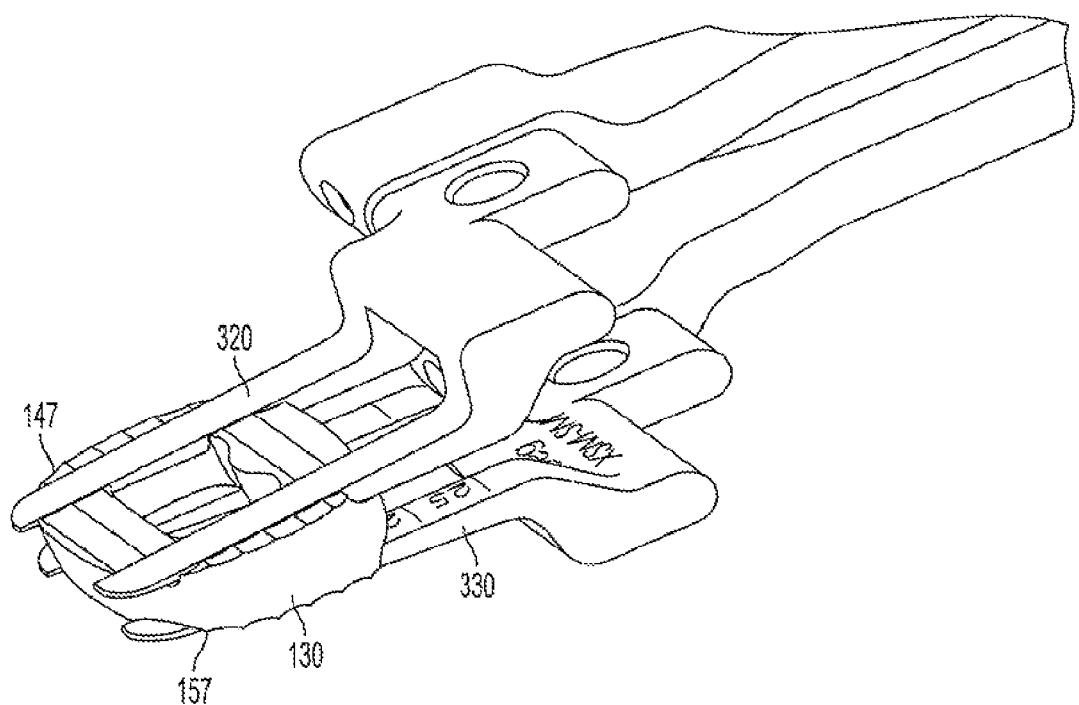
FIG. 23 provides an isometric view of one embodiment of the parallel distraction instrument engaging the ALIF implant 130.
Figure 24:
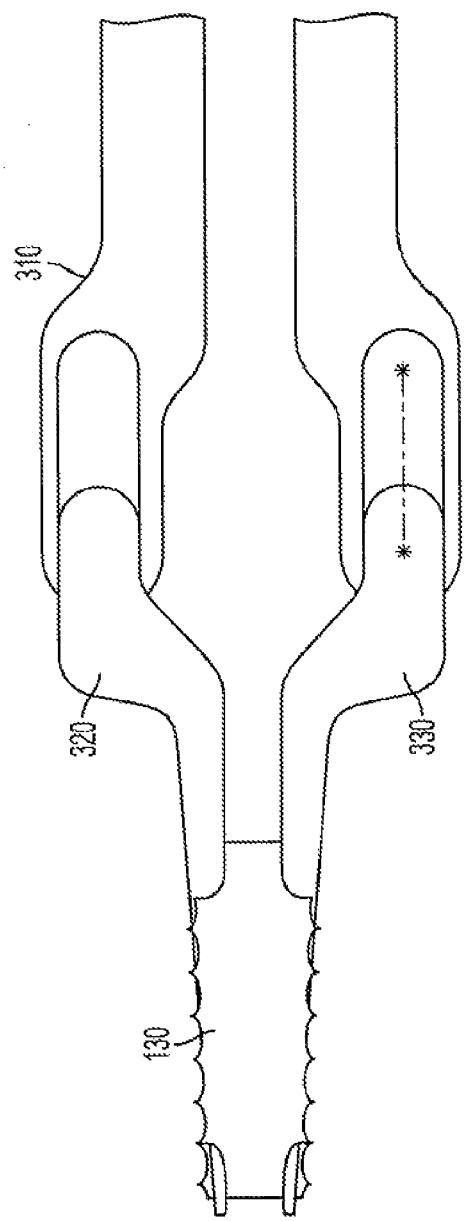
FIG. 24 provides a side view of the parallel distraction instrument 310 engaging the ALIF implant 130.
Figure 25:
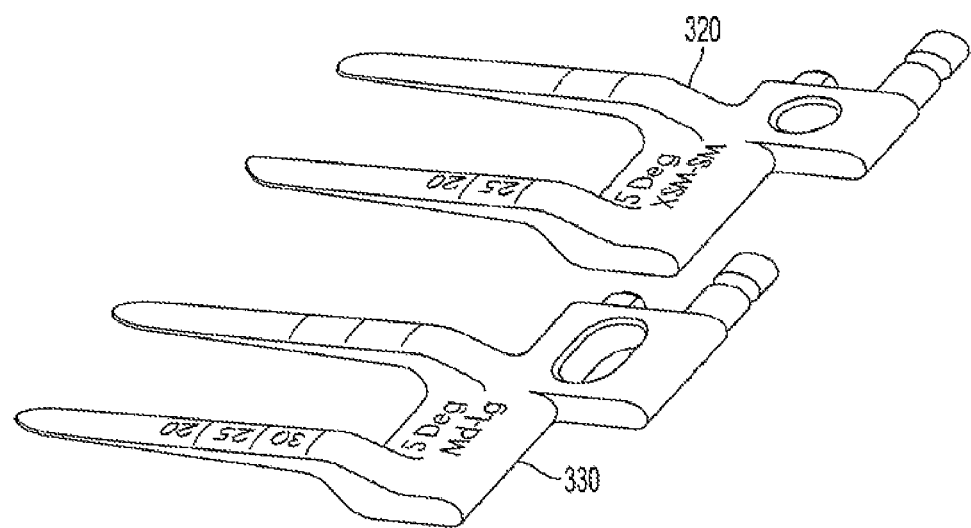
FIG. 25 provides an exploded view of the pair of upper 320 and lower forks 330 of the parallel distraction instrument 310.
Figure 26:
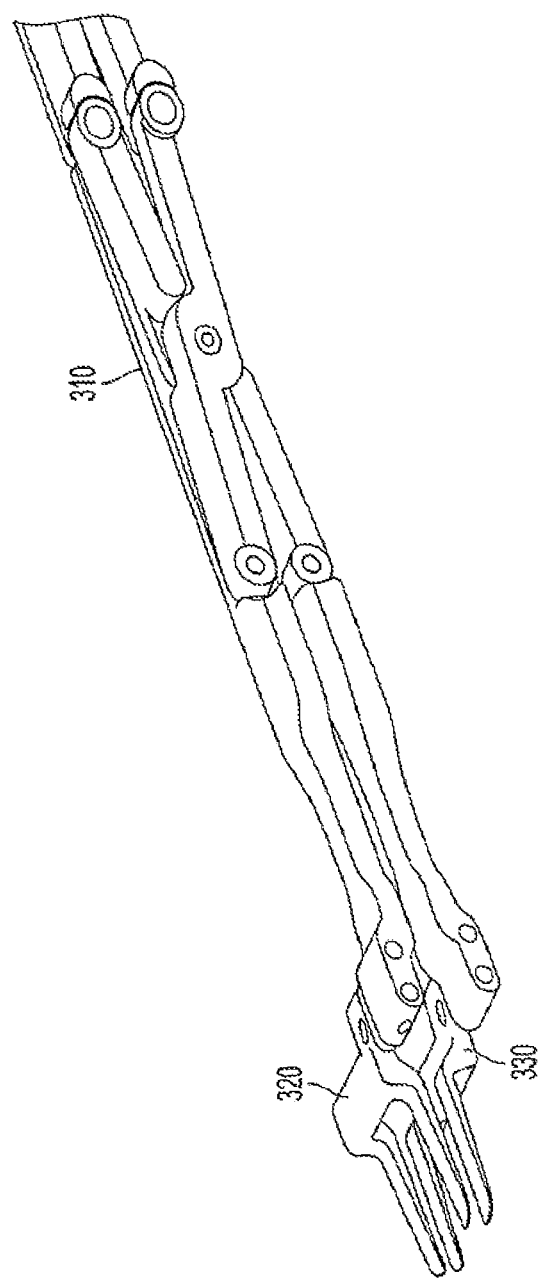
FIG. 26 provides a detailed, isometric view of the parallel distraction instrument 310.
Figure 27:
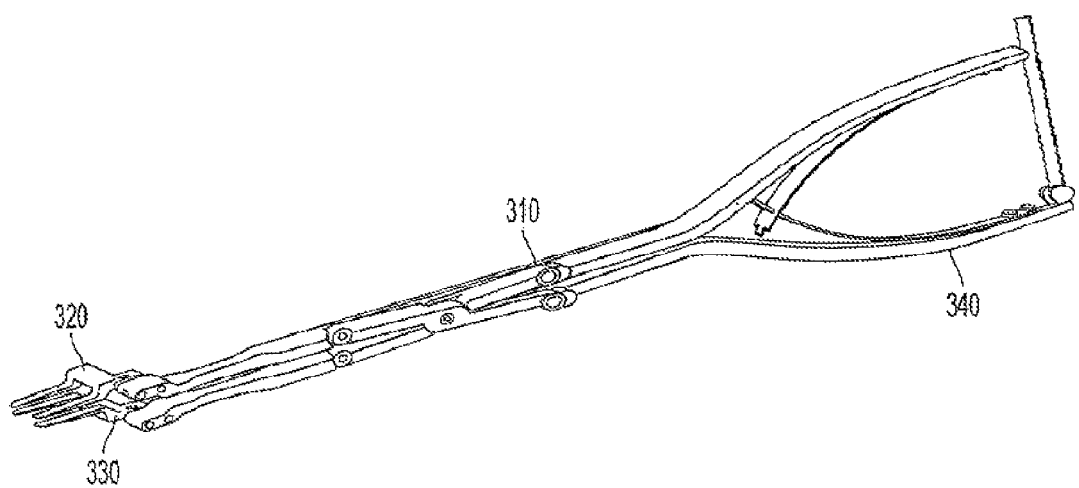
FIG. 27 provides an isometric view of the parallel distraction instrument 310 illustrating the grasping end 340 or handle of the instrument.
Figure 28:
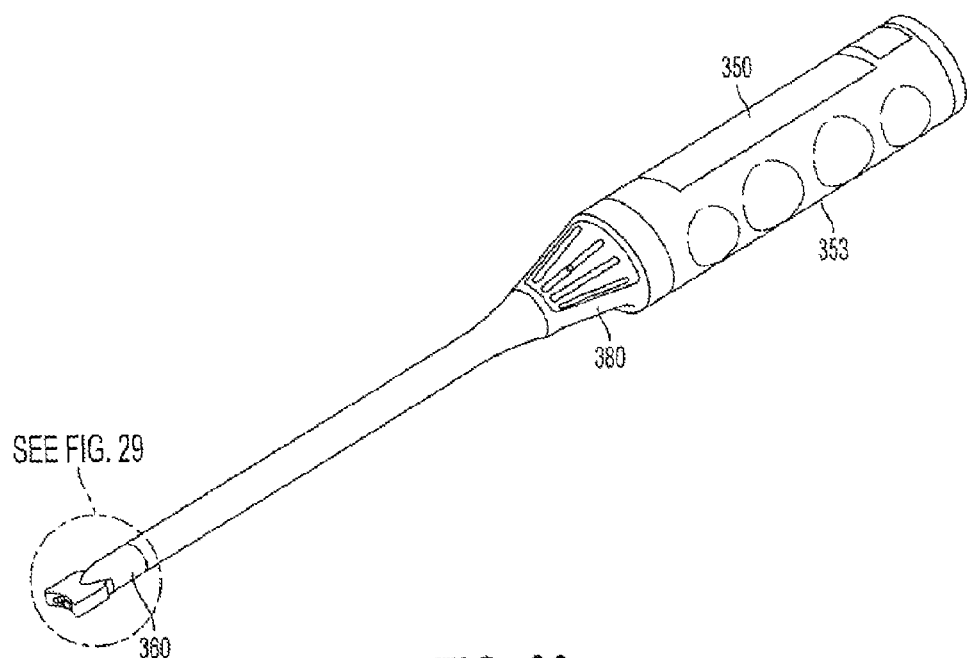
FIG. 28 provides an isometric view of one embodiment of the implant insertion tool 350.
Figure 29:
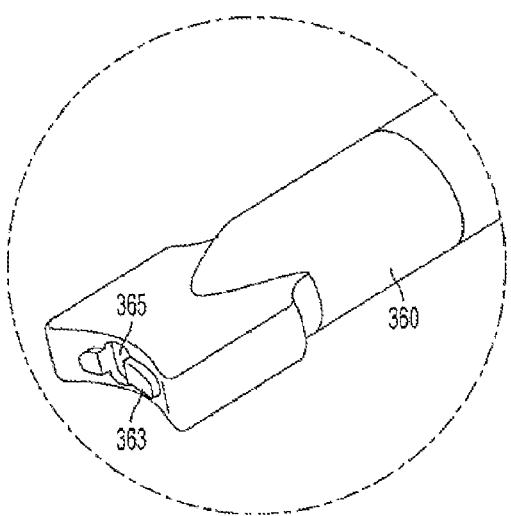
FIG. 29 provides a detailed view of the tip of the implant insertion tool 350.

FIGS. 23 through 27 illustrate various aspects of the parallel distraction instrument 310 of the present invention. Parallel distraction instrument 310 is suitable for the insertion of the ALIF implant of the present invention. The instrument 310 includes a pair of upper 320 and lower 330 forks that mate with the guide rails of the ALIF implant. For example, FIGS. 23 and 24 show instrument 310 engaging implant 130 via upper fork 320 engaging guide rails 147 on the top surface 140 of implant 130 and lower fork 330 engaging guide rails 157 on the bottom surface 150 of implant 130. Once instrument 310 holds the implant securely in place, the surgeon can insert the implant into the intervertebral space. Upon insertion of the instrument 310 with the implant, the handle 340 (see FIG. 27) of instrument 310 is depressed to actuate the two pairs of forks 320 and 330 in a parallel manner. In an alternate embodiment, a further insertion tool may slide between instrument 310 to place the implant in the intervertebral space. Instrument 310 further includes a scissor hinge and ratchet catch to allow for faster actuation than traditional screw style stops of the prior art and a faster release. Once instrument 310 is actuated, a device of the type shown in FIGS. 28-32 can pass through forks 320 and 330 and screw into opening 185 of the implant.

FIGS. 28 through 31 illustrate various features of an implant insertion and impactor tool 350. The tool 350 may be suitable for the insertion or removal of the cervical, ALIF, and PLIF implants of the present invention. Accordingly, the dimensions of tool 350 may vary depending upon the implant being inserted. Tool 350 includes a tip 360 that is comprised of a shock absorbing material that can withstand impact, such as a RADEL® tip and a sturdy body comprised of a material such as metal and a gripping handle 353. Tip 360 can be modular so that it is removable from the body of tool 350. Tip 360 has a projection 363 that mates with the anti-rotation convexity of the implant. The tip 360 further includes at least one opening 365, preferably a central opening that allows a "guide wire" with a threaded tip 370 to advance. In certain embodiments, threaded tip 370 advances through opening 365 upon rotation of the advancer 380 adjacent to the tool handle 353 (see FIGS. 28 and 30). Both the threaded tip 370 and projection 363 on the tool tip 360 mate with the threaded opening and anti-rotation convexity of the implant to allow for insertion or removal of the implant.

Figure 31:
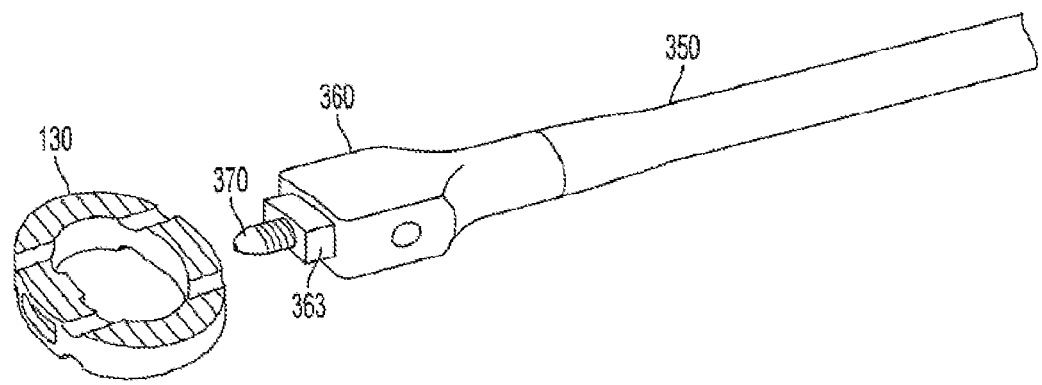
FIG. 31 provides a detailed, isometric view of the implant insertion tool 350 about to engage the ALIF implant 130.
Figure 31A:
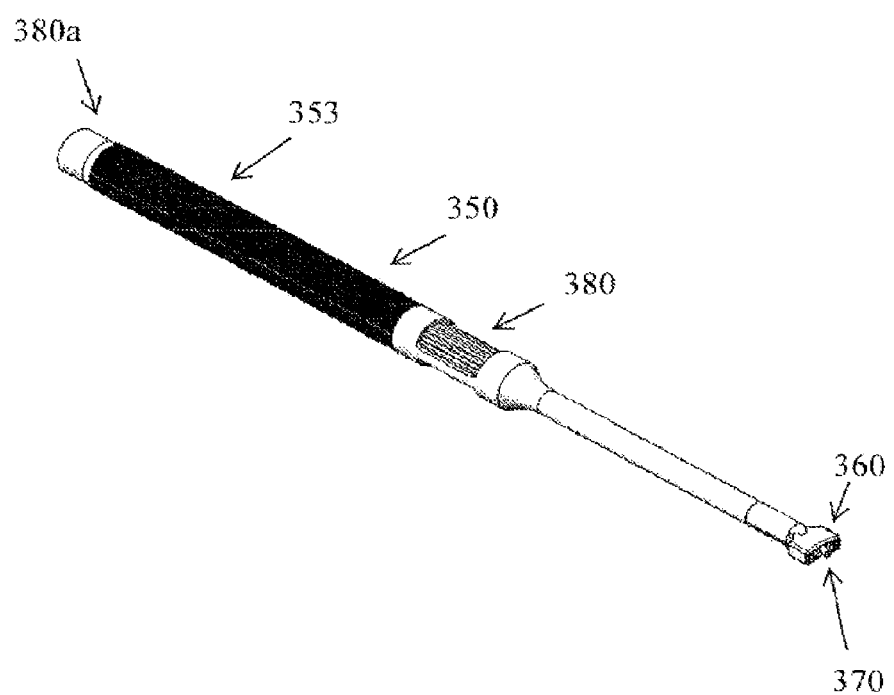

FIG. 31a shows an isometric view of another embodiment of the implant insertion tool 350 featuring a threaded tip that can be advanced via either rotation of the advancer 380 or of the rotatable end knob 380a.

Figure 32:
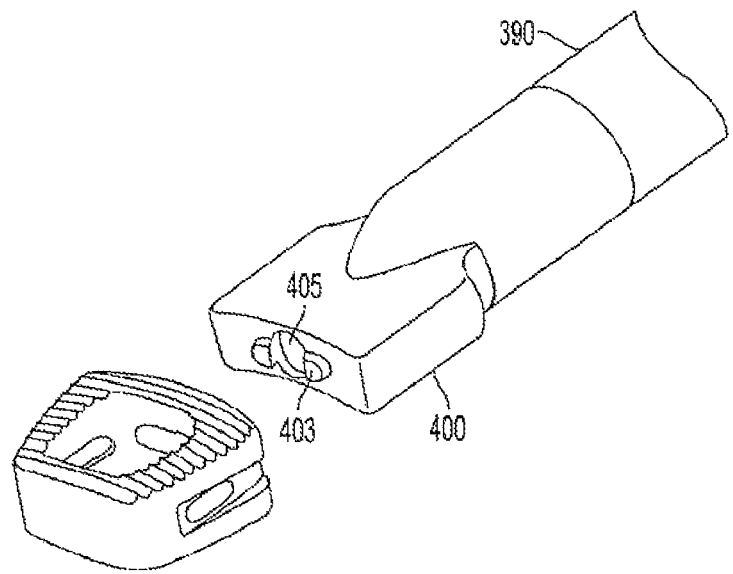
FIG. 32 provides an isometric view of implant insertion tool 390 prior to engaging cervical implant 10.
Figure 33:
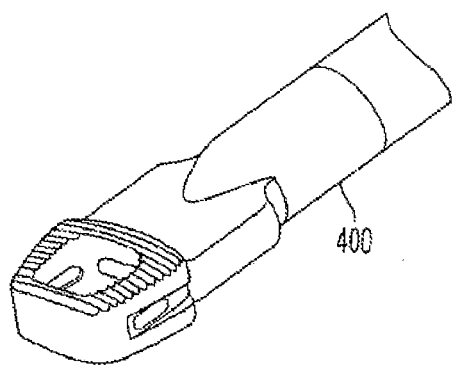
FIG. 33 provides an isometric view of implant insertion tool 390 engaging cervical implant 10.
Figure 34:
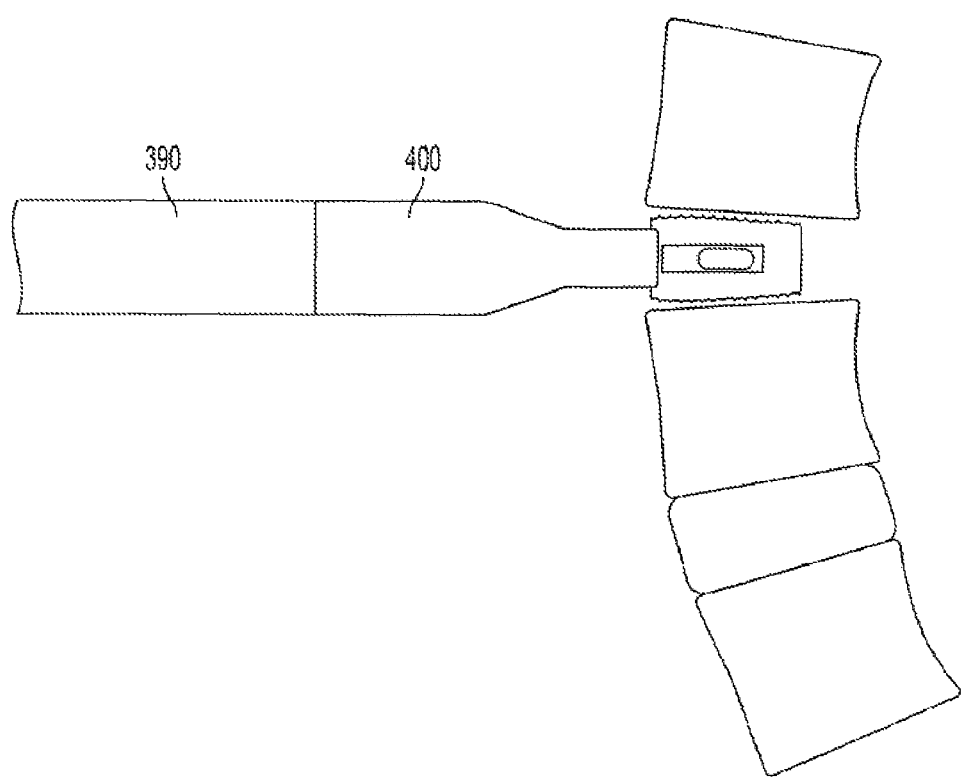
FIG. 34 provides a side view of implant insertion tool 390 inserting cervical implant 10 between two vertebral bodies.

FIGS. 32 through 34 illustrate various features of another embodiment of an insertion and impaction tool 390 of the present invention. Tool 390 mates flushly with the implant face and allows for impaction at the opposite end of the tip. Similar to tool 350, tool 390 has a tip 400 that is comprised of a shock absorbing material such as RADEL® and a sturdy body which is comprised of a metal and a gripping handle. Tip 400 has a projection 403 that mates with the anti-rotation convexity of the implant. Tip 400 may further include at least one opening 405, preferably a central opening, that allows a "guide wire" with a threaded tip to advance.

Figure 30:
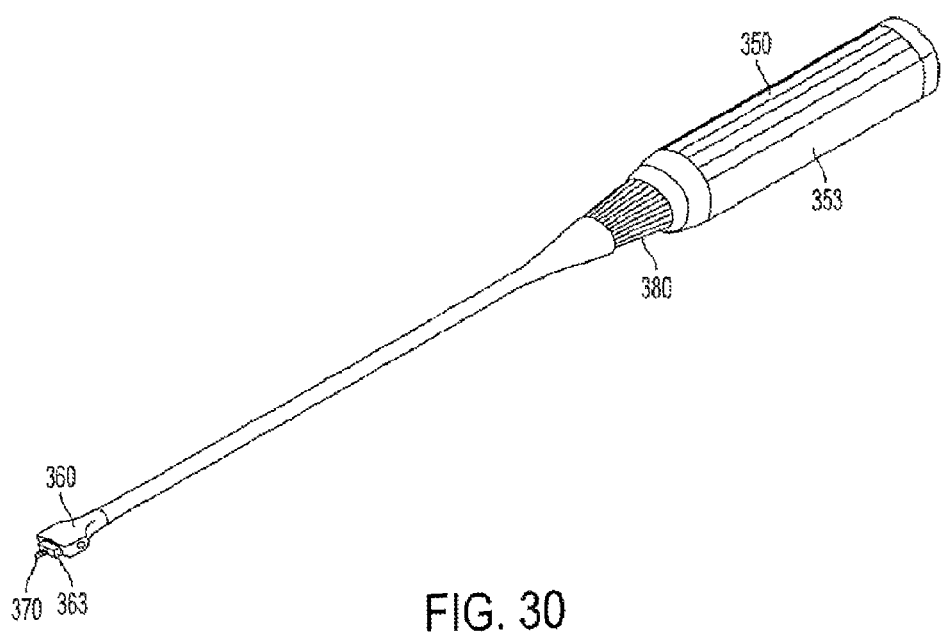
FIG. 30 provides an isometric view of another embodiment of the implant insertion tool 350 featuring a threaded tip.
Figure 35:
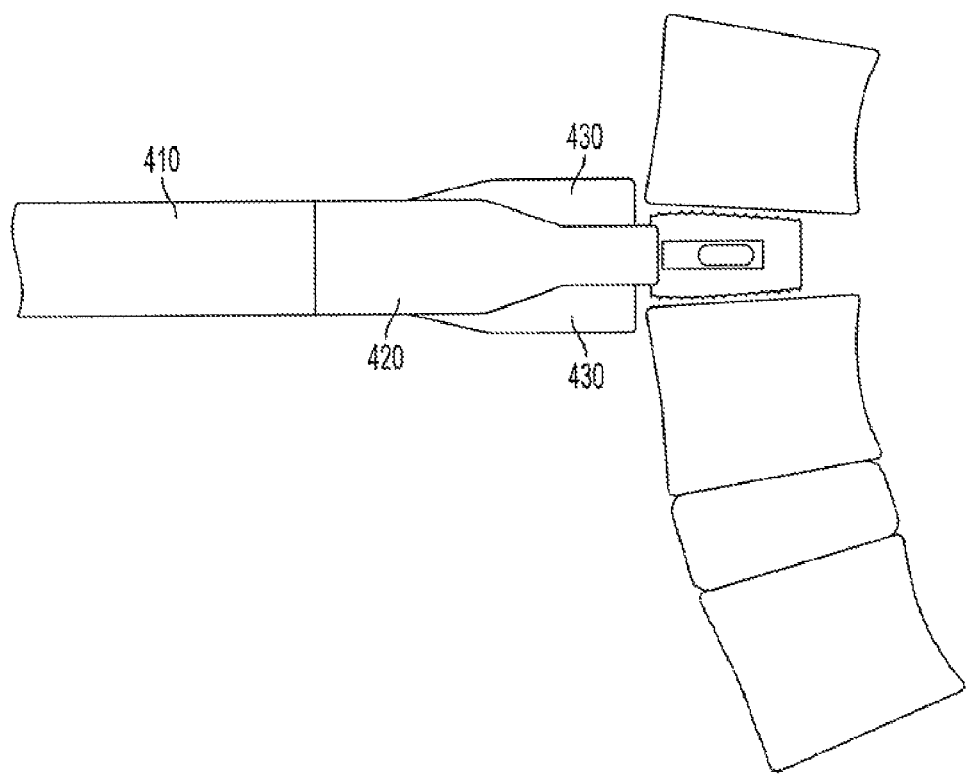
FIG. 35 provides a side view of another embodiment of the implant insertion tool 410 inserting the cervical implant 10 between two vertebral bodies.

FIG. 35 illustrates an alternate embodiment of the implant insertion and impaction tool 410 of FIG. 30 that includes a limiting impaction tip 420. Limiting impaction tip 420 has stops 430 that allow the surgeon to gauge how far tip 420 and the implant is displaced in the anterior to posterior direction with respect to the vertebral bodies. The height of stops 430 in a vertical direction may be any height that prevents tool 410 from going in-between adjacent vertebral bodies. The limiting impaction tip 420 may be modular or removable from tool 410. Tip 420 may be made with a set stop length that ranges between about 2 mm to about 4 mm to allow the surgeon to gauge how far into the intervertebral space the implant is being inserted.

FIGS. 36 through 39 illustrate various aspects of forceps 440 of the present invention that may be used for insertion of implants, such as the cervical implants 10 of the present invention. Forceps 440 may be used to as an alternative to the insertion and impaction tools 350 and 390 of the present invention. Forceps 440 are generally scissor-like in shape and have two openings at the handle to accommodate the fingers of the surgeon. Forceps 440 may include nubs 450 on the inside of each tip 445 for mating with the openings on the medial and lateral sides of the implant 10. Tip 445 may further include shock absorbing pads 460 that are comprised of a material such as RADEL® to cushion the implant if the forceps 440 are also used for impaction.

Figure 40:
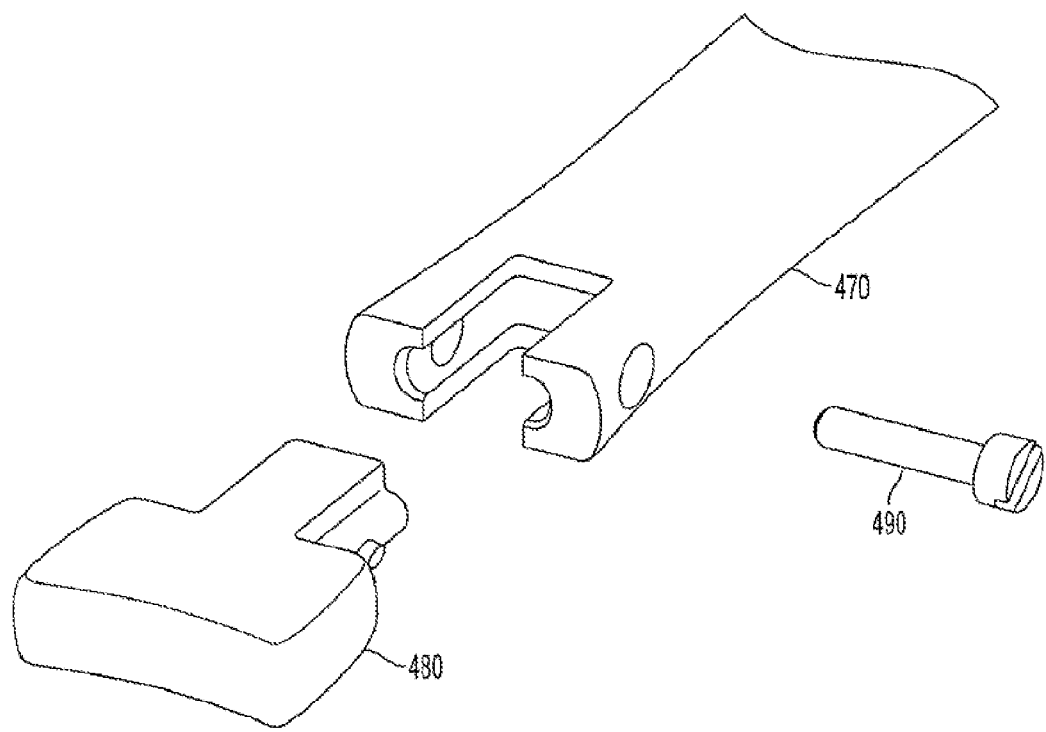
FIG. 40 provides an exploded, isometric view of one embodiment of the insertion tool 470 of the present invention.
Figure 41:
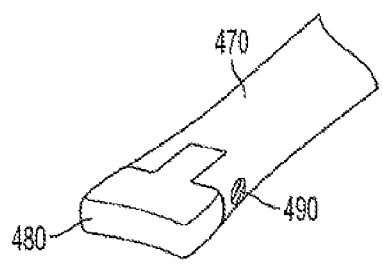
FIG. 41 provides an isometric view of the assembled insertion tool 470.
Figure 42:
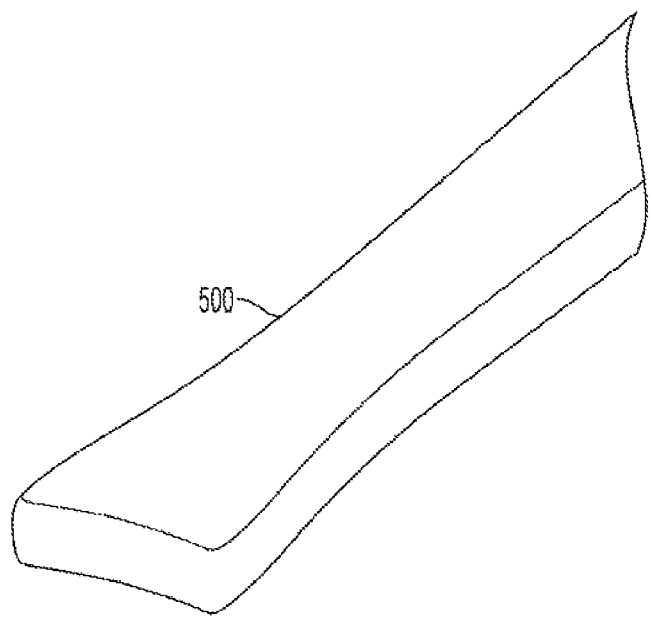
FIG. 42 provides an isometric view of another embodiment of the insertion tool 500.

FIGS. 40 and 41 provide an exploded and isometric view of an insertion and impaction tool 470 that is suitable for use with any of the implants of the present invention. Tool 470 may be provided with a modular tip 480 that may be made of a shock absorbing material, such as but not limited to RADEL®, that is secured to tool 470 with a fastener 490 or other means. This allows tip 480 to be replaced after wear due to repeated use. Alternatively, the insertion and impaction tool may be integral with the tool body and handle such as tool 500 in FIG. 42. Preferably the tip of tool 470 or 500 is rounded and smooth-edged. In use, the impactor and insertion tool 500 is placed flush against the implant 10 (see FIG. 43) and then tapped via impaction hammer 510 to adjust the position of the implant (see FIGS. 44 through 47c). The impaction and insertion tool allows for the surgeon to focus on various contact spots such as the medial aspect, the lateral aspect or the center of the implant for medial, lateral, and the anterior to posterior positioning of the implant (see FIGS. 45 through 47c).

Figure 47D:
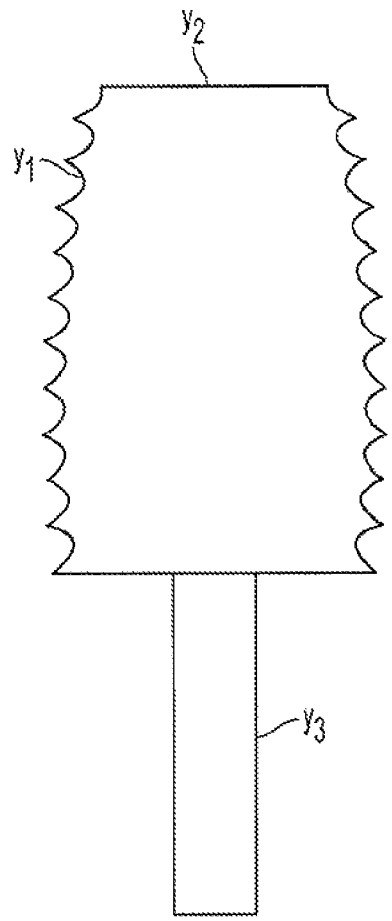
FIG. 47d provides a side view illustrating a rasp instrument y1 of the present invention to be used to shape the endplate prior to implant insertion.

FIG. 47d shows a side view of a rasp y1 of the present invention used in the preparation of the endplate. The rasp y1 is in the shape of the implant being inserted so as to contour the endplates to accommodate the eventual implant being inserted and provide for good contact between the endplate bone and the implant. Although FIG. 47d shows a rasp y1 with a headpiece y2 in the shape of a cervical type implant, it should be understood that the headpiece y2 of the rasp y1 could be in any implant shape including the ALIF, PLIF and TLIF types disclosed herein. Rasp y1 also includes a handle y3, which may be integral to or a modular with the headpiece y2, for gripping and manipulating the rasp y1. FIGS. 48 and 49 provide an isometric and detailed isometric view of trial tools 520 with plugs 530 of the present invention. Tool 520 is used after preparation of the intervertebral space and prior to insertion of the implant to determine the size of the implant to insert. Plugs 530 can be modular (i.e., fasten or snap onto the end of tool 520) or be integrated into tool 520. Plugs 530 are generally the same size and shape of the implant. In FIG. 49, plug 530 may be similar in size and shape to the cervical implant 10 of the present invention.

Figure 50:
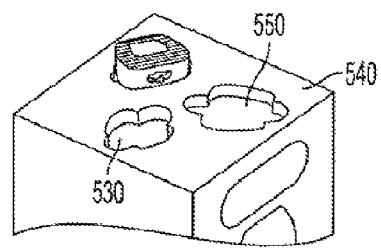
FIG. 50 provides an isometric view of one embodiment of the graft impaction block 540 of the present invention.
Figure 51:
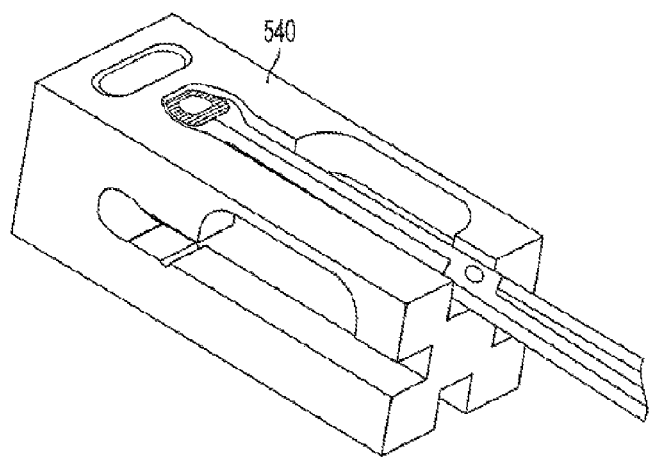
FIG. 51 provides an isometric view of the graft impaction block 540 and the forceps tool 440 engaging the cervical implant 10.
Figure 52:
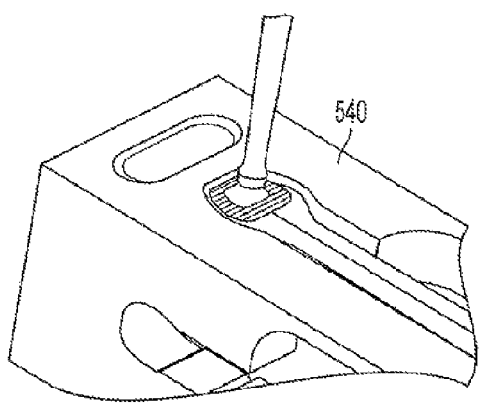
FIG. 52 provides an isometric view of the graft impaction block 540 and the insertion of graft material into the cervical implant 10.

FIGS. 50 through 52 illustrate various aspects of the view of graft impaction block and implant/tool holder 540 of the present invention. Graft impact block 540 comprises a plurality of recesses 550 of various sizes to accommodate various sizes of implants of the present invention. Block 540 allows other agents-such as graft material to be packed into the hollow interior of the implant.

Figure 53:
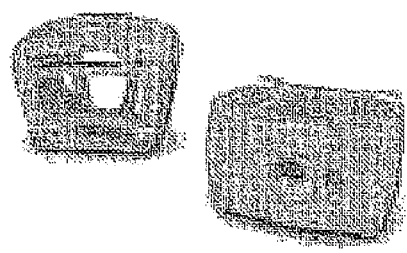
FIG. 53 is an example of another embodiment of a shaped body in the form of a vertebral body spinal implant according to the present invention.

FIG. 53 depicts another embodiment of a spinal implant made from the material of the present invention showing the flexibility of the bioactive composite material to be machined or molded into an intricate design.

FIG. 54 is an example of another embodiment of a vertebral body spinal implant made from the material of the present invention and including a graft material in the center of the implant. In this embodiment, the composite ring has a first portion 210a comprised of the bioactive composite material (e.g., biocompatible polymer and bioactive glass) of the present invention and a second portion 212a comprised of an additional material, preferably a porous, inorganic calcium phosphate agent.

Figure 55:
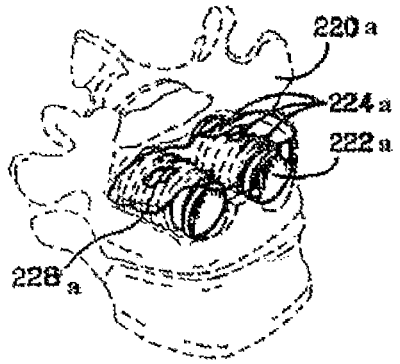
FIG. 55, FIG. 56, FIG. 57 show various bone dowels for spinal fusion in place in the vertebral body (vertebral body shown in phantom).
Figure 56:
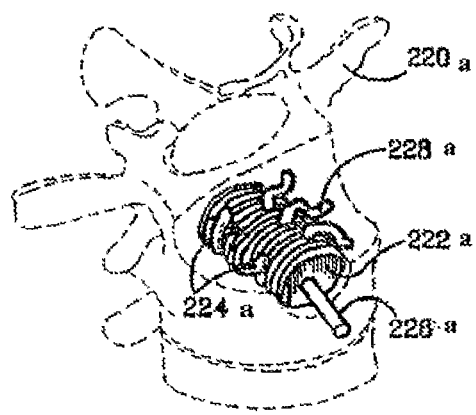
Figure 57:
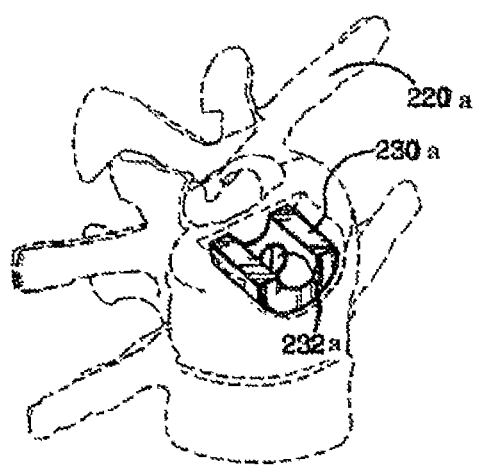

FIG. 55, FIG. 56, FIG. 57 show various bone dowels for spinal fusion in place in the vertebral body (vertebral body shown in phantom). The bone dowel of FIG. 55 has a plurality of ports, some of which are shown 224a. Hardenable material such as bone augmentation materials and bone cement may be injected into the dowel, emerging from the ports to partially surround the dowel 228a. FIG. 56 depicts another bone dowel for spinal fusion. The end of an injection device or syringe 226a is shown. Bone augmentation material 224a is shown emerging from access ports 228a in the dowel.

Bone Repair

In other embodiments of the present invention, the composite shaped body may be used in a variety of orthopaedic procedures involving bone repair and restoration. Long bones are comprised of the both cortical and cancellous (metaphyseal) bone. The present invention composite may be formed into a cortical bone sleeve via machining or other means. Orthopaedic appliances such as joints, rods, pins, suture fasteners, anchors, repair devices, rivets, staples, tacks, orthopaedic screws and interference screws, and a number of other shapes may be formed from the bioactive composite material in and of itself or used in conjunction with conventional appliances that are known in the art. Such bioactive, composite shaped bodies can be used in conjunction with biocompatible gels, pastes, cements or fluids and surgical techniques that are known in the art. Thus, a screw or pin comprised of the present invention bioactive composite material can be inserted into a broken bone in the same way that metal or polymeric screws and pins are currently inserted. The bioactivity of the material will give rise to osteogenesis with beneficial medical or surgical results.

The bioactive composite material of the present invention may also be shaped into other orthopaedic devices including, but not limited to, sheets, bone plates and bone plating systems, bone scaffolds, bone graft substitutes, bone dowels and other devices useful in fixing bone damaged by, for example, trauma or surgery.

Figure 58:
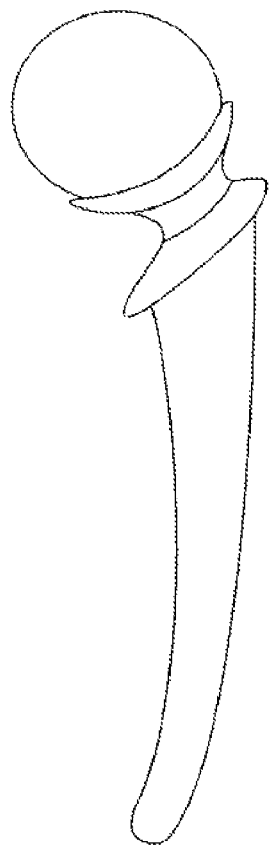
FIG. 58 is an example of one embodiment of a shaped body in the form of an orthopaedic hip implant according to the present invention.

In some aspects of the present invention, the composite shaped body may be used in orthopaedic procedures such as total hip arthroplasty and fracture fixation. Total hip arthroplasty is a surgical procedure in which the hip joint is replaced by a prosthetic. Such joint replacement surgery generally is conducted to relieve arthritis pain or fix severe physical joint damage as part of hip fracture treatment. The hip joint comprises the femur and acetabulum. The femur terminates at the proximal end in a femoral head of generally spherical shape. The acetabulum cooperates with the femur by serving as a cavity that allows for articulation with the femoral head. With a hip implant, the femoral head is excised or resected to expose the femoral intramedullary canal. The stem of the hip implant is surgically implanted within the femoral intramedullary canal for fixation thereto either by bone cement, bone augmentation material or by a press fit. The proximal end of the hip implant terminates in a spherical head. A cup assembly is carried on the spherical head for engagement and articulation with the acetabulum. FIG. 58 depicts an illustrative embodiment of an orthopaedic hip implant comprising the bioactive and biocompatible materials of the present invention. The implant may in part or whole be comprised of the composite.

Figure 59A:
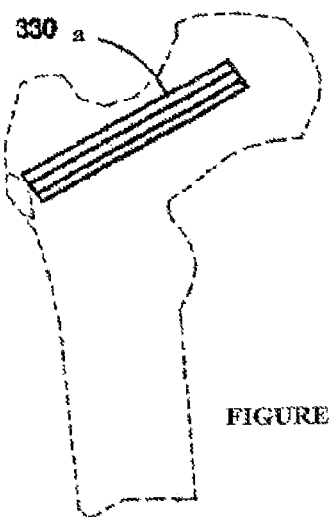
FIGS. 59a and 59b depict insertion of femoral hip dowels into a femur (femur shown in phantom in each figure).
Figure 59B:
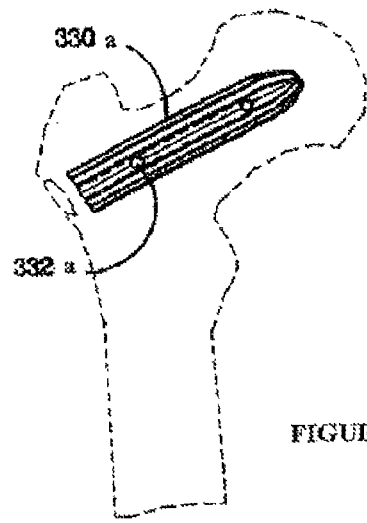
Figure 60A:
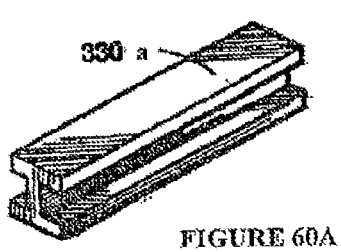
FIGS. 60a through d depict different forms of dowels for orthopaedic use.
Figure 60B:
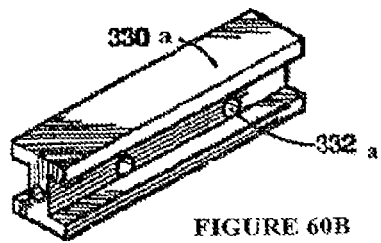
Figure 60C:
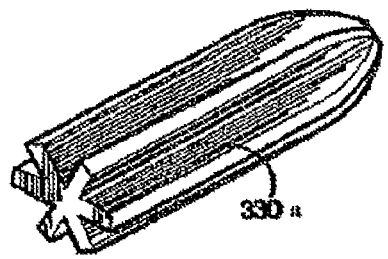
Figure 60D:
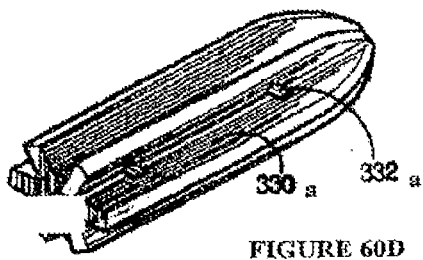

FIGS. 59a and 59b depict insertion of femoral hip dowels 330a into a femur, shown in phantom, requiring restoration. Access ports 332a permit the injection of hardenable material, such as bone augmentation material or bone cement, into the dowel and, via the ports, around the dowel to effect fixation in the femur head. FIGS. 60a through d are different forms of dowels 330a of the type useful for hip or other reconstruction. Optional access ports 332a are present in FIGS. 60b and 60d.

Figures 61A, 61B:
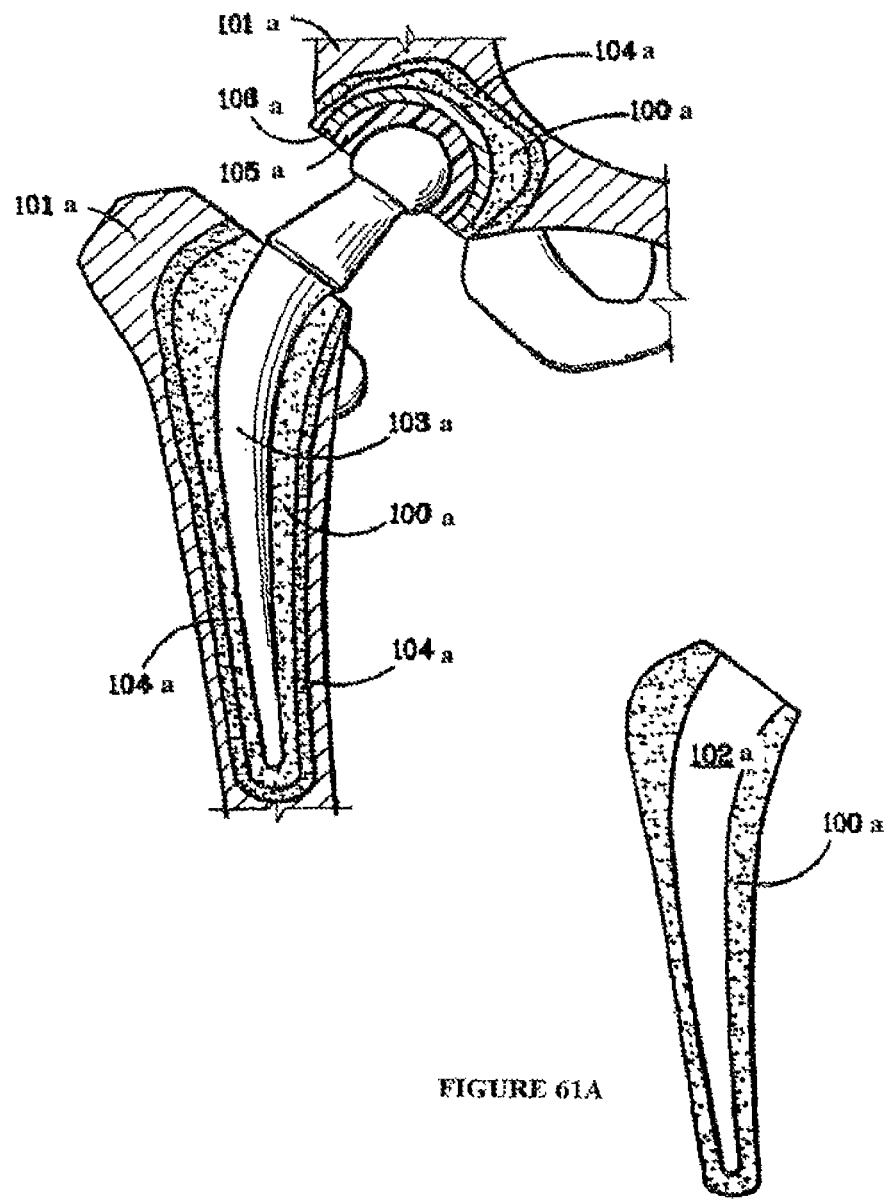
FIGS. 61a and 61b illustrate an embodiment of the material of the present invention shaped into a sleeve form and used for impaction grafting to accommodate an artificial implant said sleeve form being screwed, bonded, pinned or otherwise attached in place.

FIGS. 61a and 61b depict the use of the present invention material as a receptacle sleeve 100a that is inserted into the body to facilitate a bipolar hip replacement. Cavity 102a is machined into the sleeve 100a to accommodate the insertion of a ball joint implant or prosthesis 103a. An orthopaedic surgeon drills a cavity or furrow into the bone 101a to receive sleeve 100a. Sleeve 100a is then affixed to the surrounding bone via a bone augmentation material or bone cement layer 104a or other means. On the acetabular side, a femoral head articulation surface 106a is maintained within a prepared cavity via the material of the present invention 100a and a bone cement layer. A high molecular weight polyethylene cup or cup of similar type material, 105a is used to facilitate articulation with the head of the prosthesis 103a. The ball joint implant or prosthesis 103a is thus inserted into a cup 105a to facilitate joint movement.

Figure 62:
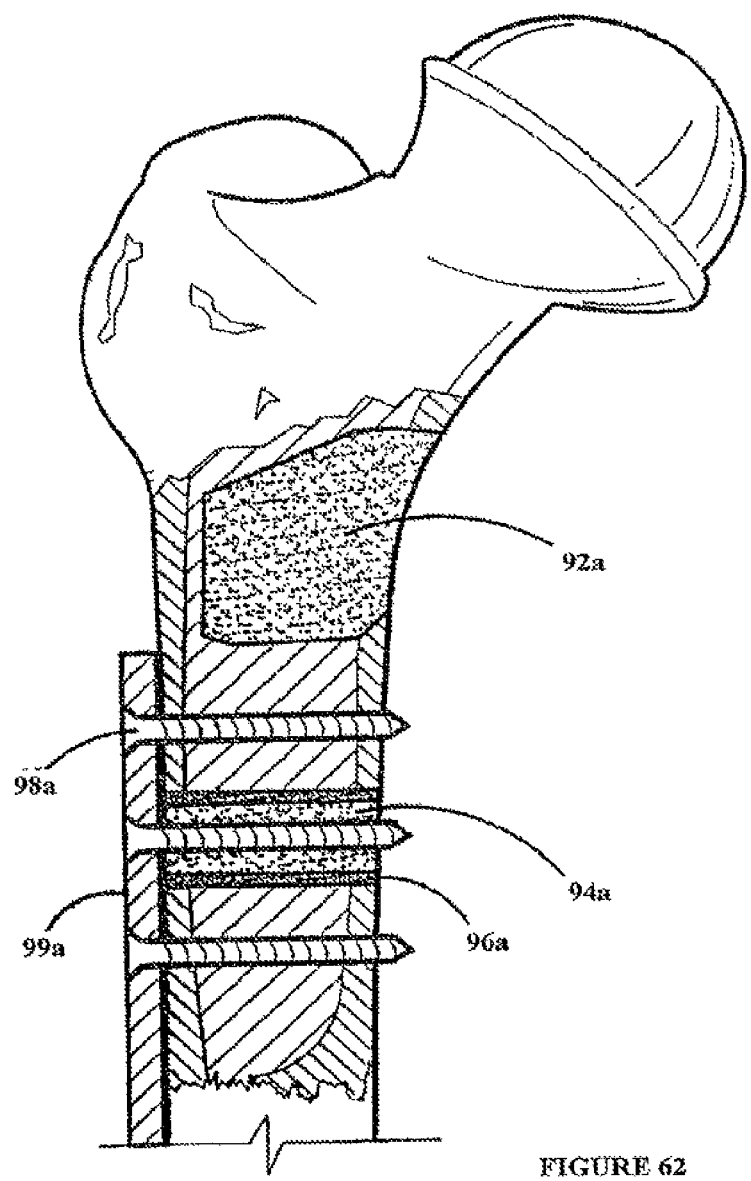
FIG. 62 illustrates an embodiment of the material of the present invention shaped into a block or sleeve form and used for the repair or replacement of bulk defects in bone, oncology defects or screw augmentation.
Figure 63:
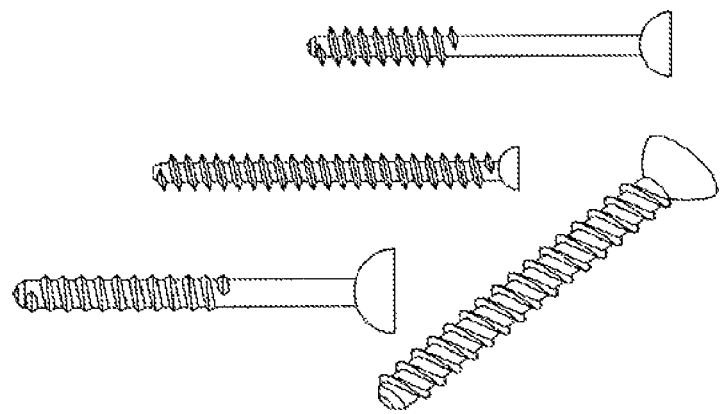
FIG. 63 is an example of one embodiment of a shaped body in the form of screws according to the present invention.
Figure 64:
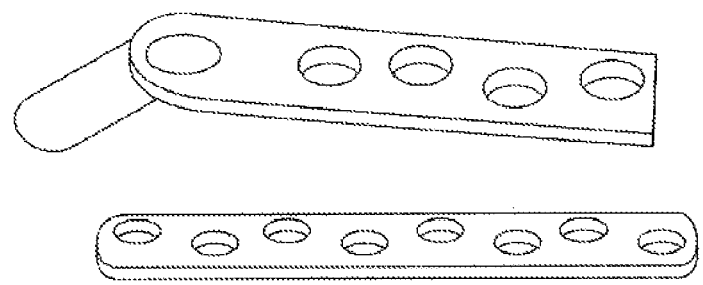
FIG. 64 is an example of one embodiment of a shaped body in the form of orthopaedic plates according to the present invention.

FIG. 62 shows the material within a human femur that is used as a block 92a for bulk restoration or repair of bulk defects in bone or oncology defects, or as a sleeve 94a for an orthopaedic screw, rod or pin 98a augmentation. Item 99a depicts an orthopaedic plate anchored by the orthopaedic device item 98a. Bone cement layer 96a surrounds and supports sleeve 94a in place. These screw, rod and plate devices may be made of medical grade metal or other material, or may be comprised of the bioactive composite material of the present invention. For instance, FIG. 63 depicts an illustrative embodiments of such bone screws comprising the bioactive and biocompatible materials of the present invention; and FIG. 64 depicts an illustrative embodiments of such bone plates comprising the bioactive and biocompatible materials of the present invention.

Figure 65A:
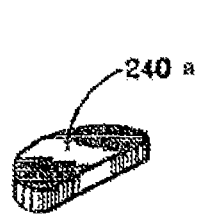
FIGS. 65a, 65b and 65c depict synthetic cortical vertebral spacers or interbody devices comprised of the material of the present invention.
Figure 65B:
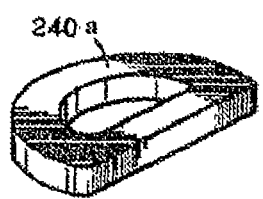
Figure 65C:
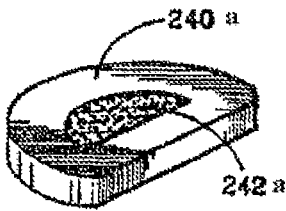

FIGS. 65a through c depict other synthetic cortical vertebral spacer or interbody device embodiments. Hard material, 240a preferably composite material in accordance with the invention, forms the spacers and rings. In some embodiments a plurality of regions form the shaped body as illustrated in FIG. 65c. The present invention bioactive composite material 240a forms an outer portion of the ring, while a porous agent, especially a porous calcium phosphate material 242a forms an inner portion of the body.

Figure 66A:
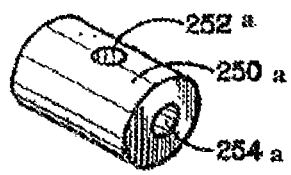
FIGS. 66a through c depict synthetic cortical bone dowels or interbody devices comprised of the material of the present invention.
Figure 66B:
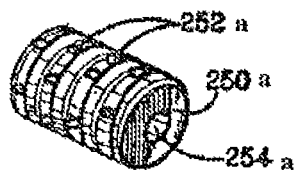
Figure 66C:
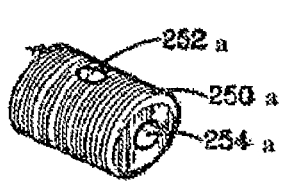
Figure 67:
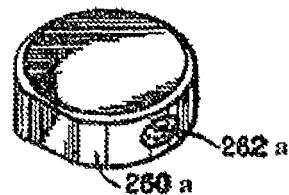
FIG. 67 is another form of synthetic cortical spacer comprised of the material of the present invention.

FIGS. 66a through c depict still other embodiments of synthetic cortical bone dowels or interbody devices 250a. The dowels may have access ports 252a for emergence of hardenable material when such material is injected into orifice 254a with a syringe device. The dowels and devices may be composite materials as set forth herein. FIG. 67 is another form of cortical spacer. The spacer has a relatively hard outer portion 260a formed of the present invention bioactive composite material along with a calcium phosphate derived (or similar agent) inner portion 262a.

Figure 68:
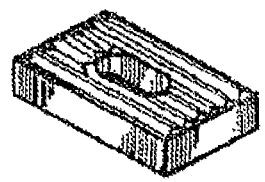
FIG. 68 is a synthetic cortical vertebral interbody device comprised of the material of the present invention.

FIG. 68 is a synthetic cortical vertebral interbody device of another form.

Figure 69:
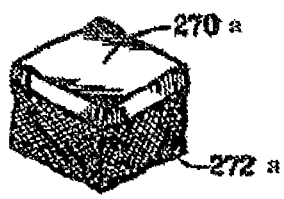
FIG. 69 is a synthetic shaped body for bone restoration. The bioactive composite of the present invention 270a is combined with a calcium phosphate portion 272a to give rise to a bioactive cortico-cancellous shaped body.

FIG. 69 depicts a synthetic cortico-cancellous defect filling form for bone restoration. The bioactive composite of the present invention 270a is combined with a calcium phosphate based portion or other similar type of osteoinductive agent 272a to give rise to another embodiment of a bioactive, composite shaped body.

Figure 70:
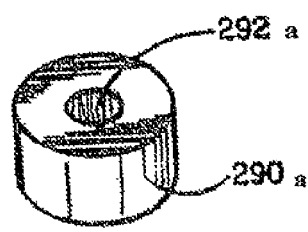
FIG. 70 is a synthetic cortical ring comprised of the material of the present invention.

FIG. 70 is a synthetic cortical ring. The bioactive composite of the present invention may have a central opening or the opening may be filled, e.g. with bone graft substitutes or osteoinductive agents. The ring may also have an inner portion formed from another agent.

Figure 71:
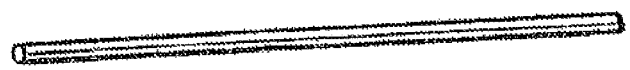
FIG. 71 is a synthetic cortical rod for orthopaedic restoration comprised of the material of the present invention.

FIG. 71 shows a synthetic cortical rod comprised of the bioactive composite material of the present invention for orthopaedic restoration.

Figure 72B:
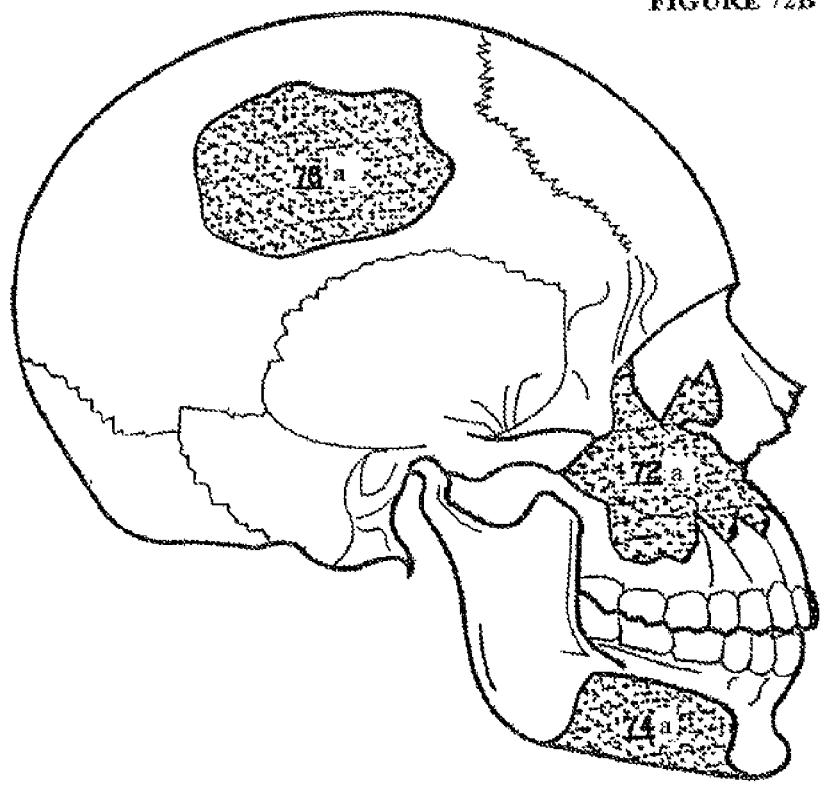
FIGS. 72a and 72b illustrate another embodiment of the present invention used as a cranio-maxillofacial, zygomatic reconstruction and mandibular implant.
Figure 72A:
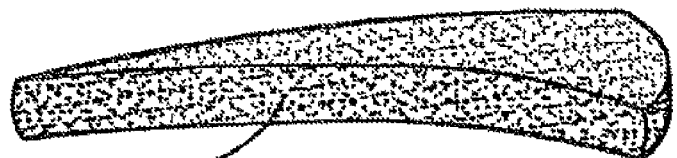

FIG. 72a shows the present invention material prepared in accordance with an embodiment of the present invention, which is machined or molded to patient specific dimensions. FIG. 72b depicts the use of the material that is formed into the shape of craniomaxillofacial implant 76a, a zygomatic reconstruction 72a, or a mandibular implant 74a.

Figure 73A:
FIGS. 73a and 73b illustrate one embodiment of the material of the present invention shaped into a block form and used as a tibial plateau reconstruction that is screwed, bonded, cemented, pinned, anchored, or otherwise attached in place.
Figure 73B:
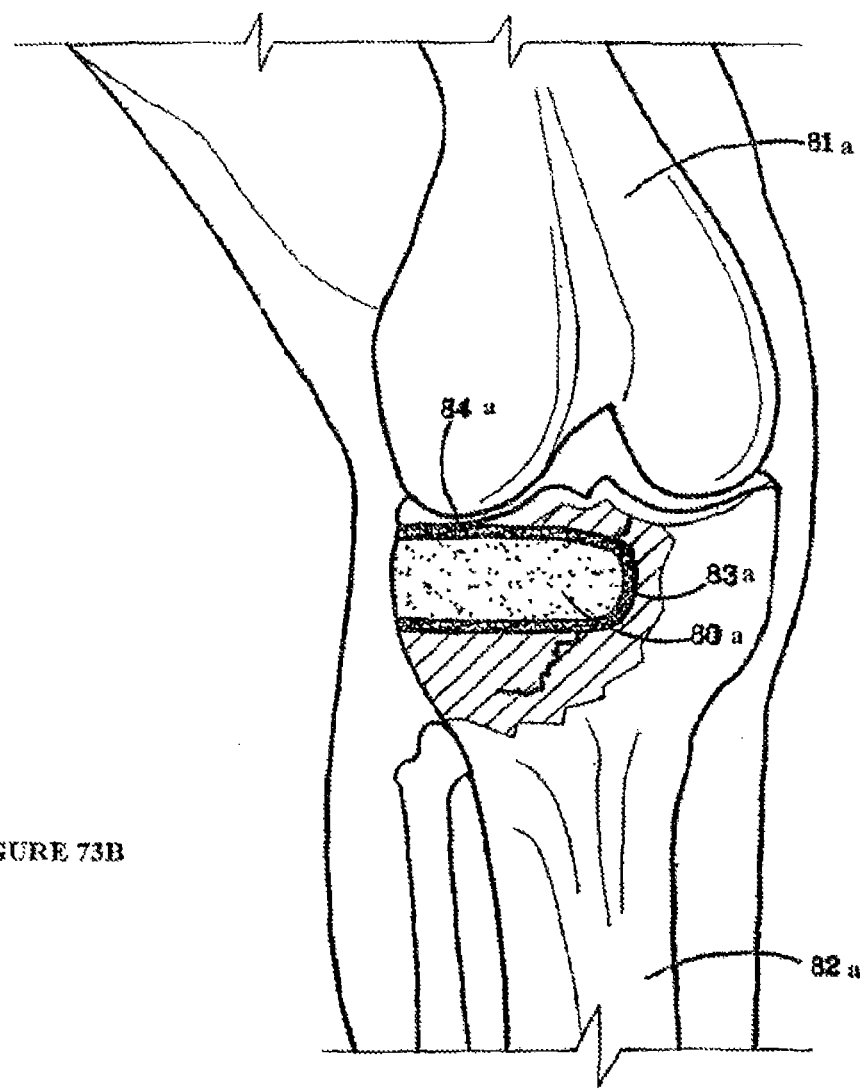

FIG. 73a depicts a plug 80a of the present invention material. FIG. 73b illustrates the plug 80a which is inserted into an excavation site 83a within a human knee, below the femur 81a and above the tibia 82a, for use in a tibial plateau reconstruction. Plug 80a is held in place or stabilized via a bone cement layer 84a.

Dental Implants

Figure 74:
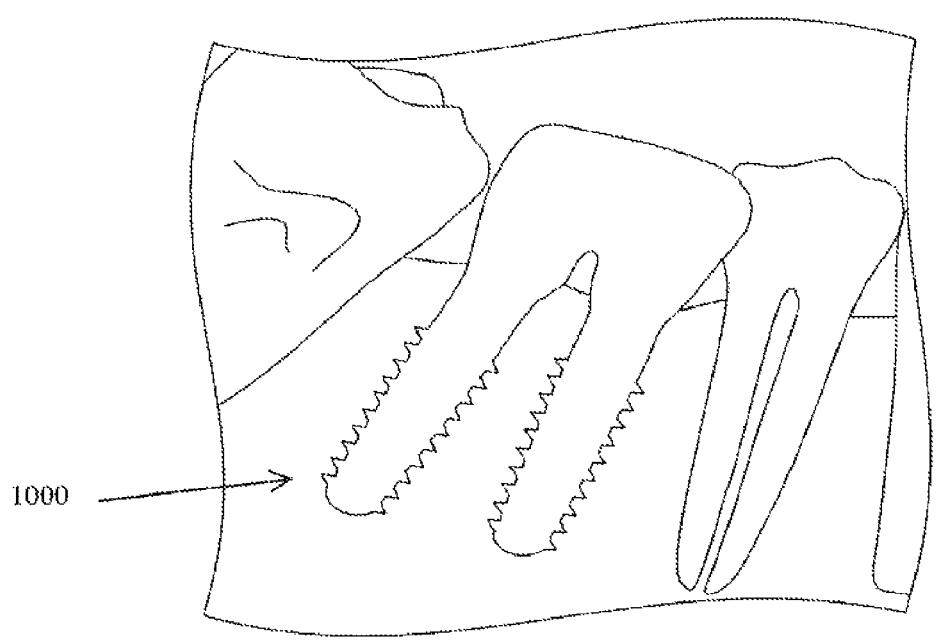
FIG. 74 is an example of one embodiment of a shaped body in the form of a dental implant according to the present invention.

The bioactive composite may also be formed into the shape of a craniomaxillofacial implant or may find particular utility in a variety of dental procedures including use as a dental implant. Dental implants 1000 may be placed into either the maxilla or mandible to form a structural and functional connection between the living bone (FIG. 74).

Figure 75A:
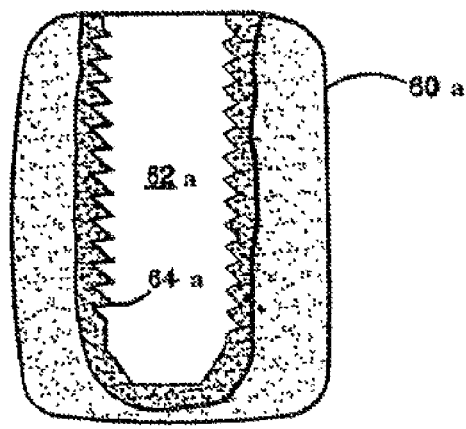
FIG. 75a and FIG. 75b illustrate one embodiment of the present invention used as a sleeve in which a tooth is screwed, bonded, cemented, pinned, anchored, or otherwise attached in place.
Figure 75B:
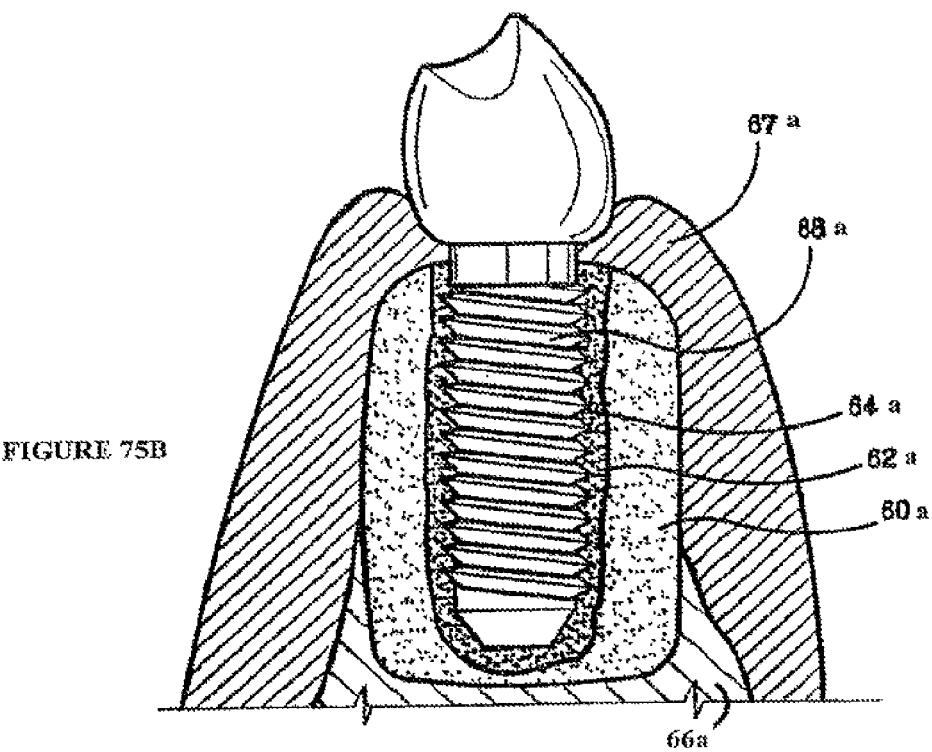

FIG. 75a shows the material of the present invention formed into the shape of a sleeve 60a. Item 62a depicts the excavated cavity which can be formed via machining or other means. Item 64a presents a plurality of threads which can be coated with bone cement or a variety of osteoinductive and/or osteoinductive materials. FIG. 75b shows the sleeve 60a inserted into the jaw bone 66a and gum 67a. The sleeve 60a may be fixed in place via pins, bone cement, or other mechanical means of adhesion. An artificial tooth or dental implant 68a can then be screwed into sleeve 60a by engaging threads 64a.

The shaped bodies can be modified in a number of ways to increase or decrease their physical strength and other properties so as to lend those bodies to still further modes of employment. Overall, the present invention is extraordinarily broad in that shaped bodies may be formed easily, under carefully controllable conditions, and with enormous flexibility. In conjunction with certain embodiments of the present invention, shaping techniques are employed on the bioactive composite shaped bodies of the present invention. Thus, such bodies may be machined, pressed, stamped, drilled, lathed, or otherwise mechanically treated to adopt a particular shape both externally and internally. Preformed shapes may be formed in accordance with the invention from which shapes may be cut or formed. For example, an orthopaedic sleeve for a bone screw may be machined from a block of material made hereby, and the same tapped for screw threads or the like.

In addition to the shaped implants described above, certain aspects of the present invention provide for kits that contain sterile shaped implants within sterile packaging alongside appropriate instrumentation for inserting or implanting the shaped implant.

Throughout this disclosure, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

EXAMPLES

Additional objects, advantages, and novel features of this invention will become apparent to those skilled in the art upon examination of the following examples of the invention. The examples are included to more clearly demonstrate the overall nature of the invention. The examples are exemplary, not restrictive, of the invention.

Bioactivity

Samples were mixed in a solid state, without the addition of a solvent. The materials were dry mixed thoroughly by tumbling on rollers for about two hours until a homogeneous mixture was observed. The mixed composite was added to a barrel and plunger extruder set to an adequate temperature to melt the polymer. The barrel and plunger extruder was used to fill a pre-heated disc mold. The molded sample was removed and a hole-saw was used to core out a smaller circular-disc sample. This sample was then milled on the top and bottom to further expose the bioactive glass.

Molded samples were made from various composites of PEEK and Combeite bioactive glass-ceramic at various particle sizes according to the process described above. Both discs (diameter=12 mm) and cylinders (diameter=5-6.5 mm) were used for testing. The samples were suspended in simulated body fluid at 37° C. for 3, 7, 14, 21, and 28 days.

Figure 76:
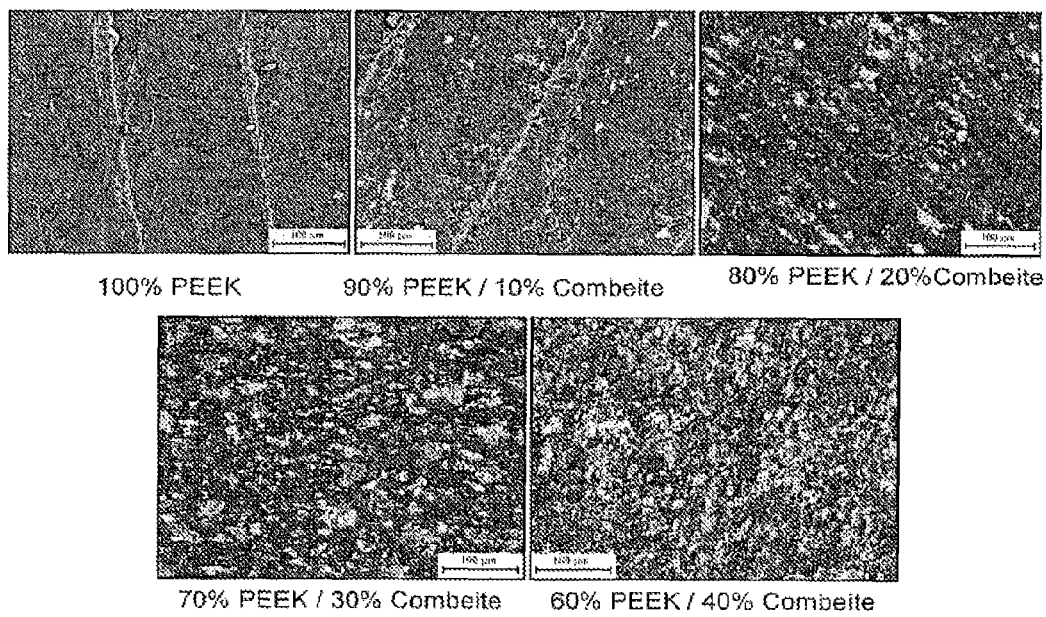
FIG. 76 depicts a series of scanning electron microscope (SEM) photographs of various sample embodiments of the present invention comprising PEEK and Combeite glass-ceramic (<53 μm) prior to immersion in simulated body fluid (SBF).
Figure 77:
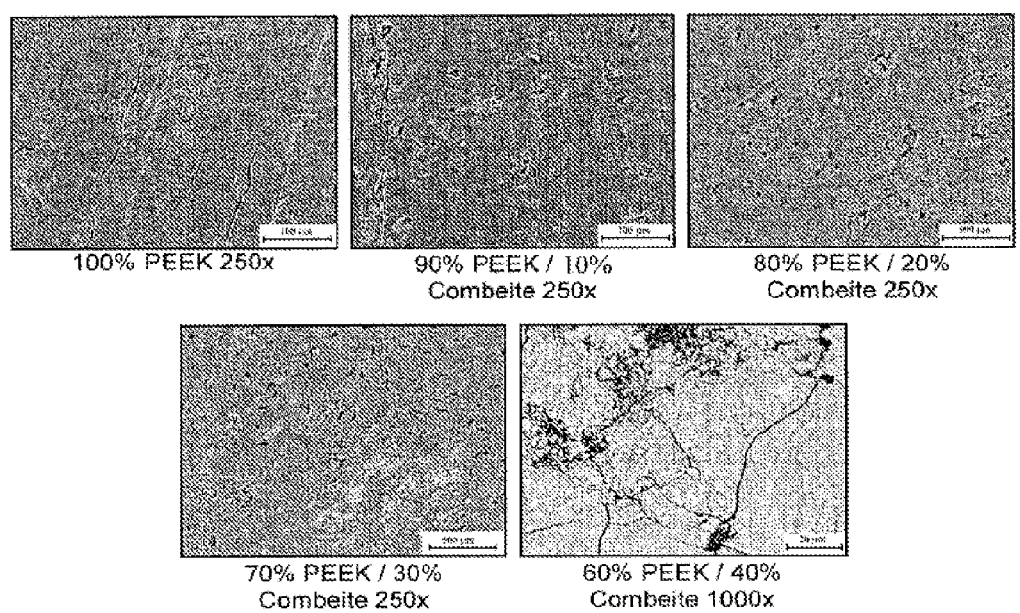
FIG. 77 depicts a series of SEM photographs of the samples shown in FIG. 76 after immersion in SBF for 3 days.
Figure 78:
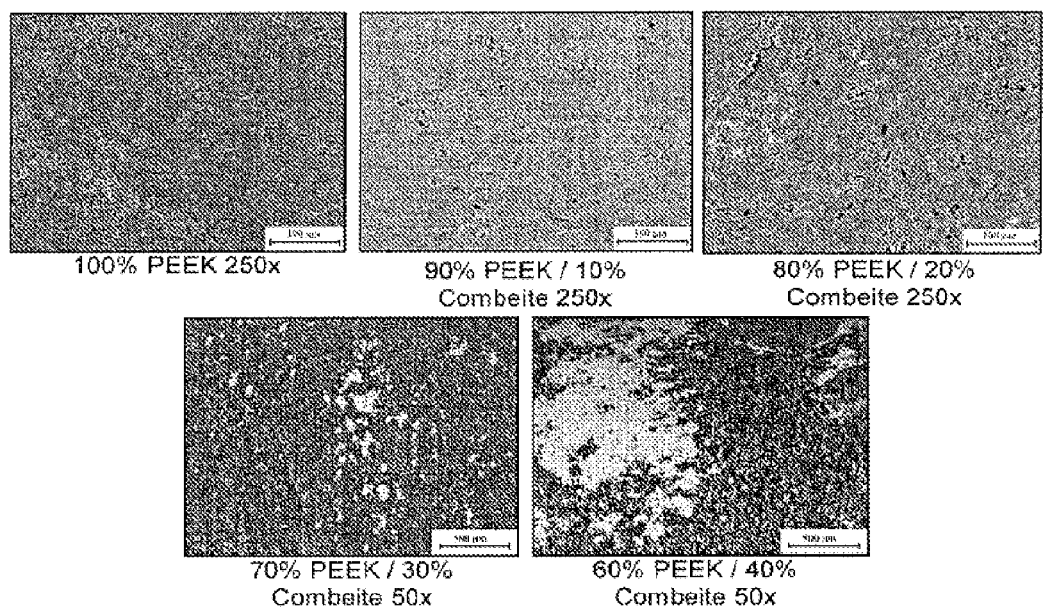
FIG. 78 depicts a series of SEM photographs of the samples shown in FIG. 76 after immersion in SBF for 7 days.
Figure 79:
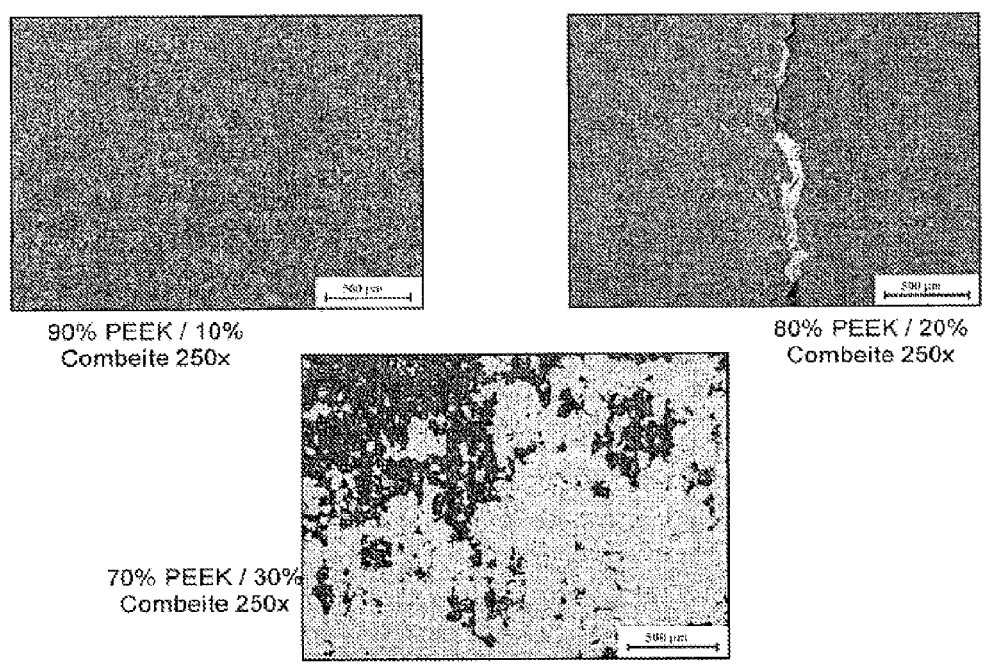
FIG. 79 depicts a series of SEM photographs of certain of the samples shown in FIG. 76 after immersion in SBF for 14 days.
Figure 80:
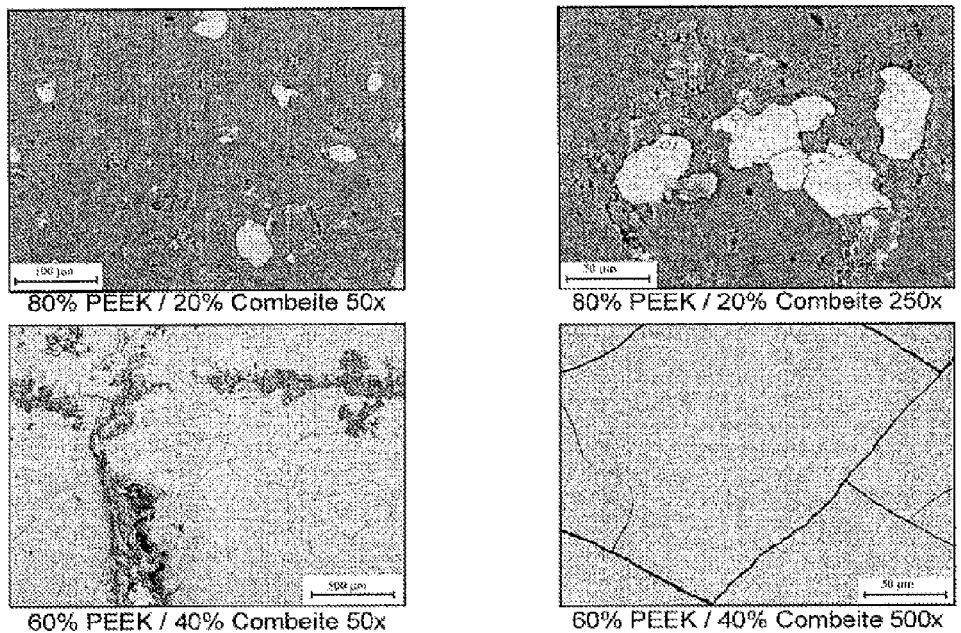
FIG. 80 depicts a series of SEM photographs of certain of the samples shown in FIG. 76 after immersion in SBF for 21 days.
Figure 81:
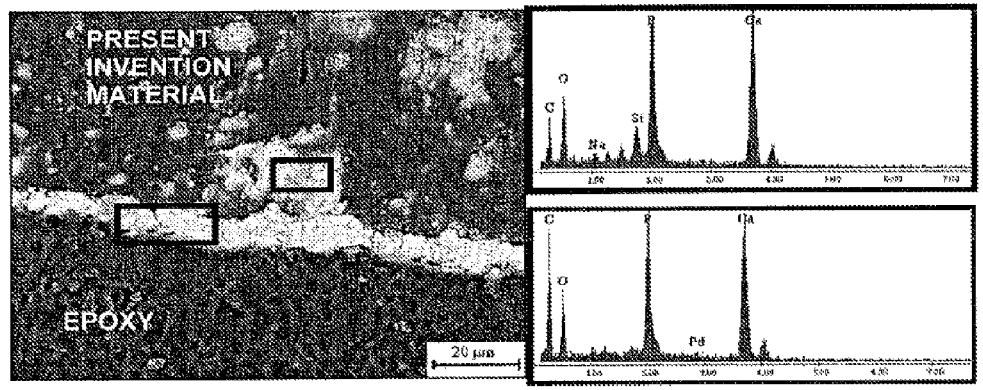
FIG. 81 depicts a SEM photograph showing a cross sectional view of an exemplary embodiment of the present invention comprising 60% PEEK and 40% Combeite glass-ceramic (<53 μm) after immersion in SBF for 21 days along with an energy dispersive spectroscopy (EDS) spectrum of the layers confirming calcium phosphate (CaP) growth.
Figure 82:
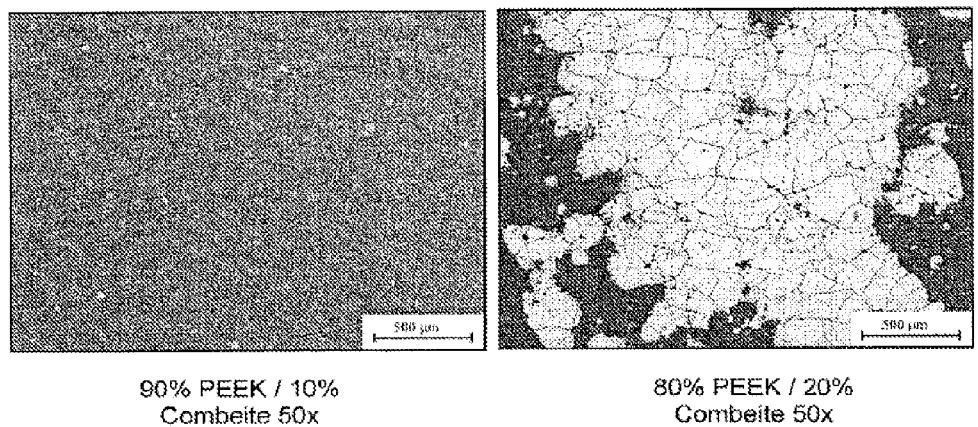
FIG. 82 depicts a series of SEM photographs of certain of the samples shown in FIG. 76 after immersion in SBF for 28 days.

Referring to FIGS. 76-83, composites comprising PEEK and varying weight percentages of Combeite glass-ceramic (having <53 micron average particle size) were prepared using the methods set forth. In vitro bioactivity studies were performed with the composites, prepared as described, using the method of Kokubo, *How useful is SBF in predicting in vivo bone bioactivity*, Biomaterials (2006) 27:2907-2915. After immersion in SBF for 3 days, the formation of a significant amount of calcium phosphate can be observed for the 60% by weight PEEK and 40% by weight Combeite (60/40) sample and formation of calcium phosphate can be seen in the 70% by weight PEEK and 30% by weight Combeite (70/30) sample (FIG. 77). Referring to FIGS. 78-80, the development of increasing amounts of the calcium phosphate for each of the samples can be observed over time; the amount of Combeite bioactive glass-ceramic in the sample proportionally influences the rate at which the calcium phosphate forms. FIG. 82 shows that, after 28 days, a significant amount of calcium phosphate forms on the 80% by weight PEEK and 20% by weight Combeite (80/20) sample and is beginning to form on the 90% by weight PEEK and 10% by weight Combeite (90/10) sample. FIG. 81 shows a cross-section of the bioactive layer of the 60/40 sample after 21 days along with an atomic analysis of the layers. FIG. 81 also shows the significance of the interface of the bioactive glass and its relation to the bioactive layer. By comparison, a sample of 100% PEEK, without the bioactive component, does not result in the formation of calcium phosphate (FIGS. 76-78).

Figure 83:
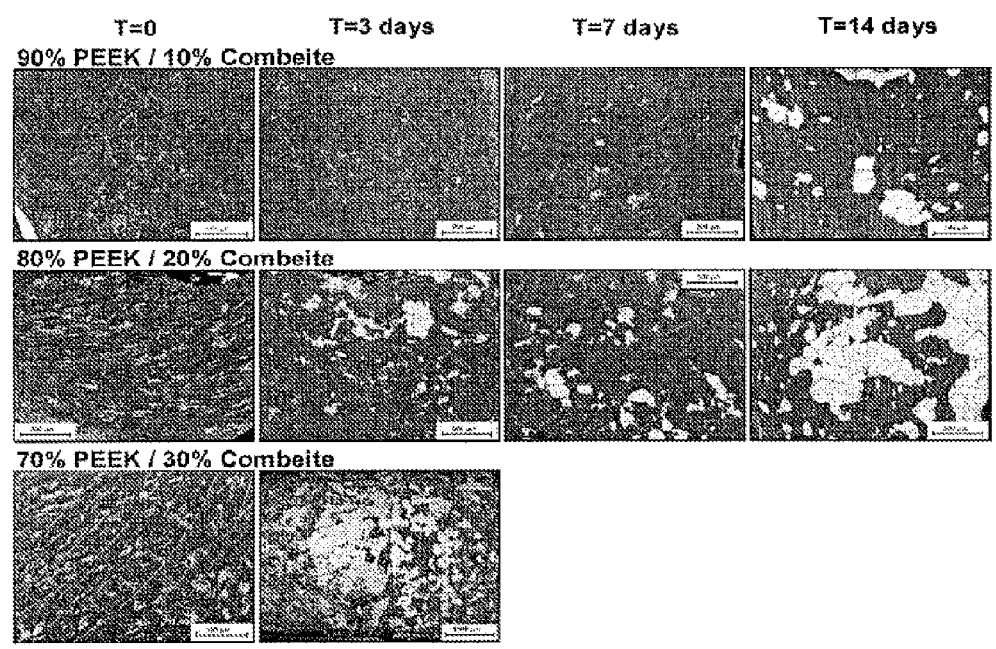
FIG. 83 depicts a series of SEM photographs of various sample embodiments of the present invention comprising PEEK and Combeite glass-ceramic (90 to 150 μm) prior to and after immersion in SBF for up to 14 days.

Also by comparison, FIG. 83 shows the development of calcium phosphate over a 14 day period on samples of PEEK and Combeite, for which the average particle size of the Combeite is about 90 to 150 μm. Comparing FIG. 83 with FIG. 79, it is evident that a significant amount of calcium phosphate has developed on the 90/10 sample (90 to 150 μm) after 14 days, but no calcium phosphate developed on the 90/10 (<53 μm) sample over the same period of time. This suggests that bioactivity may be tailored by altering the size of the bioactive glass.

Figure 84:
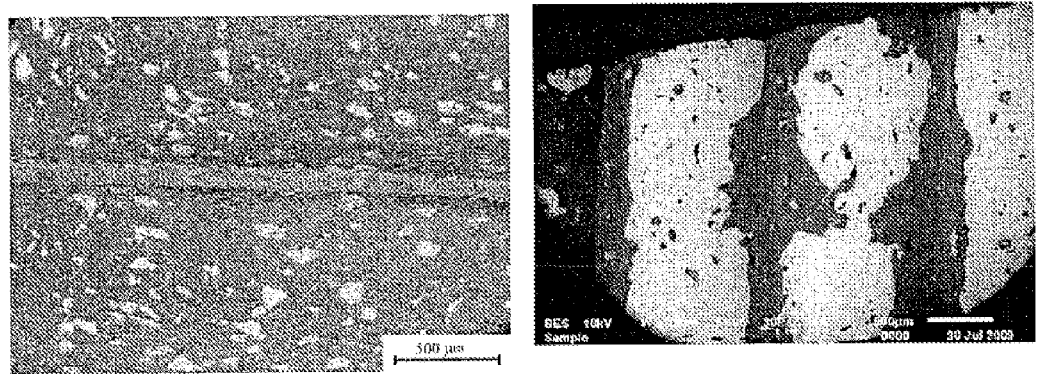
FIG. 84 depicts SEM photographs of an exemplary embodiment of the composite shaped body of the present invention comprising 80% PEEK and 20% Combeite glass-ceramic (90 to 150 μm) before and after immersion in SBF for 7 days.
Figure 85:
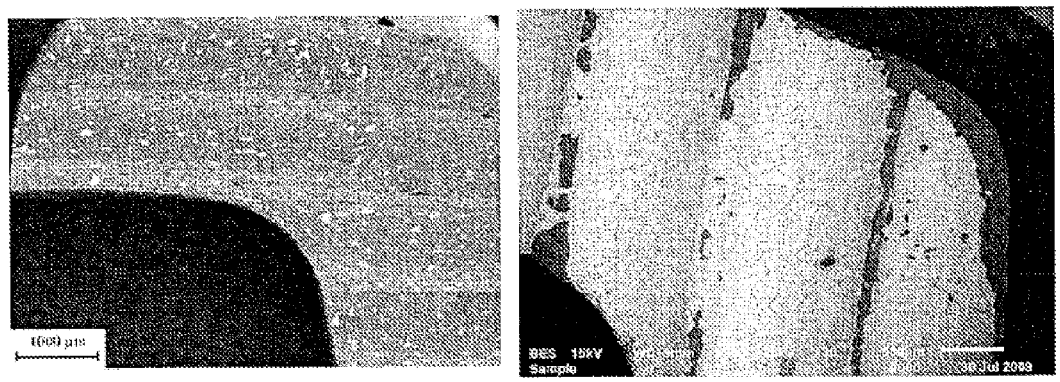
FIG. 85 depicts SEM photographs of an exemplary embodiment of the composite shaped body of the present invention comprising 70% PEEK and 30% Combeite glass-ceramic (90 to 150 μm) before and after immersion in SBF for 7 days.

Composite shaped bodies were manufactured according to the preferred method of the present invention. PEEK polymer and Combeite bioactive glass (90-150 μm) were compounded into pellets using a twin screw, dual hopper extruder. The resultant composite pellets were then injection molded into near net shape articles and further machined to produce shaped spinal implants. FIGS. 84 and 85 display the in vitro bioactivity of two exemplary embodiments of the composite shaped spinal implant after immersion in simulated body fluid for a period of 7 days.

Mechanical Testing

Samples were made with varying grades of PEEK and Combeite bioactive glass and subjected to a host of tests to evaluate the mechanical properties of the samples. These samples were compounded by preblending (dry), adding to a single hopper, and melt mixing in a single screw extruder (Quad die opening; 5 zone 2.5"; single hopper pre-blend; water spritz; air knife, pelletizer; classifier). Resultant composite pellets were then injection molded to standardized shapes for testing (55 Ton Bengel Injection molder; 3-Up family mold for tensile and flexural samples (flexural samples cut in half for Izod impact testing). Table 2 displays the mechanical properties of various materials manufactured in accordance with the single hopper/single screw processing method of the present invention.

TABLE 2

| Formulation | Compressive Strength (MPa) | Compressive Modulus (GPa) | Flexural Strength (MPa) | Flexural Modulus (GPa) | Impact Strength (kJ/m 2) |
|---|---|---|---|---|---|
| 80/20 450G (90-150 μm) | 110-130 | 3.5-4.5 | 165-175 | 5.9-6.2 | 7.7 |
| 70/30 450G (90-150 μm) | 115-130 | 3.5-4.5 | 165-170 | 6.7-6.9 | 8.0 |
| 60/40 150G (<90 μm) | 115-135 | 4.5-5.0 | 145-165 | 8.1-8.2 | 4.8 |
| Victrex 450G* | 120 | | 165 | 4.1 | 8 |
| Victrex 150G* | 120 | | 175 | 3.9 | 5 |

*published values

Additional samples were compounded into composite pellets by Foster Corporation using a 30-40 mm twin screw extruder with a dual hopper feed system. The resultant composite pellets were then injection molded by Spectrum to standardized shapes for testing using a 50-80 ton hydraulic injection molding machine. Table 3 displays the mechanical properties of 80/20 material manufactured in accordance with the twin screw/dual hopper processing method of the present invention in comparison to 100% PEEK (450G).

TABLE 3

| Composition | Comp Strength (MPa) | Comp Modulus (MPa) | Flex Strength (MPa) | Flex Modulus (MPa) | Impact Strength (kJ/m2) complete (hinged) | Tensile Strength (MPa) | Tensile Elong @ break (%) | Tensile Modulus (MPa) |
|---|---|---|---|---|---|---|---|---|
| 80/20 (90-150 μm) 450G | 128 | 3077 | 169 | 5189 | 5.5 (6.6) | 86 | 19 | 5371 |
| Victrex 450G* | 120 | | 165 | 4100 | 8 | 100 | 45 | |

*published values

Dynamic axial fatigue testing of PEEK/Combeite spinal implant samples was also conducted. The spinal implants were comprised of the bioactive composite material of the present invention (low molecular weight 70/30 (90-150 μm glass) material), similar in design to the implant shown in FIG. 5a with a lordotic angle of 7 degrees (anterior to posterior). The purpose of this test is to determine the ability of the material to handle repeated cycles of loading and unloading in a simulated in vivo environment. Testing was conducted at 37° C. in phosphate buffered saline (PBS) (e.g., under simulated in vivo conditions). The implant was capable of withstanding 5 million cycles at an applied load of 2000 Newtons (N) with no observed failure. The results show that the composite material of the present invention can withstand many cycles of loading and unloading as is typically experienced in clinical use.

Melt Flow Rate

The melt flow rate (MFR) of various bioactive composite materials manufactured in accordance with the methods of the present invention at various compounding facilities were measured using an extrusion plastometer, following the methods of ASTM D1238-04c (Procedure A). These results are displayed in Table 5 in relation to the melt flow rates of the 100% PEEK polymer materials (LT1, 450G, LT3, 150G). These results show that as the percentage of bioactive glass is increased, the melt flow rate of the resultant composite material is appreciably decreased.

TABLE 5

| Description | Melt Flow Rate (g/10 min) | Measurement Time (sec) |
|---|---|---|
| 100% LT1 Medical Grade PEEK (high molecular weight PEEK) | 2 | 60 |
| 100% 450G Technical Grade PEEK (high molecular weight PEEK) | 2 | 60 |
| 80/20 (450G/90-150 μm) Twin Screw Compounded at Foster | 0.59 | 60 |
| 80/20 (450G/90-150 μm) Twin Screw Compounded at Polymers Center | 0.94 | 180 |
| 80/20 (450G/90-150 μm) Single Screw Compounded at Infinity | 0.08 | 300 |
| 70/30 (450G/90-150 μm) Twin Screw Compounded at Foster | 0.067 | 600 |
| 80/20 (LT1/<53 μm) Twin Screw Compounded at Polymers Center | 0.12 | 300 |
| 80/20 (450G/<53 μm) Twin Screw Compounded at Polymers Center | 0.1 | 300 |
| 100% LT3 Medical Grade PEEK (low molecular weight PEEK) | 18 | 60 |
| 100% 150G Technical Grade PEEK (low molecular weight PEEK) | 24 | 60 |
| 77/23 (LT3/90-150 μm) Twin Screw Compounded at Foster | 13 | 60 |
| 70/30 (150G/90-150 μm μm) Single Screw Compounded at Infinity | 2.7 | 60 |
| 60/40 (150G/<90) Twin Screw Compounded at Polymers Center | 1.2 | 180 |

"Foster"—Foster West Corporation, North Las Vegas, NV
"Infinity"—Infinity Compounding, Logan, NJ
"Polymer Center"—Polymers Center of Excellence, Charlotte, NC Homogeneity The ash content of various formulations manufactured (at multiple compounding facilities) according to the methods of the present invention was measured according to a modified ASTM D5630-06 procedure B. Two grams of composite pelletized material was burned off at 900 C for 3 hours (tested in triplicate). The results of this ash content testing are displayed in Table 6, and demonstrate the increased accuracy and decreased variability of materials compounded using a twin screw, dual hopper extruder with respect to the target formulation.

TABLE 6

| Sample | Sample Size | Average Bioactive Glass (%) | Standard Deviation | Relative Standard Deviation |
|---|---|---|---|---|
| 80/20 450G 90-150 μm single screw, single hopper (Compounded at Infinity) | 5 | 22.67 | 3.73 | 16.46 |
| 77/23 LT3 90-150 μm twin screw, dual hopper (Compounded at Foster) | 5 | 22.71 | 0.33 | 1.46 |
| 70/30 450G 90-150 μm single screw, single hopper (Compounded at Infinity) | 6 | 34.95 | 4 | 11.43 |
| 70/30 150G 90-150 μm single screw, single hopper (Compounded at Infinity) | 5 | 31.1 | 3.64 | 11.65 |
| 80/20 450G 90-150 μm twin screw, dual hopper (Compounded at Foster) | 3 | 19.49 | 0.12 | 0.60 |
| 70/30 450G 90-150 μm twin screw, dual hopper (Compounded at Foster) | 3 | 29.34 | 0.10 | 0.36 |

Figure 87:
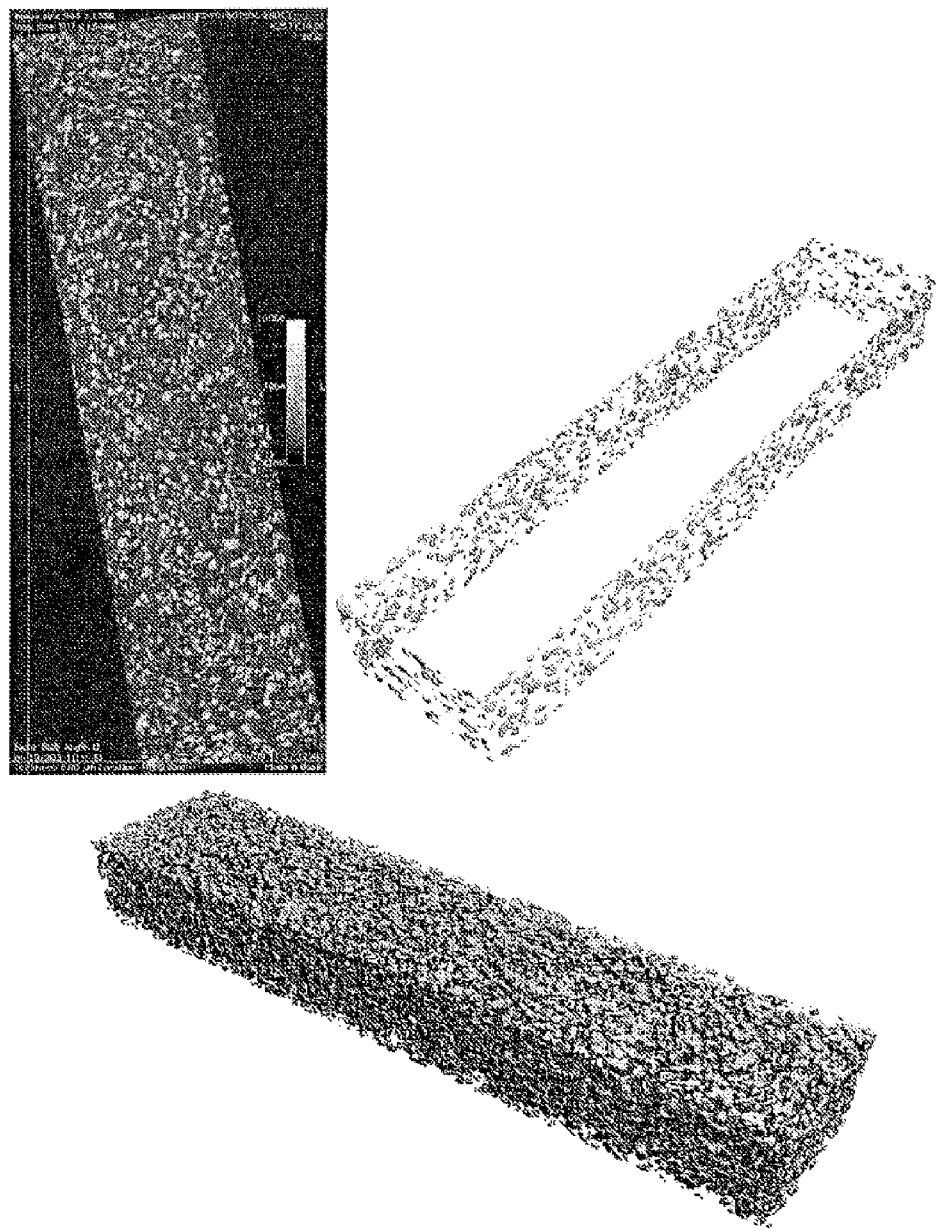
FIG. 87 depicts microCT images and 3-D reconstructions of an exemplary embodiment of the present invention comprising 70% PEEK and 30% Combeite glass-ceramic (90 to 150 μm).

Micro-CT analysis of several bioactive composite materials of the present invention was performed to demonstrate the homogeneity of the glass within the polymer matrix and to quantify the surface area exposure of bioactive glass particles. All samples were scanned on a Scanco Medical pCT 40 system using an x-ray energy level of 70 Kvp and an isotropic voxel size of 6 μm. Particle analysis (volume fraction, size, distribution) was conducted using the Scanco software bundled with the microCT system. Images were binarized to separate the particles from polymer using a fixed threshold value. Representative images and 3-D reconstructions of two exemplary embodiments of the present invention can be seen in FIGS. 86 and 87. Table 7 displays the volume % and surface area % of glass for these two embodiments.

TABLE 7

| Formulation | Volume % Glass per Micro-CT Analysis | Homogeneity (vol % in 4 quadrants) |
|---|---|---|
| 80/20 450G with 90-150 μm Combeite Compounded at Foster | 10.1% | Q1: 9.83<br>Q2: 10.01<br>Q3: 10.28<br>Q4: 10.18 |
| 70/30 450G with 90-150 μm Combeite Compounded at Foster | 18.1% | Q1: 17.87<br>Q2: 18.11<br>Q3: 18.20<br>Q4: 18.35 |

In-Vivo Performance Testing of Bioactive Composites

Various formulations of composite implants of PEEK and Combeite glass-ceramic made in accordance with the methods of the present invention were implanted in the diaphyseal region of sheep long bones (tibia and metatarsal). The bioactive composite test articles were 80/20 LT1/<53 um bioactive glass (80/20S), 80/20 LT1/90-150 um bioactive glass (80/20L), 70/30 LT1/<53 um bioactive glass (70/30S), 60/40 LT3/<90 um (60/40M) bioactive glass. The negative control article was 100% PEEK Optima LT1 and the positive control article was grit-blasted titanium. The surface roughness of representative animal samples was measured using a non-contacting micro laser scanner and is displayed in Table 8.

TABLE 8

| Formulation | Surface Roughness Ra (µm) |
| --- | --- |
| 100% PEEK | 0.96 |
| Grit-blasted Titanium | 1.73 |
| 80/20S | 0.81 |
| 70/30S | 0.62 |
| 80/20L | 1.07 |
| 60/40M | 1.13 |

A push-out test was performed after 12 and 24 weeks of implantation to measure the interfacial shear strength between the implanted materials and the adjacent bone as a measure of bioactivity and bone bonding. After explantation, tibiae and metatarsals were sectioned into individual specimens, each containing 1 defect site. All excess tissue was removed and specimens were cut in half to expose the medial face of the implant. A 5 mm compression pin was used to apply an axial force at a constant displacement rate of 1 mm/min. Load and displacement were recorded. Interfacial Shear stress was calculated by the following equation:

$$\sigma = \frac{F_{max}}{\pi D t}$$

where, Fmax is the maximum push-out force, D is the diameter of the implant (5 mm) and t is the cortical thickness (avg. of 4 measurements).

Statistical analysis was performed using Minitab software. A Ryan-Joiner Normality test performed to confirm normal distribution of the data. A one way ANOVA test was used to assess the interaction between formulation and interfacial shear strength. The Dunnett Method for Treatment vs. Control Comparisons was used to assess significance between the bioactive composite test groups versus the 100% PEEK control at a 95% confidence interval.

Figure 88:
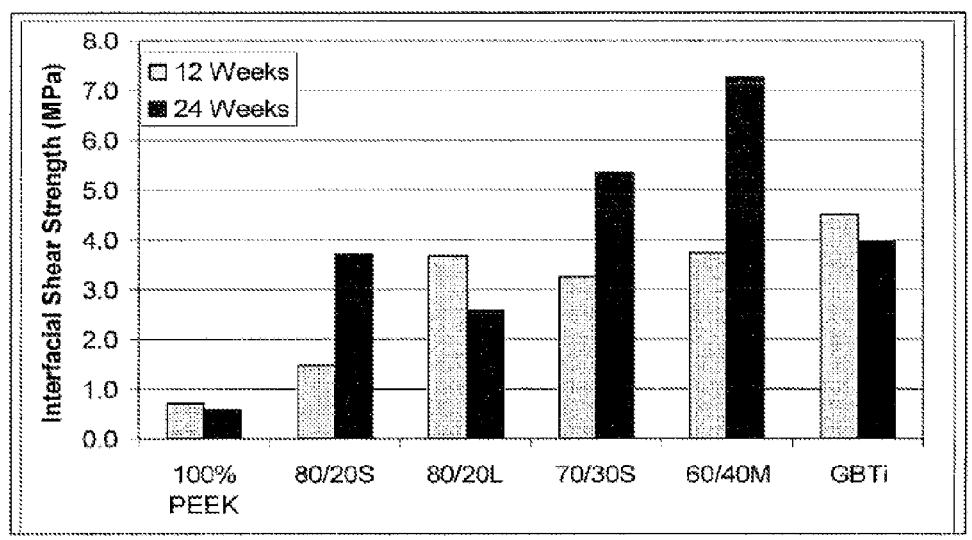
FIG. 88 depicts the maximum interfacial shear strength at the material-bone interface of various embodiments of the present invention after 12 and 24 weeks of implantation in a sheep long bone.

The results of the mechanical push out testing are displayed in FIG. 88. All formulations of the bioactive composite had at least two times greater interfacial shear strength as compared to the 100% polymer control at 12 and 24 weeks. At 12 weeks, all bioactive composite formulations except 80/20S had significantly stronger bone-bonding than 100% PEEK (p<0.05). At 24 weeks the 70/30 and 60/40 bioactive composite materials exhibited significantly greater interfacial shear strength as compared to 100% PEEK (p<0.05). These formulations also exhibited higher average interfacial shear strength as compared to the grit blasted titanium positive control, despite the higher surface roughness of the titanium implant.

Figure 89:
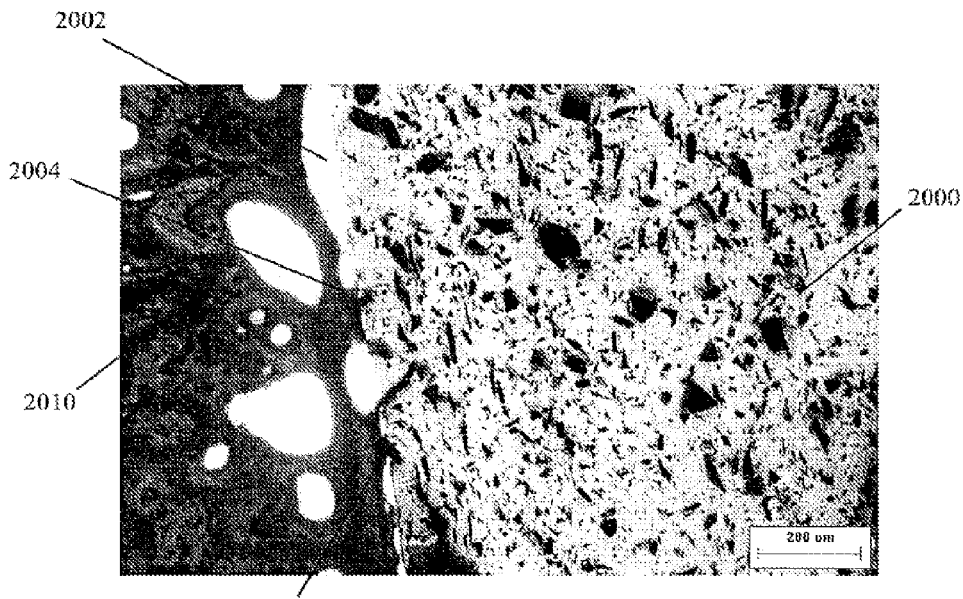
FIG. 89 is a histological image after in-vivo implantation of a dowel comprised of the material of the present invention showing bone adjacent to and growing into the implant without intervening fibrous tissue.
Figure 90:
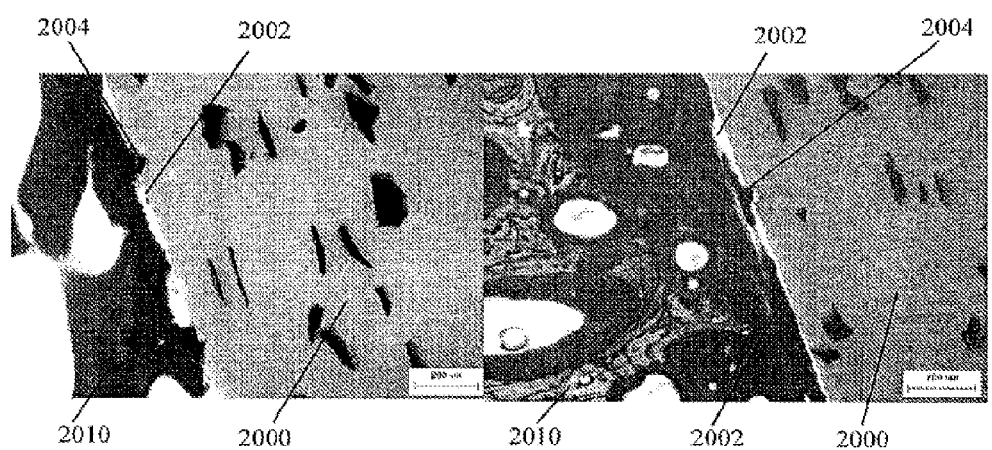
FIG. 90 is a histological image after in-vivo implantation of another dowel comprised of the material of the present invention showing bone adjacent to and growing into the implant without intervening fibrous tissue.

FIGS. 89 and 90 are representative histological images demonstrating the bone bonding nature of the bioactive composite upon in-vivo implantation of dowels comprised of the present invention material into sheep bone. New bone is shown adjacent to the implant without intervening fibrous tissue. For instance, for the implants of FIG. 89 (histology of a 60/40 LT3/<90 µm implant) and FIG. 90 (histology of a 80/20 LT1/90-150 µm implant), new bone 2004 is observed growing into the implant 2000 at locations along the interface 2002 where the glass is in the size range of about 50 microns to about 100 microns, thereby providing a mechanical interlock between the host bone 2010 and the bioactive composite implant 2000.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of preparing a bioactive composite, comprising:
   a) heating polyaryletherketone polymer particles to at least the melting temperature of the polyaryletherketone polymer to at least partially melt the polyaryletherketone polymer particles, wherein the polyaryetherketone polymer particles have a particle size ranging from 1,000 µm to 4,000 µm prior to heating, and wherein the polyaryletherketone polymer has a molecular weight ranging from 70,000 to 120,000 Daltons prior to heating;
   b) adding alkali-containing bioactive glass particles to the at least partially melted polyaryletherketone particles, wherein the alkali-containing bioactive glass particles have a particle size ranging from 1 µm to 500 µm; and
   c) extruding a bioactive composite, wherein the polyaryletherketone polymer is present in an amount of 70% to 85% by weight of the extruded bioactive composite, and wherein the alkali-containing bioactive glass particles is present in an amount of 15% to 30% by weight of the extruded bioactive composite.

2. The method of claim 1, wherein prior to adding the alkali-containing bioactive glass particles, further comprising:
   mixing the at least partially melted polyaryletherketone polymer particles.

3. The method of claim 1, wherein the polyaryletherketone polymer is polyetheretherketone (PEEK).

4. The method of claim 3, wherein the PEEK polymer is present in an amount of 70% to 80% by weight of the extruded bioactive composite, and wherein the alkali-containing bioactive glass particles is present in an amount of 20% to 30% by weight of the extruded bioactive composite.

5. The method of claim 1, wherein the alkali-containing bioactive glass particles are 45S5 or Combeite glass-ceramic.

6. The method of claim 1, wherein the alkali-containing bioactive glass particles have a particle size range from 50 µm to 250 µm.

7. The method of claim 1, wherein the composite is non-resorbable.

8. The method of claim 1, wherein the amount by weight of the alkali-containing bioactive glass particles in the extruded bioactive composite, measured in a plurality of samples taken from the composite, has a standard deviation ranging from 0.10 to 0.33.

9. A method of preparing a homogeneous bioactive shaped body, comprising:
   a) heating polyaryletherketone polymer particles to at least the melting temperature of the polyaryletherketone polymer to at least partially melt the polyaryletherketone polymer particles, wherein the polyaryetherketone polymer particles have a particle size ranging from 1,000 µm to 4,000 µm prior to heating, and wherein the polyaryletherketone polymer has a molecular weight ranging from 70,000 to 120,000 Daltons prior to heating;
b) adding alkali-containing bioactive glass particles to the at least partially melted polyaryletherketone polymer particles, wherein the alkali-containing bioactive glass particles have a particle size ranging from 1 μm to 500 μm; and
c) extruding homogeneous pellets of polyaryletherketone polymer and alkali-containing bioactive glass particles, wherein the polyaryletherketone polymer is present in an amount of 70% to 80% by weight of the homogeneous pellets, and wherein the alkali-containing bioactive glass particles are present in an amount of 20% to 30% by weight of the homogeneous pellets; and
d) injection molding the homogeneous pellets to form the homogeneous bioactive shaped body.

10. The method of claim 9, wherein prior to adding the alkali-containing bioactive glass particles, further comprising:
mixing the at least partially melted polyaryletherketone polymer particles.

11. The method of claim 9, wherein the polyaryletherketone polymer is polyetheretherketone (PEEK).

12. The method of claim 11, wherein the alkali-containing bioactive glass particles has a particle size range from 50 μm to 250 μm.

13. The method of claim 9, wherein the alkali-containing bioactive glass particles are 45S5 or Combeite glass-ceramic.

14. The method of claim 9, wherein the composite is non-resorbable.

15. A method of preparing a bioactive composite, comprising:
a) heating polyetheretherketone (PEEK) polymer particles to at least the melting temperature of the PEEK polymer to at least partially melt the PEEK polymer particles, wherein the PEEK polymer particles have a particle size ranging from 1,000 μm to 4,000 μm prior to heating, and wherein the PEEK polymer has a molecular weight ranging from 100,000 to 120,000 Daltons prior to heating;
b) adding alkali-containing bioactive glass particles to the at least partially melted PEEK polymer particles, wherein the bioactive glass particles have a particle size range from 1 μm to 500 μm; and
c) extruding a bioactive composite, wherein the PEEK polymer is present in an amount of 70% to 80% by weight of the extruded bioactive composite, and wherein the alkali-containing bioactive glass particles is present in an amount of 20% to 30% by weight of the extruded bioactive composite.

16. The method of claim 15, wherein prior to adding the alkali-containing bioactive glass particles, further comprising:
mixing the at least partially melted PEEK polymer particles.

17. The method of claim 1, wherein the bioactive composite is dry mixed.

18. The method of claim 9, wherein the shaped body is prepared without the use of water or a solvent.

19. The method of claim 15, wherein the bioactive composite is dry mixed.

* * * * *